(12) United States Patent
Fukuyama et al.

(10) Patent No.: US 10,584,324 B2
(45) Date of Patent: Mar. 10, 2020

(54) GLUCOAMYLASE VARIANTS AND POLYNUCLEOTIDES ENCODING SAME

(71) Applicant: NOVOZYMES A/S, Bagsvaerd (DK)

(72) Inventors: Shiro Fukuyama, Chiba (JP); Noriko Tsutsumi, Chiba (JP); Keiichi Ayabe, Chiba (JP)

(73) Assignee: NOVOZYMES A/S, Bagsvaerd (DK)

( * ) Notice: Subject to any disclaimer, the term of this patent is extended or adjusted under 35 U.S.C. 154(b) by 190 days.

(21) Appl. No.: 15/520,567

(22) PCT Filed: Oct. 23, 2015

(86) PCT No.: PCT/EP2015/074646
§ 371 (c)(1),
(2) Date: Apr. 20, 2017

(87) PCT Pub. No.: WO2016/062875
PCT Pub. Date: Apr. 28, 2016

(65) Prior Publication Data
US 2017/0306310 A1    Oct. 26, 2017

(30) Foreign Application Priority Data
Oct. 23, 2014   (EP) .................................. 14190070

(51) Int. Cl.
| | | |
|---|---|---|
| *C12N 9/34* | (2006.01) | |
| *C12P 19/14* | (2006.01) | |
| *C12N 15/56* | (2006.01) | |
| *C12N 1/15* | (2006.01) | |
| *C12P 19/02* | (2006.01) | |
| *C12P 7/06* | (2006.01) | |
| *C12N 9/30* | (2006.01) | |
| *C12N 9/44* | (2006.01) | |
| *C12P 7/14* | (2006.01) | |

(52) U.S. Cl.
CPC ........... *C12N 9/2428* (2013.01); *C12N 9/242* (2013.01); *C12N 9/2457* (2013.01); *C12P 7/06* (2013.01); *C12P 7/14* (2013.01); *C12P 19/02* (2013.01); *C12P 19/14* (2013.01); *C12Y 302/01001* (2013.01); *C12Y 302/01003* (2013.01); *C12Y 302/01041* (2013.01); *Y02E 50/17* (2013.01)

(58) Field of Classification Search
None
See application file for complete search history.

(56) References Cited

FOREIGN PATENT DOCUMENTS

| WO | 2007/144424 A2 | 12/2007 | |
|---|---|---|---|
| WO | 2011/066560 A1 | 6/2011 | |
| WO | 2011/068803 A1 | 6/2011 | |
| WO | 2012/064350 A1 | 5/2012 | |
| WO | 2014/177546 A2 | 11/2014 | |
| WO | WO-2018191215 A1 * | 10/2018 | .............. C12P 19/14 |

* cited by examiner

*Primary Examiner* — David Steadman
(74) *Attorney, Agent, or Firm* — David Fazzolare

(57) ABSTRACT

The present invention relates to glucoamylase variants. The present invention also relates to polynucleotides encoding the variants; nucleic acid constructs, vectors, and host cells comprising the polynucleotides; and methods of using the variants.

27 Claims, 1 Drawing Sheet
Specification includes a Sequence Listing.

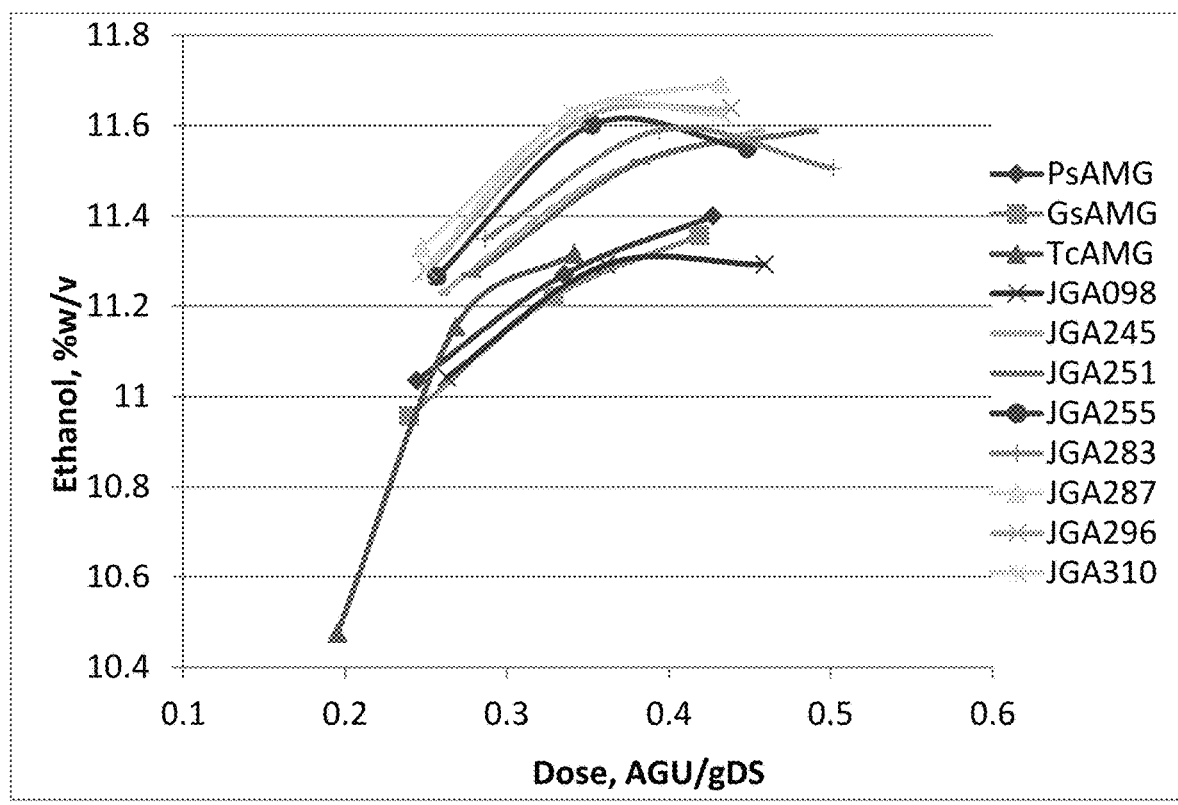

US 10,584,324 B2

GLUCOAMYLASE VARIANTS AND POLYNUCLEOTIDES ENCODING SAME

CROSS-REFERENCE TO RELATED APPLICATIONS

This application is a 35 U.S.C. 371 national application of PCT/EP2015/074646 filed Oct. 23, 2015, which claims priority or the benefit under 35 U.S.C. 119 of European application no. 14190070.4 filed Oct. 23, 2014, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to glucoamylase variants, polynucleotides encoding the variants, methods of producing the variants, and methods of using the variants. Also described are the use of glucoamylases of the invention for starch conversion to produce fermentation products, such as ethanol, and syrups, such as glucose. The invention also relates to a composition comprising a glucoamylase of the invention.

Description of the Related Art

Glucoamylase (1,4-alpha-D-glucan glucohydrolase, EC 3.2.1.3) is an enzyme, which catalyzes the release of D-glucose from the non-reducing ends of starch or related oligo- and polysaccharide molecules. Glucoamylases are produced by several filamentous fungi and yeast, with those from *Aspergillus* being commercially most important.

Commercially, glucoamylases are used to convert starch containing material, which is already partially hydrolyzed by an alpha-amylase, to glucose. The glucose may then be converted directly or indirectly into a fermentation product using a fermenting organism. Examples of commercial fermentation products include alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, beta-carotene); hormones, and other compounds which are difficult to produce synthetically. Fermentation processes are also commonly used in the consumable alcohol (e.g., beer and wine), dairy (e.g., in the production of yogurt and cheese) industries.

The end product may also be syrup. For instance, the end product may be glucose, but may also be converted, e.g., by glucose isomerase to fructose or a mixture composed almost equally of glucose and fructose. This mixture, or a mixture further enriched with fructose, is the most commonly used high fructose corn syrup (HFCS) commercialized throughout the world.

It is an object of the present invention to provide polypeptides having glucoamylase activity and polynucleotides encoding the polypeptides and which provide a high yield in fermentation product production processes, such as ethanol production processes.

WO2011/068803 discloses glucoamylases isolated from the fungus *Gloeophyllum*, in particular from *Gloeophyllum sepiarium* and *Gloeophyllum trabeum*.

WO2014/177546 discloses variants a parent glucoamylase disclosed in WO2011/068803.

The present invention provides glucoamylase variants with improved properties compared to its parent.

SUMMARY OF THE INVENTION

The present invention relates to a glucoamylase variant comprising a substitution at a position corresponding to position 295 of the polypeptide of SEQ ID NO: 2, wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2.

The present invention also relates to a glucoamylase variant, comprising a substitution at one or more positions corresponding to positions 271, 410, 72, 77, 145, 219, 303, 224, 318 of the polypeptide of SEQ ID NO: 2, wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2.

In a further aspect the present invention relates to a glucoamylase variant, comprising a substitution at one or more positions corresponding to positions 271, or 295 or 271 and 295 of the polypeptide of SEQ ID NO: 2, wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2.

The present invention further relates to isolated polynucleotides encoding the variants; nucleic acid constructs, vectors, and host cells comprising the polynucleotides; and methods of producing the variants.

In another aspect, the present invention relates to a process of producing a fermentation product, particularly ethanol, from starch-containing material comprising the steps of: (a) liquefying starch-containing material in the presence of an alpha amylase; (b) saccharifying the liquefied material; and (c) fermenting with a fermenting organism; wherein step (b) is carried out using at least a variant of glucoamylase variant.

In further aspect, the present invention relates to a process of producing a syrup product from starch-containing material, comprising the step of: (a) liquefying starch-containing material in the presence of an alpha amylase; (b) saccharifying the liquefied material in the presence of a variant glucoamylase of the invention.

In still further aspect, the present invention relates to a composition comprising the variant of the invention.

Another aspect the present invention relates to a use of the variant glucoamylase for producing a syrup or a fermentation product.

BRIEF DESCRIPTION OF THE FIGURES

The FIGURE shows ethanol yield as a function of enzyme activity (AGU/gDS) analyzed by HPLC. Selected variant glucoamylases were compared to the parent glucoamylase, JGA098 and to wild type glucoamylases from *Trametes cingulate* (Tc-AMG), *Gloeophyllum sepiarium* (Gs-AMG), *Pycnoporus sanguineus* (Ps-AMG).

DEFINITIONS

Glucoamylase: The term "glucoamylase" (1,4-alpha-D-glucan glucohydrolase, EC 3.2.1.3) is defined as an enzyme, which catalyzes the release of D-glucose from the non-reducing ends of starch or related oligo- and polysaccharide molecules. For purposes of the present invention, glucoamylase activity is determined according to the procedure described in the Examples herein. The Glucoamylase Unit (AGU) is defined as the amount of enzyme, which hydrolyses 1 micromole maltose per minute under the standard conditions 37° C., pH 4.3, substrate: maltose 23.2 mM, buffer: acetate 0.1 M, reaction time 5 minutes.

In another embodiment the polypeptides of the present invention have at least 20%, preferably at least 40%, preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, and even most preferably at least 100% of the glucoamylase activity of the polypeptide of SEQ ID NO: 2.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide; wherein the fragment has glucoamylase activity. In one aspect, a fragment contains at least 454 amino acid residues (e.g., amino acids 1 to 454 of SEQ ID NO: 2), comprising the catalytic domain and having one or more of the substitutions according to the invention.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such improved properties include, but are not limited to, specific activity, reduced glucose inhibition, reduced isomaltose forming activity, increased DE11 activity, and increased thermo-stability. A further improved property is increased EtOH yield when the variant is applied in saccharification followed by fermentation on a liquefied mash.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. The mature polypeptide is disclosed herein as SEQ ID NO: 2.

Mature polypeptide coding sequence: The term "mature polypeptide coding sequence" means a polynucleotide that encodes a mature polypeptide having glucoamylase activity. In one aspect, the mature polypeptide coding sequence is nucleotides 52 to 1728 (or 1731 including the stop codon) of SEQ ID NO: 1. Nucleotides 1 to 51 of SEQ ID NO: 1 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent glucoamylase: The term "parent" or "parent glucoamylase" means a glucoamylase to which an alteration is made to produce the enzyme variants of the present invention. The parent may be a naturally occurring (wild-type) polypeptide or a variant or fragment thereof.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having glucoamylase activity. In one aspect, a subsequence encodes at least the catalytic domain of the variant according to the invention. E.g., contains at least 1362 nucleotides (e.g., nucleotides 52 to 1413 of SEQ ID NO: 1).

Variant: The term "variant" means a polypeptide having glucoamylase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, e.g., at least 40%, at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, and even most preferably at least 100% of the glucoamylase activity of the polypeptide of SEQ ID NO: 2.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Wild-type glucoamylase: The term "wild-type" glucoamylase means a glucoamylase expressed by a naturally occurring microorganism, such as a bacterium, yeast, or filamentous fungus found in nature.

Conventions for Designation of Variants

For purposes of the present invention, the mature polypeptide disclosed in SEQ ID NO: 2 is used to determine the corresponding amino acid residue in another glucoamylase. The amino acid sequence of another glucoamylase is aligned with the mature polypeptide disclosed in SEQ ID NO: 2, and based on the alignment, the amino acid position number corresponding to any amino acid residue in the mature polypeptide disclosed in SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another glucoamylase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other enzyme has diverged from the polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions.

For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions.

For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions.

For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G - K - A |

Multiple Alterations.

Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different Alterations.

Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:

"Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to glucoamylase variants, comprising an alteration, in particular a substitution, at one or more (e.g., several) positions corresponding to positions 295, 224, 410, 271, 72, 77, 145, 318, 60, 32, 83, 163, 169, 303, 219 and 73 of the polypeptide of SEQ ID NO: 2 and the variant has glucoamylase activity. In particular the variants have improved properties compared to the glucoamylase disclosed as SEQ ID NO: 2. Particularly, the improved properties are increased specific activity and/or reduced glucose inhibition, and/or increased ethanol yield in SSF (simultaneous saccharification and fermentation). Saccharification and fermentation may also be performed in separate steps. The variants according to the invention have at least 75%, at least 80%, at least 85%, at least 90%, at least 95%, at least 96%, at least 97%, at least 98%, or at least 99%, but less than 100% sequence identity to the polypeptide of SEQ ID NO: 2.

In a particular aspect the invention relates to a glucoamylase variant comprising a substitution at a position corresponding to position 295 of the polypeptide of SEQ ID NO: 2, wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2.

In another particular aspect the invention relates to a glucoamylase variant, comprising a substitution at one or more positions corresponding to positions 271, 410, 72, 77, 145, 219, 303, 224, 318 of the polypeptide of SEQ ID NO: 2, wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2.

In another aspect the invention relates to a glucoamylase variant, comprising a substitution at one or more positions corresponding to positions 271, or 295 or 271 and 295 of the polypeptide of SEQ ID NO: 2, wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2.

The parent glucoamylase, SEQ ID NO: 2, has a proline at positions 95 and 121. This combination provides improved thermo-stability to the parent glucoamylase. In one particular embodiment, prolines at positions 95 and 121 are maintained unchanged in all variants of the invention.

Variants

The present invention provides glucoamylase variants, comprising an alteration, in particular a substitution, at one or more (e.g., several) positions corresponding to positions 295, 224, 410, 271, 72, 77, 145, 318, 60, 32, 83, 163, 169, 303, 219 and 73 and the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2.

In one embodiment the variant is isolated.

In an embodiment, the variant has sequence identity of at least 85%, at least 90%, at least 91%, at least 92%, at least 93%, at least 94%, at least 95%, at least 96%, at least 97%, at least 98%, or at least 99%, but less than 100%, to the amino acid sequence of the parent glucoamylase.

In another embodiment, the variant has at least at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 2.

In another aspect, a variant comprises an alteration, in particular a substitution, at one or more (e.g., several) positions corresponding to positions 295, 224, 410, 271, 72, 77, 145, 318, 60, 32, 83, 163, 169, 303, 219 and 73. In another aspect, a variant comprises a substitution at two positions corresponding to any of positions 295, 224, 410, 271, 72, 77, 145, 318, 60, 32, 83, 163, 169, 303, 219 nd 73. In another aspect, a variant comprises a substitution at three positions corresponding to any of positions 295, 224, 410, 271, 72, 77, 145, 318, 60, 32, 83, 163, 169, 303, 219 and 73. In another aspect, a variant comprises a substitution at four positions corresponding to any of positions 295, 224, 410, 271, 72, 77, 145, 318, 60, 32, 83, 163, 169, 303, 219 and 73. In another aspect, a variant comprises an alteration at five positions corresponding to any of positions 295, 224, 410, 271, 72, 77, 145, 318, 60, 32, 83, 163, 169, 303, 219 and 73. In another aspect, a variant comprises a substitution at six positions corresponding to any of positions 295, 224, 410, 271, 72, 77, 145, 318, 60, 32, 83, 163, 169, 303, 219 and 73. In another aspect, a variant comprises a substitution at seven positions corresponding to any of positions 295, 224, 410, 271, 72, 77, 145, 318, 60, 32, 83, 163, 169, 303, 219 and 73. In another aspect, a variant comprises a substitution at eight positions corresponding to any of positions 295, 224, 410, 271, 72, 77, 145, 318, 60, 32, 83, 163, 169, 303, 219 and 73. In another aspect, a variant comprises a substitution at each position corresponding to positions 295, 224, 410, 271, 72, 77, 145, 318, 60, 32, 83, 163, 169, 303, 219 and 73.

In another aspect, the variant comprises or consists of an alteration, in particular a substitution at a position corresponding to position 295. In another aspect, the amino acid at a position corresponding to position 295 is substituted with Ala, Arg, Asn, Asp, Cys, Gln, Glu, Gly, His, Ile, Leu, Lys, Met, Phe, Pro, Ser, Thr, Trp, or Val, preferably with Phe or Trp. In another aspect, the variant comprises or consists of the substitution Y295F or Y295W of the polypeptide of SEQ ID NO: 2.

In another aspect, the variant comprises or consists of an alteration, in particular a substitution at a position corresponding to position 224. In another aspect, the amino acid at a position corresponding to position 224 is substituted with Ala, Arg, Asn, Asp, Cys, Gln, Glu, Gly, His, Ile, Lys, Met, Phe, Pro, Ser, Thr, Trp, Tyr or Val, preferably with Gln or Ala or Ile or Thr. In another aspect, the variant comprises or consists of the substitution L224Q or L224A or L224I or L224T of the polypeptide of SEQ ID NO: 2.

In another aspect, the variant comprises or consists of an alteration, in particular a substitution at a position corresponding to position 72. In another aspect, the amino acid at a position corresponding to position 72 is substituted with Ala, Arg, Asn, Cys, Gin, Glu, Gly, His, Ile, Leu, Lys, Met, Phe, Pro, Ser, Thr, Trp, Tyr or Val, preferably with Val. In another aspect, the variant comprises or consists of the substitution D72V of the polypeptide of SEQ ID NO: 2.

In another aspect, the variant comprises or consists of an alteration, in particular a substitution at a position corresponding to position 77. In another aspect, the amino acid at a position corresponding to position 77 is substituted with Ala, Arg, Asn, Asp, Cys, Gin, Glu, Gly, His, Ile, Lys, Met, Phe, Pro, Ser, Thr, Trp, Tyr, or Val, preferably with Ala or Val. In another aspect, the variant comprises or consists of the substitution L77A or L77V of the polypeptide of SEQ ID NO: 2.

In another aspect, the variant comprises or consists of an alteration, in particular a substitution at a position corresponding to position 145. In another aspect, the amino acid at a position corresponding to position 145 is substituted with Ala, Arg, Asn, Asp, Cys, Gin, Glu, Gly, His, Ile, Lys, Met, Phe, Pro, Ser, Thr, Trp, Tyr, or Val, preferably with Ala. In another aspect, the variant comprises or consists of the substitution L145A of the polypeptide of SEQ ID NO: 2.

In another aspect, the variant comprises or consists of an alteration, in particular a substitution at a position corresponding to position 410. In another aspect, the amino acid at a position corresponding to position 410 is substituted with Ala, Asn, Asp, Cys, Gin, Glu, Gly, His, Ile, Leu, Lys, Met, Phe, Pro, Ser, Thr, Trp, Tyr, or Val, preferably with Ala or Gin or His or Lys. In another aspect, the variant comprises or consists of the substitution R410A or R410Q or R410H or R410K of the polypeptide of SEQ ID NO: 2.

In another aspect, the variant comprises or consists of an alteration, in particular a substitution at a position corresponding to position 318. In another aspect, the amino acid at a position corresponding to position 318 is substituted with Ala, Arg, Asn, Asp, Cys, Glu, Gly, His, Ile, Leu, Lys, Met, Phe, Pro, Ser, Thr, Trp, Val, or Tyr, preferably with Trp or Phe or Val or Tyr. In another aspect, the variant comprises or consists of the substitution Q318W or Q318F or Q318V or Q318Y of the polypeptide of SEQ ID NO: 2.

In another aspect, the variant comprises or consists of an alteration, in particular a substitution at a position corresponding to position 271. In another aspect, the amino acid at a position corresponding to position 271 is substituted with, Ala, Asn, Arg, Asp, Cys, Gln, Glu, Gly, His, Ile, Leu, Lys, Met, Phe, Pro, Ser, Trp, Val, or Tyr, preferably with Gln or Asn or Ala or Ser or Val. In another aspect, the variant comprises or consists of the substitution T271Q or T271N or T271A or T271S or T271V of the polypeptide of SEQ ID NO: 2.

In another aspect, the variant comprises or consists of an alteration, in particular a substitution at a position corresponding to position 60. In another aspect, the amino acid at a position corresponding to position 60 is substituted with Ala, Arg, Asn, Asp, Cys, Gln, Glu, Gly, His, Ile, Leu, Lys, Met, Pro, Ser, Thr, Trp, Tyr, or Val preferably with Leu. In another aspect, the variant comprises or consists of the substitution F60L of the polypeptide of SEQ ID NO: 2.

In another aspect, the variant comprises or consists of an alteration, in particular a substitution at a position corresponding to position 73. In another aspect, the amino acid at a position corresponding to position 73 is substituted with Ala, Arg, Asn, Asp, Cys, Gln, Glu, Gly, His, Ile, Leu, Lys, Met, Phe, Pro, Thr, Trp, Tyr, or Val preferably with Ala. In another aspect, the variant comprises or consists of the substitution S73A of the polypeptide of SEQ ID NO: 2.

In another aspect, the variant comprises or consists of an alteration, in particular a substitution at a position corresponding to position 32. In another aspect, the amino acid at a position corresponding to position 32 is substituted with Arg, Asn, Asp, Cys, Gln, Glu, Gly, His, Ile, Leu, Lys, Met, Phe, Pro, Ser, Thr, Trp, Tyr, or Val preferably with Val. In another aspect, the variant comprises or consists of the substitution A32V of the polypeptide of SEQ ID NO: 2.

In another aspect, the variant comprises or consists of an alteration, in particular a substitution at a position corresponding to position 83. In another aspect, the amino acid at a position corresponding to position 83 is substituted with Ala, Arg, Asn, Asp, Cys, Gln, Glu, Gly, His, Ile, Leu, Lys, Met, Phe, Pro, Thr, Trp, Tyr, or Val preferably with Asp. In another aspect, the variant comprises or consists of the substitution S83D of the polypeptide of SEQ ID NO: 2.

In another aspect, the variant comprises or consists of an alteration, in particular a substitution at a position corresponding to position 163. In another aspect, the amino acid at a position corresponding to position 163 is substituted with Ala, Arg, Asp, Cys, Gln, Glu, Gly, His, Ile, Leu, Lys, Met, Phe, Pro, Ser, Thr, Trp, Tyr, or Val preferably with Ala. In another aspect, the variant comprises or consists of the substitution N163A or N163W of the polypeptide of SEQ ID NO: 2.

In another aspect, the variant comprises or consists of an alteration, in particular a substitution at a position corresponding to position 169. In another aspect, the amino acid at a position corresponding to position 169 is substituted with Ala, Arg, Asn, Asp, Cys, Gln, Glu, Gly, His, Ile, Leu, Lys, Met, Phe, Pro, Ser, Thr, Trp, or Tyr, preferably with Ile. In another aspect, the variant comprises or consists of the substitution V169I of the polypeptide of SEQ ID NO: 2.

In another aspect, the variant comprises or consists of an alteration, in particular a substitution at a position corresponding to position 219. In another aspect, the amino acid at a position corresponding to position 219 is substituted with Ala, Arg, Asn, Asp, Cys, Gln, Glu, Gly, His, Ile, Leu, Lys, Met, Phe, Pro, Ser, Trp, Tyr, or Val preferably with Asp or Arg. In another aspect, the variant comprises or consists of the substitution T219R or T219D of the polypeptide of SEQ ID NO: 2.

In another aspect, the variant comprises or consists of an alteration, in particular a substitution at a position corresponding to position 303. In another aspect, the amino acid at a position corresponding to position 303 is substituted with Ala, Arg, Asn, Asp, Cys, Gin, Glu, Gly, His, Ile, Leu, Lys, Met, Phe, Pro, Thr, Trp, Tyr, or Val preferably with Glu or Asn. In another aspect, the variant comprises or consists of the substitution 5303E or 5303N of the polypeptide of SEQ ID NO: 2.

In another aspect, the variant alterations comprise or consist of substitutions at positions corresponding to positions 295 and 224, such as those described above.

In another aspect, the variant alterations comprise or consist of substitutions at positions corresponding to positions 295 and 410, such as those described above.

In another aspect, the variant alterations comprise or consist of substitutions at positions corresponding to positions 295 and 271, such as those described above.

In another aspect, the variant alterations comprise or consist of substitutions at positions corresponding to positions 295 and 72, such as those described above.

In another aspect, the variant alterations comprise or consist of substitutions at positions corresponding to positions 295 and 77, such as those described above.

In another aspect, the variant alterations comprise or consist of substitutions at positions corresponding to positions 295 and 145, such as those described above.

In another aspect, the variant alterations comprise or consist of substitutions at positions corresponding to positions 295 and 318, such as those described above.

In another aspect, the variant alterations comprise or consist of substitutions at positions corresponding to positions 295 and 60, such as those described above.

In another aspect, the variant alterations comprise or consist of substitutions at positions corresponding to positions 295 and 73, such as those described above.

In another aspect, the variant alterations comprise or consist of substitutions at positions corresponding to positions 224 and 410, such as those described above.

In another aspect, the variant alterations comprise or consist of substitutions at positions corresponding to positions 224 and 271, such as those described above.

In another aspect, the variant alterations comprise or consist of substitutions at positions corresponding to positions 224 and 72, such as those described above.

In another aspect, the variant alterations comprise or consist of substitutions at positions corresponding to positions 224 and 77, such as those described above.

In another aspect, the variant alterations comprise or consist of substitutions at positions corresponding to positions 224 and 145, such as those described above.

In another aspect, the variant alterations comprise or consist of substitutions at positions corresponding to positions 224 and 318, such as those described above.

In another aspect, the variant alterations comprise or consist of substitutions at positions corresponding to positions 224 and 60, such as those described above.

In another aspect, the variant alterations comprise or consist of substitutions at positions corresponding to positions 224 and 73, such as those described above.

In another aspect, the variant alterations comprise or consist of substitutions at positions corresponding to positions 410 and 271, such as those described above.

In another aspect, the variant alterations comprise or consist of substitutions at positions corresponding to positions 410 and 72, such as those described above.

In another aspect, the variant alterations comprise or consist of substitutions at positions corresponding to positions 410 and 77, such as those described above.

In another aspect, the variant alterations comprise or consist of substitutions at positions corresponding to positions 410 and 145, such as those described above.

In another aspect, the variant alterations comprise or consist of substitutions at positions corresponding to positions 410 and 318, such as those described above.

In another aspect, the variant alterations comprise or consist of substitutions at positions corresponding to positions 410 and 60, such as those described above.

In another aspect, the variant alterations comprise or consist of substitutions at positions corresponding to positions 410 and 73, such as those described above.

In another aspect, the variant alterations comprise or consist of substitutions at positions corresponding to positions 271 and 72, such as those described above.

In another aspect, the variant alterations comprise or consist of substitutions at positions corresponding to positions 271 and 77, such as those described above.

In another aspect, the variant alterations comprise or consist of substitutions at positions corresponding to positions 271 and 145, such as those described above.

In another aspect, the variant alterations comprise or consist of substitutions at positions corresponding to positions 271 and 318, such as those described above.

In another aspect, the variant alterations comprise or consist of substitutions at positions corresponding to positions 271 and 60, such as those described above.

In another aspect, the variant alterations comprise or consist of substitutions at positions corresponding to positions 271 and 73, such as those described above.

In another aspect, the variant alterations comprise or consist of substitutions at positions corresponding to positions 72 and 77, such as those described above.

In another aspect, the variant alterations comprise or consist of substitutions at positions corresponding to positions 72 and 145, such as those described above.

In another aspect, the variant alterations comprise or consist of substitutions at positions corresponding to positions 72 and 318, such as those described above.

In another aspect, the variant alterations comprise or consist of substitutions at positions corresponding to positions 72 and 60, such as those described above.

In another aspect, the variant alterations comprise or consist of substitutions at positions corresponding to positions 72 and 73, such as those described above.

In another aspect, the variant alterations comprise or consist of substitutions at positions corresponding to positions 77 and 145, such as those described above.

In another aspect, the variant alterations comprise or consist of substitutions at positions corresponding to positions 77 and 318, such as those described above.

In another aspect, the variant alterations comprise or consist of substitutions at positions corresponding to positions 77 and 60, such as those described above.

In another aspect, the variant alterations comprise or consist of substitutions at positions corresponding to positions 77 and 73, such as those described above.

In another aspect, the variant alterations comprise or consist of substitutions at positions corresponding to positions 145 and 318, such as those described above.

In another aspect, the variant alterations comprise or consist of substitutions at positions corresponding to positions 145 and 60, such as those described above.

In another aspect, the variant alterations comprise or consist of substitutions at positions corresponding to positions 145 and 73, such as those described above.

In another aspect, the variant alterations comprise or consist of substitutions at positions corresponding to positions 318 and 60, such as those described above.

In another aspect, the variant alterations comprise or consist of substitutions at positions corresponding to positions 318 and 73, such as those described above.

In another aspect, the variant alterations comprise or consist of substitutions at positions corresponding to positions 60 and 73, such as those described above.

In another aspect, the variant alterations comprise or consist of substitutions at positions corresponding to positions 295 and 224 and 410, such as those described above.

In another aspect, the variant alterations comprise or consist of substitutions at positions corresponding to positions 295 and 224 and 271, such as those described above.

In another aspect, the variant alterations comprise or consist of substitutions at positions corresponding to positions 295 and 224 and 72, such as those described above.

In another aspect, the variant alterations comprise or consist of substitutions at positions corresponding to positions 295 and 224 and 77, such as those described above.

In another aspect, the variant alterations comprise or consist of substitutions at positions corresponding to positions 295 and 224 and 145, such as those described above.

In another aspect, the variant alterations comprise or consist of substitutions at positions corresponding to positions 295 and 224 and 318, such as those described above.

In another aspect, the variant alterations comprise or consist of substitutions at positions corresponding to positions 295 and 224 and 60, such as those described above.

In another aspect, the variant alterations comprise or consist of substitutions at positions corresponding to positions 295 and 224 and 73, such as those described above.

In another aspect, the variant alterations comprise or consist of substitutions at positions corresponding to positions 295 and 410 and 271, such as those described above.

In another aspect, the variant alterations comprise or consist of substitutions at positions corresponding to positions 295 and 410 and 72, such as those described above.

In another aspect, the variant alterations comprise or consist of substitutions at positions corresponding to positions 295 and 410 and 77, such as those described above.

In another aspect, the variant alterations comprise or consist of substitutions at positions corresponding to positions 295 and 410 and 145, such as those described above.

In another aspect, the variant alterations comprise or consist of substitutions at positions corresponding to positions 295 and 410 and 318, such as those described above.

In another aspect, the variant alterations comprise or consist of substitutions at positions corresponding to positions 295 and 410 and 60, such as those described above.

In another aspect, the variant alterations comprise or consist of substitutions at positions corresponding to positions 295 and 410 and 73, such as those described above.

In another aspect, the variant alterations comprise or consist of substitutions at positions corresponding to positions 295 and 271 and 72, such as those described above.

In another aspect, the variant alterations comprise or consist of substitutions at positions corresponding to positions 295 and 271 and 77, such as those described above.

In another aspect, the variant alterations comprise or consist of substitutions at positions corresponding to positions 295 and 271 and 145, such as those described above.

In another aspect, the variant alterations comprise or consist of substitutions at positions corresponding to positions 295 and 271 and 318, such as those described above.

In another aspect, the variant alterations comprise or consist of substitutions at positions corresponding to positions 295 and 271 and 60, such as those described above.

In another aspect, the variant alterations comprise or consist of substitutions at positions corresponding to positions 295 and 271 and 73, such as those described above.

In another aspect, the variant alterations comprise or consist of substitutions at positions corresponding to positions 295 and 72 and 77, such as those described above.

In another aspect, the variant alterations comprise or consist of substitutions at positions corresponding to positions 295 and 72 and 145, such as those described above.

In another aspect, the variant alterations comprise or consist of substitutions at positions corresponding to positions 295 and 72 and 318, such as those described above.

In another aspect, the variant alterations comprise or consist of substitutions at positions corresponding to positions 295 and 72 and 60, such as those described above.

In another aspect, the variant alterations comprise or consist of substitutions at positions corresponding to positions 295 and 72 and 73, such as those described above.

In another aspect, the variant alterations comprise or consist of substitutions at positions corresponding to positions 295 and 77 and 145, such as those described above.

In another aspect, the variant alterations comprise or consist of substitutions at positions corresponding to positions 295 and 77 and 318, such as those described above.

In another aspect, the variant alterations comprise or consist of substitutions at positions corresponding to positions 295 and 77 and 60, such as those described above.

In another aspect, the variant alterations comprise or consist of substitutions at positions corresponding to positions 295 and 77 and 73, such as those described above.

In another aspect, the variant alterations comprise or consist of substitutions at positions corresponding to positions 295 and 145 and 318, such as those described above.

In another aspect, the variant alterations comprise or consist of substitutions at positions corresponding to positions 295 and 145 and 60, such as those described above.

In another aspect, the variant alterations comprise or consist of substitutions at positions corresponding to positions 295 and 145 and 73, such as those described above.

In another aspect, the variant alterations comprise or consist of substitutions at positions corresponding to positions 295 and 318 and 60, such as those described above.

In another aspect, the variant alterations comprise or consist of substitutions at positions corresponding to positions 295 and 318 and 73, such as those described above.

In another aspect, the variant alterations comprise or consist of substitutions at positions corresponding to positions 295 and 60 and 73, such as those described above.

In another aspect, the variant alterations comprise or consist of substitutions at positions corresponding to positions 224 and 410 and 271, such as those described above.

In another aspect, the variant alterations comprise or consist of substitutions at positions corresponding to positions 224 and 410 and 72, such as those described above.

In another aspect, the variant alterations comprise or consist of substitutions at positions corresponding to positions 224 and 410 and 77, such as those described above.

In another aspect, the variant alterations comprise or consist of substitutions at positions corresponding to positions 224 and 410 and 145, such as those described above.

In another aspect, the variant alterations comprise or consist of substitutions at positions corresponding to positions 224 and 410 and 318, such as those described above.

In another aspect, the variant alterations comprise or consist of substitutions at positions corresponding to positions 224 and 410 and 60, such as those described above.

In another aspect, the variant alterations comprise or consist of substitutions at positions corresponding to positions 224 and 410 and 73, such as those described above.

In another aspect, the variant alterations comprise or consist of substitutions at positions corresponding to positions 224 and 271 and 72, such as those described above.

In another aspect, the variant alterations comprise or consist of substitutions at positions corresponding to positions 224 and 271 and 77, such as those described above.

In another aspect, the variant alterations comprise or consist of substitutions at positions corresponding to positions 224 and 271 and 145, such as those described above.

In another aspect, the variant alterations comprise or consist of substitutions at positions corresponding to positions 224 and 271 and 318, such as those described above.

In another aspect, the variant alterations comprise or consist of substitutions at positions corresponding to positions 224 and 271 and 60, such as those described above.

In another aspect, the variant alterations comprise or consist of substitutions at positions corresponding to positions 224 and 271 and 73, such as those described above.

In another aspect, the variant alterations comprise or consist of substitutions at positions corresponding to positions 224 and 72 and 77, such as those described above.

In another aspect, the variant alterations comprise or consist of substitutions at positions corresponding to positions 224 and 72 and 145, such as those described above.

In another aspect, the variant alterations comprise or consist of substitutions at positions corresponding to positions 224 and 72 and 318, such as those described above.

In another aspect, the variant alterations comprise or consist of substitutions at positions corresponding to positions 224 and 72 and 60, such as those described above.

In another aspect, the variant alterations comprise or consist of substitutions at positions corresponding to positions 224 and 72 and 73, such as those described above.

In another aspect, the variant alterations comprise or consist of substitutions at positions corresponding to positions 224 and 77 and 145, such as those described above.

In another aspect, the variant alterations comprise or consist of substitutions at positions corresponding to positions 224 and 77 and 318, such as those described above.

In another aspect, the variant alterations comprise or consist of substitutions at positions corresponding to positions 224 and 77 and 60, such as those described above.

In another aspect, the variant alterations comprise or consist of substitutions at positions corresponding to positions 224 and 77 and 73, such as those described above.

In another aspect, the variant alterations comprise or consist of substitutions at positions corresponding to positions 224 and 145 and 318, such as those described above.

In another aspect, the variant alterations comprise or consist of substitutions at positions corresponding to positions 224 and 145 and 60, such as those described above.

In another aspect, the variant alterations comprise or consist of substitutions at positions corresponding to positions 224 and 145 and 73, such as those described above.

In another aspect, the variant alterations comprise or consist of substitutions at positions corresponding to positions 224 and 318 and 60, such as those described above.

In another aspect, the variant alterations comprise or consist of substitutions at positions corresponding to positions 224 and 318 and 73, such as those described above.

In another aspect, the variant alterations comprise or consist of substitutions at positions corresponding to positions 224 and 60 and 73, such as those described above.

In another aspect, the variant alterations comprise or consist of substitutions at positions corresponding to positions 410 and 271 and 72, such as those described above.

In another aspect, the variant alterations comprise or consist of substitutions at positions corresponding to positions 410 and 271 and 77, such as those described above.

In another aspect, the variant alterations comprise or consist of substitutions at positions corresponding to positions 410 and 271 and 145, such as those described above.

In another aspect, the variant alterations comprise or consist of substitutions at positions corresponding to positions 410 and 271 and 318, such as those described above.

In another aspect, the variant alterations comprise or consist of substitutions at positions corresponding to positions 410 and 271 and 60, such as those described above.

In another aspect, the variant alterations comprise or consist of substitutions at positions corresponding to positions 410 and 271 and 73, such as those described above.

In another aspect, the variant alterations comprise or consist of substitutions at positions corresponding to positions 410 and 72 and 77, such as those described above.

In another aspect, the variant alterations comprise or consist of substitutions at positions corresponding to positions 410 and 72 and 145, such as those described above.

In another aspect, the variant alterations comprise or consist of substitutions at positions corresponding to positions 410 and 72 and 318, such as those described above.

In another aspect, the variant alterations comprise or consist of substitutions at positions corresponding to positions 410 and 72 and 60, such as those described above.

In another aspect, the variant alterations comprise or consist of substitutions at positions corresponding to positions 410 and 72 and 73, such as those described above.

In another aspect, the variant alterations comprise or consist of substitutions at positions corresponding to positions 410 and 77 and 145, such as those described above.

In another aspect, the variant alterations comprise or consist of substitutions at positions corresponding to positions 410 and 77 and 318, such as those described above.

In another aspect, the variant alterations comprise or consist of substitutions at positions corresponding to positions 410 and 77 and 60, such as those described above.

In another aspect, the variant alterations comprise or consist of substitutions at positions corresponding to positions 410 and 77 and 73, such as those described above.

In another aspect, the variant alterations comprise or consist of substitutions at positions corresponding to positions 410 and 145 and 318, such as those described above.

In another aspect, the variant alterations comprise or consist of substitutions at positions corresponding to positions 410 and 145 and 60, such as those described above.

In another aspect, the variant alterations comprise or consist of substitutions at positions corresponding to positions 410 and 145 and 73, such as those described above.

In another aspect, the variant alterations comprise or consist of substitutions at positions corresponding to positions 410 and 318 and 60, such as those described above.

In another aspect, the variant alterations comprise or consist of substitutions at positions corresponding to positions 410 and 318 and 73, such as those described above.

In another aspect, the variant alterations comprise or consist of substitutions at positions corresponding to positions 410 and 60 and 73, such as those described above.

In another aspect, the variant alterations comprise or consist of substitutions at positions corresponding to positions 271 and 72 and 77, such as those described above.

In another aspect, the variant alterations comprise or consist of substitutions at positions corresponding to positions 271 and 72 and 145, such as those described above.

In another aspect, the variant alterations comprise or consist of substitutions at positions corresponding to positions 271 and 72 and 318, such as those described above.

In another aspect, the variant alterations comprise or consist of substitutions at positions corresponding to positions 271 and 72 and 60, such as those described above.

In another aspect, the variant alterations comprise or consist of substitutions at positions corresponding to positions 271 and 72 and 73, such as those described above.

In another aspect, the variant alterations comprise or consist of substitutions at positions corresponding to positions 271 and 77 and 145, such as those described above.

In another aspect, the variant alterations comprise or consist of substitutions at positions corresponding to positions 271 and 77 and 318, such as those described above.

In another aspect, the variant alterations comprise or consist of substitutions at positions corresponding to positions 271 and 77 and 60, such as those described above.

In another aspect, the variant alterations comprise or consist of substitutions at positions corresponding to positions 271 and 77 and 73, such as those described above.

In another aspect, the variant alterations comprise or consist of substitutions at positions corresponding to positions 271 and 145 and 318, such as those described above.

In another aspect, the variant alterations comprise or consist of substitutions at positions corresponding to positions 271 and 145 and 60, such as those described above.

In another aspect, the variant alterations comprise or consist of substitutions at positions corresponding to positions 271 and 145 and 73, such as those described above.

In another aspect, the variant alterations comprise or consist of substitutions at positions corresponding to positions 271 and 318 and 60, such as those described above.

In another aspect, the variant alterations comprise or consist of substitutions at positions corresponding to positions 271 and 318 and 73, such as those described above.

In another aspect, the variant alterations comprise or consist of substitutions at positions corresponding to positions 271 and 60 and 73, such as those described above.

In another aspect, the variant alterations comprise or consist of substitutions at positions corresponding to positions 72 and 77 and 145, such as those described above.

In another aspect, the variant alterations comprise or consist of substitutions at positions corresponding to positions 72 and 77 and 318, such as those described above.

In another aspect, the variant alterations comprise or consist of substitutions at positions corresponding to positions 72 and 77 and 60, such as those described above.

In another aspect, the variant alterations comprise or consist of substitutions at positions corresponding to positions 72 and 77 and 73, such as those described above.

In another aspect, the variant alterations comprise or consist of substitutions at positions corresponding to positions 72 and 145 and 318, such as those described above.

In another aspect, the variant alterations comprise or consist of substitutions at positions corresponding to positions 72 and 145 and 60, such as those described above.

In another aspect, the variant alterations comprise or consist of substitutions at positions corresponding to positions 72 and 145 and 73, such as those described above.

In another aspect, the variant alterations comprise or consist of substitutions at positions corresponding to positions 72 and 318 and 60, such as those described above.

In another aspect, the variant alterations comprise or consist of substitutions at positions corresponding to positions 72 and 318 and 73, such as those described above.

In another aspect, the variant alterations comprise or consist of substitutions at positions corresponding to positions 72 and 60 and 73, such as those described above.

In another aspect, the variant alterations comprise or consist of substitutions at positions corresponding to positions 77 and 145 and 318, such as those described above.

In another aspect, the variant alterations comprise or consist of substitutions at positions corresponding to positions 77 and 145 and 60, such as those described above.

In another aspect, the variant alterations comprise or consist of substitutions at positions corresponding to positions 77 and 145 and 73, such as those described above.

In another aspect, the variant alterations comprise or consist of substitutions at positions corresponding to positions 77 and 318 and 60, such as those described above.

In another aspect, the variant alterations comprise or consist of substitutions at positions corresponding to positions 77 and 318 and 73, such as those described above.

In another aspect, the variant alterations comprise or consist of substitutions at positions corresponding to positions 77 and 60 and 73, such as those described above.

In another aspect, the variant alterations comprise or consist of substitutions at positions corresponding to positions 145 and 318 and 60, such as those described above.

In another aspect, the variant alterations comprise or consist of substitutions at positions corresponding to positions 145 and 318 and 73, such as those described above.

In another aspect, the variant alterations comprise or consist of substitutions at positions corresponding to positions 145 and 60 and 73, such as those described above.

In another aspect, the variant alterations comprise or consist of substitutions at positions corresponding to positions 318 and 60 and 73, such as those described above.

In another aspect, the variant alterations comprise or consist of substitutions at positions corresponding to positions 295 and 224 and 410 and 271, such as those described above.

In another aspect, the variant alterations comprise or consist of substitutions at positions corresponding to positions 295 and 224 and 410 and 72, such as those described above.

In another aspect, the variant alterations comprise or consist of substitutions at positions corresponding to positions 295 and 224 and 410 and 77, such as those described above.

In another aspect, the variant alterations comprise or consist of substitutions at positions corresponding to positions 295 and 224 and 410 and 145, such as those described above.

In another aspect, the variant alterations comprise or consist of substitutions at positions corresponding to positions 295 and 224 and 410 and 318, such as those described above.

In another aspect, the variant alterations comprise or consist of substitutions at positions corresponding to positions 295 and 224 and 410 and 60, such as those described above.

In another aspect, the variant alterations comprise or consist of substitutions at positions corresponding to positions 295 and 224 and 410 and 73, such as those described above.

In another aspect, the variant alterations comprise or consist of substitutions at positions corresponding to positions 295 and 224 and 271 and 72, such as those described above.

In another aspect, the variant alterations comprise or consist of substitutions at positions corresponding to positions 295 and 224 and 271 and 77, such as those described above.

In another aspect, the variant alterations comprise or consist of substitutions at positions corresponding to positions 295 and 224 and 271 and 145, such as those described above.

In another aspect, the variant alterations comprise or consist of substitutions at positions corresponding to positions 295 and 224 and 271 and 318, such as those described above.

In another aspect, the variant alterations comprise or consist of substitutions at positions corresponding to positions 295 and 224 and 271 and 60, such as those described above.

In another aspect, the variant alterations comprise or consist of substitutions at positions corresponding to positions 295 and 224 and 271 and 73, such as those described above.

In another aspect, the variant alterations comprise or consist of substitutions at positions corresponding to positions 295 and 224 and 72 and 77, such as those described above.

In another aspect, the variant alterations comprise or consist of substitutions at positions corresponding to positions 295 and 224 and 72 and 145, such as those described above.

In another aspect, the variant alterations comprise or consist of substitutions at positions corresponding to positions 295 and 224 and 72 and 318, such as those described above.

In another aspect, the variant alterations comprise or consist of substitutions at positions corresponding to positions 295 and 224 and 72 and 60, such as those described above.

In another aspect, the variant alterations comprise or consist of substitutions at positions corresponding to positions 295 and 224 and 72 and 73, such as those described above.

In another aspect, the variant alterations comprise or consist of substitutions at positions corresponding to positions 295 and 224 and 77 and 145, such as those described above.

In another aspect, the variant alterations comprise or consist of substitutions at positions corresponding to positions 295 and 224 and 77 and 318, such as those described above.

In another aspect, the variant alterations comprise or consist of substitutions at positions corresponding to positions 295 and 224 and 77 and 60, such as those described above.

In another aspect, the variant alterations comprise or consist of substitutions at positions corresponding to positions 295 and 224 and 77 and 73, such as those described above.

In another aspect, the variant alterations comprise or consist of substitutions at positions corresponding to positions 295 and 224 and 145 and 318, such as those described above.

In another aspect, the variant alterations comprise or consist of substitutions at positions corresponding to positions 295 and 224 and 145 and 60, such as those described above.

In another aspect, the variant alterations comprise or consist of substitutions at positions corresponding to positions 295 and 224 and 145 and 73, such as those described above.

In another aspect, the variant alterations comprise or consist of substitutions at positions corresponding to positions 295 and 224 and 318 and 60, such as those described above.

In another aspect, the variant alterations comprise or consist of substitutions at positions corresponding to positions 295 and 224 and 318 and 73, such as those described above.

In another aspect, the variant alterations comprise or consist of substitutions at positions corresponding to positions 295 and 224 and 60 and 73, such as those described above.

In another aspect, the variant alterations comprise or consist of substitutions at positions corresponding to positions 295 and 410 and 271 and 72, such as those described above.

In another aspect, the variant alterations comprise or consist of substitutions at positions corresponding to positions 295 and 410 and 271 and 77, such as those described above.

In another aspect, the variant alterations comprise or consist of substitutions at positions corresponding to positions 295 and 410 and 271 and 145, such as those described above.

In another aspect, the variant alterations comprise or consist of substitutions at positions corresponding to positions 295 and 410 and 271 and 318, such as those described above.

In another aspect, the variant alterations comprise or consist of substitutions at positions corresponding to positions 295 and 410 and 271 and 60, such as those described above.

In another aspect, the variant alterations comprise or consist of substitutions at positions corresponding to positions 295 and 410 and 271 and 73, such as those described above.

In another aspect, the variant alterations comprise or consist of substitutions at positions corresponding to positions 295 and 410 and 72 and 77, such as those described above.

In another aspect, the variant alterations comprise or consist of substitutions at positions corresponding to positions 295 and 410 and 72 and 145, such as those described above.

In another aspect, the variant alterations comprise or consist of substitutions at positions corresponding to positions 295 and 410 and 72 and 318, such as those described above.

In another aspect, the variant alterations comprise or consist of substitutions at positions corresponding to positions 295 and 410 and 72 and 60, such as those described above.

In another aspect, the variant alterations comprise or consist of substitutions at positions corresponding to positions 295 and 410 and 72 and 73, such as those described above.

In another aspect, the variant alterations comprise or consist of substitutions at positions corresponding to positions 295 and 410 and 77 and 145, such as those described above.

In another aspect, the variant alterations comprise or consist of substitutions at positions corresponding to positions 295 and 410 and 77 and 318, such as those described above.

In another aspect, the variant alterations comprise or consist of substitutions at positions corresponding to positions 295 and 410 and 77 and 60, such as those described above.

In another aspect, the variant alterations comprise or consist of substitutions at positions corresponding to positions 295 and 410 and 77 and 73, such as those described above.

In another aspect, the variant alterations comprise or consist of substitutions at positions corresponding to positions 295 and 410 and 145 and 318, such as those described above.

In another aspect, the variant alterations comprise or consist of substitutions at positions corresponding to positions 295 and 410 and 145 and 60, such as those described above.

In another aspect, the variant alterations comprise or consist of substitutions at positions corresponding to positions 295 and 410 and 145 and 73, such as those described above.

In another aspect, the variant alterations comprise or consist of substitutions at positions corresponding to positions 295 and 410 and 318 and 60, such as those described above.

In another aspect, the variant alterations comprise or consist of substitutions at positions corresponding to positions 295 and 410 and 318 and 73, such as those described above.

In another aspect, the variant alterations comprise or consist of substitutions at positions corresponding to positions 295 and 410 and 60 and 73, such as those described above.

In another aspect, the variant alterations comprise or consist of substitutions at positions corresponding to positions 295 and 271 and 72 and 77, such as those described above.

In another aspect, the variant alterations comprise or consist of substitutions at positions corresponding to positions 295 and 271 and 72 and 145, such as those described above.

In another aspect, the variant alterations comprise or consist of substitutions at positions corresponding to positions 295 and 271 and 72 and 318, such as those described above.

In another aspect, the variant alterations comprise or consist of substitutions at positions corresponding to positions 295 and 271 and 72 and 60, such as those described above.

In another aspect, the variant alterations comprise or consist of substitutions at positions corresponding to positions 295 and 271 and 72 and 73, such as those described above.

In another aspect, the variant alterations comprise or consist of substitutions at positions corresponding to positions 295 and 271 and 77 and 145, such as those described above.

In another aspect, the variant alterations comprise or consist of substitutions at positions corresponding to positions 295 and 271 and 77 and 318, such as those described above.

In another aspect, the variant alterations comprise or consist of substitutions at positions corresponding to positions 295 and 271 and 77 and 60, such as those described above.

In another aspect, the variant alterations comprise or consist of substitutions at positions corresponding to positions 295 and 271 and 77 and 73, such as those described above.

In another aspect, the variant alterations comprise or consist of substitutions at positions corresponding to positions 295 and 271 and 145 and 318, such as those described above.

In another aspect, the variant alterations comprise or consist of substitutions at positions corresponding to positions 295 and 271 and 145 and 60, such as those described above.

In another aspect, the variant alterations comprise or consist of substitutions at positions corresponding to positions 295 and 271 and 145 and 73, such as those described above.

In another aspect, the variant alterations comprise or consist of substitutions at positions corresponding to positions 295 and 271 and 318 and 60, such as those described above.

In another aspect, the variant alterations comprise or consist of substitutions at positions corresponding to positions 295 and 271 and 318 and 73, such as those described above.

In another aspect, the variant alterations comprise or consist of substitutions at positions corresponding to positions 295 and 271 and 60 and 73, such as those described above.

In another aspect, the variant alterations comprise or consist of substitutions at positions corresponding to positions 295 and 72 and 77 and 145, such as those described above.

In another aspect, the variant alterations comprise or consist of substitutions at positions corresponding to positions 295 and 72 and 77 and 318, such as those described above.

In another aspect, the variant alterations comprise or consist of substitutions at positions corresponding to positions 295 and 72 and 77 and 60, such as those described above.

In another aspect, the variant alterations comprise or consist of substitutions at positions corresponding to positions 295 and 72 and 77 and 73, such as those described above.

In another aspect, the variant alterations comprise or consist of substitutions at positions corresponding to positions 295 and 72 and 145 and 318, such as those described above.

In another aspect, the variant alterations comprise or consist of substitutions at positions corresponding to positions 295 and 72 and 145 and 60, such as those described above.

In another aspect, the variant alterations comprise or consist of substitutions at positions corresponding to positions 295 and 72 and 145 and 73, such as those described above.

In another aspect, the variant alterations comprise or consist of substitutions at positions corresponding to positions 295 and 72 and 318 and 60, such as those described above.

In another aspect, the variant alterations comprise or consist of substitutions at positions corresponding to positions 295 and 72 and 318 and 73, such as those described above.

In another aspect, the variant alterations comprise or consist of substitutions at positions corresponding to positions 295 and 72 and 60 and 73, such as those described above.

In another aspect, the variant alterations comprise or consist of substitutions at positions corresponding to positions 295 and 77 and 145 and 318, such as those described above.

In another aspect, the variant alterations comprise or consist of substitutions at positions corresponding to positions 295 and 77 and 145 and 60, such as those described above.

In another aspect, the variant alterations comprise or consist of substitutions at positions corresponding to positions 295 and 77 and 145 and 73, such as those described above.

In another aspect, the variant alterations comprise or consist of substitutions at positions corresponding to positions 295 and 77 and 318 and 60, such as those described above.

In another aspect, the variant alterations comprise or consist of substitutions at positions corresponding to positions 295 and 77 and 318 and 73, such as those described above.

In another aspect, the variant alterations comprise or consist of substitutions at positions corresponding to positions 295 and 77 and 60 and 73, such as those described above.

In another aspect, the variant alterations comprise or consist of substitutions at positions corresponding to positions 295 and 145 and 318 and 60, such as those described above.

In another aspect, the variant alterations comprise or consist of substitutions at positions corresponding to positions 295 and 145 and 318 and 73, such as those described above.

In another aspect, the variant alterations comprise or consist of substitutions at positions corresponding to positions 295 and 145 and 60 and 73, such as those described above.

In another aspect, the variant alterations comprise or consist of substitutions at positions corresponding to positions 295 and 318 and 60 and 73, such as those described above.

In another aspect, the variant alterations comprise or consist of substitutions at positions corresponding to positions 224 and 410 and 271 and 72, such as those described above.

In another aspect, the variant alterations comprise or consist of substitutions at positions corresponding to positions 224 and 410 and 271 and 77, such as those described above.

In another aspect, the variant alterations comprise or consist of substitutions at positions corresponding to positions 224 and 410 and 271 and 145, such as those described above.

In another aspect, the variant alterations comprise or consist of substitutions at positions corresponding to positions 224 and 410 and 271 and 318, such as those described above.

In another aspect, the variant alterations comprise or consist of substitutions at positions corresponding to positions 224 and 410 and 271 and 60, such as those described above.

In another aspect, the variant alterations comprise or consist of substitutions at positions corresponding to positions 224 and 410 and 271 and 73, such as those described above.

In another aspect, the variant alterations comprise or consist of substitutions at positions corresponding to positions 224 and 410 and 72 and 77, such as those described above.

In another aspect, the variant alterations comprise or consist of substitutions at positions corresponding to positions 224 and 410 and 72 and 145, such as those described above.

In another aspect, the variant alterations comprise or consist of substitutions at positions corresponding to positions 224 and 410 and 72 and 318, such as those described above.

In another aspect, the variant alterations comprise or consist of substitutions at positions corresponding to positions 224 and 410 and 72 and 60, such as those described above.

In another aspect, the variant alterations comprise or consist of substitutions at positions corresponding to positions 224 and 410 and 72 and 73, such as those described above.

In another aspect, the variant alterations comprise or consist of substitutions at positions corresponding to positions 224 and 410 and 77 and 145, such as those described above.

In another aspect, the variant alterations comprise or consist of substitutions at positions corresponding to positions 224 and 410 and 77 and 318, such as those described above.

In another aspect, the variant alterations comprise or consist of substitutions at positions corresponding to positions 224 and 410 and 77 and 60, such as those described above.

In another aspect, the variant alterations comprise or consist of substitutions at positions corresponding to positions 224 and 410 and 77 and 73, such as those described above.

In another aspect, the variant alterations comprise or consist of substitutions at positions corresponding to positions 224 and 410 and 145 and 318, such as those described above.

In another aspect, the variant alterations comprise or consist of substitutions at positions corresponding to positions 224 and 410 and 145 and 60, such as those described above.

In another aspect, the variant alterations comprise or consist of substitutions at positions corresponding to positions 224 and 410 and 145 and 73, such as those described above.

In another aspect, the variant alterations comprise or consist of substitutions at positions corresponding to positions 224 and 410 and 318 and 60, such as those described above.

In another aspect, the variant alterations comprise or consist of substitutions at positions corresponding to positions 224 and 410 and 318 and 73, such as those described above.

In another aspect, the variant alterations comprise or consist of substitutions at positions corresponding to positions 224 and 410 and 60 and 73, such as those described above.

In another aspect, the variant alterations comprise or consist of substitutions at positions corresponding to positions 224 and 271 and 72 and 77, such as those described above.

In another aspect, the variant alterations comprise or consist of substitutions at positions corresponding to positions 224 and 271 and 72 and 145, such as those described above.

In another aspect, the variant alterations comprise or consist of substitutions at positions corresponding to positions 224 and 271 and 72 and 318, such as those described above.

In another aspect, the variant alterations comprise or consist of substitutions at positions corresponding to positions 224 and 271 and 72 and 60, such as those described above.

In another aspect, the variant alterations comprise or consist of substitutions at positions corresponding to positions 224 and 271 and 72 and 73, such as those described above.

In another aspect, the variant alterations comprise or consist of substitutions at positions corresponding to positions 224 and 271 and 77 and 145, such as those described above.

In another aspect, the variant alterations comprise or consist of substitutions at positions corresponding to positions 224 and 271 and 77 and 318, such as those described above.

In another aspect, the variant alterations comprise or consist of substitutions at positions corresponding to positions 224 and 271 and 77 and 60, such as those described above.

In another aspect, the variant alterations comprise or consist of substitutions at positions corresponding to positions 224 and 271 and 77 and 73, such as those described above.

In another aspect, the variant alterations comprise or consist of substitutions at positions corresponding to positions 224 and 271 and 145 and 318, such as those described above.

In another aspect, the variant alterations comprise or consist of substitutions at positions corresponding to positions 224 and 271 and 145 and 60, such as those described above.

In another aspect, the variant alterations comprise or consist of substitutions at positions corresponding to positions 224 and 271 and 145 and 73, such as those described above.

In another aspect, the variant alterations comprise or consist of substitutions at positions corresponding to positions 224 and 271 and 318 and 60, such as those described above.

In another aspect, the variant alterations comprise or consist of substitutions at positions corresponding to positions 224 and 271 and 318 and 73, such as those described above.

In another aspect, the variant alterations comprise or consist of substitutions at positions corresponding to positions 224 and 271 and 60 and 73, such as those described above.

In another aspect, the variant alterations comprise or consist of substitutions at positions corresponding to positions 224 and 72 and 77 and 145, such as those described above.

In another aspect, the variant alterations comprise or consist of substitutions at positions corresponding to positions 224 and 72 and 77 and 318, such as those described above.

In another aspect, the variant alterations comprise or consist of substitutions at positions corresponding to positions 224 and 72 and 77 and 60, such as those described above.

In another aspect, the variant alterations comprise or consist of substitutions at positions corresponding to positions 224 and 72 and 77 and 73, such as those described above.

In another aspect, the variant alterations comprise or consist of substitutions at positions corresponding to positions 224 and 72 and 145 and 318, such as those described above.

In another aspect, the variant alterations comprise or consist of substitutions at positions corresponding to positions 224 and 72 and 145 and 60, such as those described above.

In another aspect, the variant alterations comprise or consist of substitutions at positions corresponding to positions 224 and 72 and 145 and 73, such as those described above.

In another aspect, the variant alterations comprise or consist of substitutions at positions corresponding to positions 224 and 72 and 318 and 60, such as those described above.

In another aspect, the variant alterations comprise or consist of substitutions at positions corresponding to positions 224 and 72 and 318 and 73, such as those described above.

In another aspect, the variant alterations comprise or consist of substitutions at positions corresponding to positions 224 and 72 and 60 and 73, such as those described above.

In another aspect, the variant alterations comprise or consist of substitutions at positions corresponding to positions 224 and 77 and 145 and 318, such as those described above.

In another aspect, the variant alterations comprise or consist of substitutions at positions corresponding to positions 224 and 77 and 145 and 60, such as those described above.

In another aspect, the variant alterations comprise or consist of substitutions at positions corresponding to positions 224 and 77 and 145 and 73, such as those described above.

In another aspect, the variant alterations comprise or consist of substitutions at positions corresponding to positions 224 and 77 and 318 and 60, such as those described above.

In another aspect, the variant alterations comprise or consist of substitutions at positions corresponding to positions 224 and 77 and 318 and 73, such as those described above.

In another aspect, the variant alterations comprise or consist of substitutions at positions corresponding to positions 224 and 77 and 60 and 73, such as those described above.

In another aspect, the variant alterations comprise or consist of substitutions at positions corresponding to positions 224 and 145 and 318 and 60, such as those described above.

In another aspect, the variant alterations comprise or consist of substitutions at positions corresponding to positions 224 and 145 and 318 and 73, such as those described above.

In another aspect, the variant alterations comprise or consist of substitutions at positions corresponding to positions 224 and 145 and 60 and 73, such as those described above.

In another aspect, the variant alterations comprise or consist of substitutions at positions corresponding to positions 224 and 318 and 60 and 73, such as those described above.

In another aspect, the variant alterations comprise or consist of substitutions at positions corresponding to positions 410 and 271 and 72 and 77, such as those described above.

In another aspect, the variant alterations comprise or consist of substitutions at positions corresponding to positions 410 and 271 and 72 and 145, such as those described above.

In another aspect, the variant alterations comprise or consist of substitutions at positions corresponding to positions 410 and 271 and 72 and 318, such as those described above.

In another aspect, the variant alterations comprise or consist of substitutions at positions corresponding to positions 410 and 271 and 72 and 60, such as those described above.

In another aspect, the variant alterations comprise or consist of substitutions at positions corresponding to positions 410 and 271 and 72 and 73, such as those described above.

In another aspect, the variant alterations comprise or consist of substitutions at positions corresponding to positions 410 and 271 and 77 and 145, such as those described above.

In another aspect, the variant alterations comprise or consist of substitutions at positions corresponding to positions 410 and 271 and 77 and 318, such as those described above.

In another aspect, the variant alterations comprise or consist of substitutions at positions corresponding to positions 410 and 271 and 77 and 60, such as those described above.

In another aspect, the variant alterations comprise or consist of substitutions at positions corresponding to positions 410 and 271 and 77 and 73, such as those described above.

In another aspect, the variant alterations comprise or consist of substitutions at positions corresponding to positions 410 and 271 and 145 and 318, such as those described above.

In another aspect, the variant alterations comprise or consist of substitutions at positions corresponding to positions 410 and 271 and 145 and 60, such as those described above.

In another aspect, the variant alterations comprise or consist of substitutions at positions corresponding to positions 410 and 271 and 145 and 73, such as those described above.

In another aspect, the variant alterations comprise or consist of substitutions at positions corresponding to positions 410 and 271 and 318 and 60, such as those described above.

In another aspect, the variant alterations comprise or consist of substitutions at positions corresponding to positions 410 and 271 and 318 and 73, such as those described above.

In another aspect, the variant alterations comprise or consist of substitutions at positions corresponding to positions 410 and 271 and 60 and 73, such as those described above.

In another aspect, the variant alterations comprise or consist of substitutions at positions corresponding to positions 410 and 72 and 77 and 145, such as those described above.

In another aspect, the variant alterations comprise or consist of substitutions at positions corresponding to positions 410 and 72 and 77 and 318, such as those described above.

In another aspect, the variant alterations comprise or consist of substitutions at positions corresponding to positions 410 and 72 and 77 and 60, such as those described above.

In another aspect, the variant alterations comprise or consist of substitutions at positions corresponding to positions 410 and 72 and 77 and 73, such as those described above.

In another aspect, the variant alterations comprise or consist of substitutions at positions corresponding to positions 410 and 72 and 145 and 318, such as those described above.

In another aspect, the variant alterations comprise or consist of substitutions at positions corresponding to positions 410 and 72 and 145 and 60, such as those described above.

In another aspect, the variant alterations comprise or consist of substitutions at positions corresponding to positions 410 and 72 and 145 and 73, such as those described above.

In another aspect, the variant alterations comprise or consist of substitutions at positions corresponding to positions 410 and 72 and 318 and 60, such as those described above.

In another aspect, the variant alterations comprise or consist of substitutions at positions corresponding to positions 410 and 72 and 318 and 73, such as those described above.

In another aspect, the variant alterations comprise or consist of substitutions at positions corresponding to positions 410 and 72 and 60 and 73, such as those described above.

In another aspect, the variant alterations comprise or consist of substitutions at positions corresponding to positions 410 and 77 and 145 and 318, such as those described above.

In another aspect, the variant alterations comprise or consist of substitutions at positions corresponding to positions 410 and 77 and 145 and 60, such as those described above.

In another aspect, the variant alterations comprise or consist of substitutions at positions corresponding to positions 410 and 77 and 145 and 73, such as those described above.

In another aspect, the variant alterations comprise or consist of substitutions at positions corresponding to positions 410 and 77 and 318 and 60, such as those described above.

In another aspect, the variant alterations comprise or consist of substitutions at positions corresponding to positions 410 and 77 and 318 and 73, such as those described above.

In another aspect, the variant alterations comprise or consist of substitutions at positions corresponding to positions 410 and 77 and 60 and 73, such as those described above.

In another aspect, the variant alterations comprise or consist of substitutions at positions corresponding to positions 410 and 145 and 318 and 60, such as those described above.

In another aspect, the variant alterations comprise or consist of substitutions at positions corresponding to positions 410 and 145 and 318 and 73, such as those described above.

In another aspect, the variant alterations comprise or consist of substitutions at positions corresponding to positions 410 and 145 and 60 and 73, such as those described above.

In another aspect, the variant alterations comprise or consist of substitutions at positions corresponding to positions 410 and 318 and 60 and 73, such as those described above.

In another aspect, the variant alterations comprise or consist of substitutions at positions corresponding to positions 271 and 72 and 77 and 145, such as those described above.

In another aspect, the variant alterations comprise or consist of substitutions at positions corresponding to positions 271 and 72 and 77 and 318, such as those described above.

In another aspect, the variant alterations comprise or consist of substitutions at positions corresponding to positions 271 and 72 and 77 and 60, such as those described above.

In another aspect, the variant alterations comprise or consist of substitutions at positions corresponding to positions 271 and 72 and 77 and 73, such as those described above.

In another aspect, the variant alterations comprise or consist of substitutions at positions corresponding to positions 271 and 72 and 145 and 318, such as those described above.

In another aspect, the variant alterations comprise or consist of substitutions at positions corresponding to positions 271 and 72 and 145 and 60, such as those described above.

In another aspect, the variant alterations comprise or consist of substitutions at positions corresponding to positions 271 and 72 and 145 and 73, such as those described above.

In another aspect, the variant alterations comprise or consist of substitutions at positions corresponding to positions 271 and 72 and 318 and 60, such as those described above.

In another aspect, the variant alterations comprise or consist of substitutions at positions corresponding to positions 271 and 72 and 318 and 73, such as those described above.

In another aspect, the variant alterations comprise or consist of substitutions at positions corresponding to positions 271 and 72 and 60 and 73, such as those described above.

In another aspect, the variant alterations comprise or consist of substitutions at positions corresponding to positions 271 and 77 and 145 and 318, such as those described above.

In another aspect, the variant alterations comprise or consist of substitutions at positions corresponding to positions 271 and 77 and 145 and 60, such as those described above.

In another aspect, the variant alterations comprise or consist of substitutions at positions corresponding to positions 271 and 77 and 145 and 73, such as those described above.

In another aspect, the variant alterations comprise or consist of substitutions at positions corresponding to positions 271 and 77 and 318 and 60, such as those described above.

In another aspect, the variant alterations comprise or consist of substitutions at positions corresponding to positions 271 and 77 and 318 and 73, such as those described above.

In another aspect, the variant alterations comprise or consist of substitutions at positions corresponding to positions 271 and 77 and 60 and 73, such as those described above.

In another aspect, the variant alterations comprise or consist of substitutions at positions corresponding to positions 271 and 145 and 318 and 60, such as those described above.

In another aspect, the variant alterations comprise or consist of substitutions at positions corresponding to positions 271 and 145 and 318 and 73, such as those described above.

In another aspect, the variant alterations comprise or consist of substitutions at positions corresponding to positions 271 and 145 and 60 and 73, such as those described above.

In another aspect, the variant alterations comprise or consist of substitutions at positions corresponding to positions 271 and 318 and 60 and 73, such as those described above.

In another aspect, the variant alterations comprise or consist of substitutions at positions corresponding to positions 72 and 77 and 145 and 318, such as those described above.

In another aspect, the variant alterations comprise or consist of substitutions at positions corresponding to positions 72 and 77 and 145 and 60, such as those described above.

In another aspect, the variant alterations comprise or consist of substitutions at positions corresponding to positions 72 and 77 and 145 and 73, such as those described above.

In another aspect, the variant alterations comprise or consist of substitutions at positions corresponding to positions 72 and 77 and 318 and 60, such as those described above.

In another aspect, the variant alterations comprise or consist of substitutions at positions corresponding to positions 72 and 77 and 318 and 73, such as those described above.

In another aspect, the variant alterations comprise or consist of substitutions at positions corresponding to positions 72 and 77 and 60 and 73, such as those described above.

In another aspect, the variant alterations comprise or consist of substitutions at positions corresponding to positions 72 and 145 and 318 and 60, such as those described above.

In another aspect, the variant alterations comprise or consist of substitutions at positions corresponding to positions 72 and 145 and 318 and 73, such as those described above.

In another aspect, the variant alterations comprise or consist of substitutions at positions corresponding to positions 72 and 145 and 60 and 73, such as those described above.

In another aspect, the variant alterations comprise or consist of substitutions at positions corresponding to positions 72 and 318 and 60 and 73, such as those described above.

In another aspect, the variant alterations comprise or consist of substitutions at positions corresponding to positions 77 and 145 and 318 and 60, such as those described above.

In another aspect, the variant alterations comprise or consist of substitutions at positions corresponding to positions 77 and 145 and 318 and 73, such as those described above.

In another aspect, the variant alterations comprise or consist of substitutions at positions corresponding to positions 77 and 145 and 60 and 73, such as those described above.

In another aspect, the variant alterations comprise or consist of substitutions at positions corresponding to positions 77 and 318 and 60 and 73, such as those described above.

In another aspect, the variant alterations comprise or consist of substitutions at positions corresponding to positions 145 and 318 and 60 and 73, such as those described above.

In another aspect, the variant alterations comprise or consist of substitutions at positions corresponding to positions 295 and 224 and 410 and 271 and 72, such as those described above.

In another aspect, the variant alterations comprise or consist of substitutions at positions corresponding to positions 295 and 224 and 410 and 271 and 77, such as those described above.

In another aspect, the variant alterations comprise or consist of substitutions at positions corresponding to positions 295 and 224 and 410 and 271 and 145, such as those described above.

In another aspect, the variant alterations comprise or consist of substitutions at positions corresponding to positions 295 and 224 and 410 and 271 and 318, such as those described above.

In another aspect, the variant alterations comprise or consist of substitutions at positions corresponding to positions 295 and 224 and 410 and 271 and 60, such as those described above.

In another aspect, the variant alterations comprise or consist of substitutions at positions corresponding to positions 295 and 224 and 410 and 271 and 73, such as those described above.

In another aspect, the variant alterations comprise or consist of substitutions at positions corresponding to positions 295 and 224 and 410 and 72 and 77, such as those described above.

In another aspect, the variant alterations comprise or consist of substitutions at positions corresponding to positions 295 and 224 and 410 and 72 and 145, such as those described above.

In another aspect, the variant alterations comprise or consist of substitutions at positions corresponding to positions 295 and 224 and 410 and 72 and 318, such as those described above.

In another aspect, the variant alterations comprise or consist of substitutions at positions corresponding to positions 295 and 224 and 410 and 72 and 60, such as those described above.

In another aspect, the variant alterations comprise or consist of substitutions at positions corresponding to positions 295 and 224 and 410 and 72 and 73, such as those described above.

In another aspect, the variant alterations comprise or consist of substitutions at positions corresponding to positions 295 and 224 and 410 and 77 and 145, such as those described above.

In another aspect, the variant alterations comprise or consist of substitutions at positions corresponding to positions 295 and 224 and 410 and 77 and 318, such as those described above.

In another aspect, the variant alterations comprise or consist of substitutions at positions corresponding to positions 295 and 224 and 410 and 77 and 60, such as those described above.

In another aspect, the variant alterations comprise or consist of substitutions at positions corresponding to positions 295 and 224 and 410 and 77 and 73, such as those described above.

In another aspect, the variant alterations comprise or consist of substitutions at positions corresponding to positions 295 and 224 and 410 and 145 and 318, such as those described above.

In another aspect, the variant alterations comprise or consist of substitutions at positions corresponding to positions 295 and 224 and 410 and 145 and 60, such as those described above.

In another aspect, the variant alterations comprise or consist of substitutions at positions corresponding to positions 295 and 224 and 410 and 145 and 73, such as those described above.

In another aspect, the variant alterations comprise or consist of substitutions at positions corresponding to positions 295 and 224 and 410 and 318 and 60, such as those described above.

In another aspect, the variant alterations comprise or consist of substitutions at positions corresponding to positions 295 and 224 and 410 and 318 and 73, such as those described above.

In another aspect, the variant alterations comprise or consist of substitutions at positions corresponding to positions 295 and 224 and 410 and 60 and 73, such as those described above.

In another aspect, the variant alterations comprise or consist of substitutions at positions corresponding to positions 295 and 224 and 271 and 72 and 77, such as those described above.

In another aspect, the variant alterations comprise or consist of substitutions at positions corresponding to positions 295 and 224 and 271 and 72 and 145, such as those described above.

In another aspect, the variant alterations comprise or consist of substitutions at positions corresponding to positions 295 and 224 and 271 and 72 and 318, such as those described above.

In another aspect, the variant alterations comprise or consist of substitutions at positions corresponding to positions 295 and 224 and 271 and 72 and 60, such as those described above.

In another aspect, the variant alterations comprise or consist of substitutions at positions corresponding to positions 295 and 224 and 271 and 72 and 73, such as those described above.

In another aspect, the variant alterations comprise or consist of substitutions at positions corresponding to positions 295 and 224 and 271 and 77 and 145, such as those described above.

In another aspect, the variant alterations comprise or consist of substitutions at positions corresponding to positions 295 and 224 and 271 and 77 and 318, such as those described above.

In another aspect, the variant alterations comprise or consist of substitutions at positions corresponding to positions 295 and 224 and 271 and 77 and 60, such as those described above.

In another aspect, the variant alterations comprise or consist of substitutions at positions corresponding to positions 295 and 224 and 271 and 77 and 73, such as those described above.

In another aspect, the variant alterations comprise or consist of substitutions at positions corresponding to positions 295 and 224 and 271 and 145 and 318, such as those described above.

In another aspect, the variant alterations comprise or consist of substitutions at positions corresponding to positions 295 and 224 and 271 and 145 and 60, such as those described above.

In another aspect, the variant alterations comprise or consist of substitutions at positions corresponding to positions 295 and 224 and 271 and 145 and 73, such as those described above.

In another aspect, the variant alterations comprise or consist of substitutions at positions corresponding to positions 295 and 224 and 271 and 318 and 60, such as those described above.

In another aspect, the variant alterations comprise or consist of substitutions at positions corresponding to positions 295 and 224 and 271 and 318 and 73, such as those described above.

In another aspect, the variant alterations comprise or consist of substitutions at positions corresponding to positions 295 and 224 and 271 and 60 and 73, such as those described above.

In another aspect, the variant alterations comprise or consist of substitutions at positions corresponding to positions 295 and 224 and 72 and 77 and 145, such as those described above.

In another aspect, the variant alterations comprise or consist of substitutions at positions corresponding to positions 295 and 224 and 72 and 77 and 318, such as those described above.

In another aspect, the variant alterations comprise or consist of substitutions at positions corresponding to positions 295 and 224 and 72 and 77 and 60, such as those described above.

In another aspect, the variant alterations comprise or consist of substitutions at positions corresponding to positions 295 and 224 and 72 and 77 and 73, such as those described above.

In another aspect, the variant alterations comprise or consist of substitutions at positions corresponding to positions 295 and 224 and 72 and 145 and 318, such as those described above.

In another aspect, the variant alterations comprise or consist of substitutions at positions corresponding to positions 295 and 224 and 72 and 145 and 60, such as those described above.

In another aspect, the variant alterations comprise or consist of substitutions at positions corresponding to positions 295 and 224 and 72 and 145 and 73, such as those described above.

In another aspect, the variant alterations comprise or consist of substitutions at positions corresponding to positions 295 and 224 and 72 and 318 and 60, such as those described above.

In another aspect, the variant alterations comprise or consist of substitutions at positions corresponding to positions 295 and 224 and 72 and 318 and 73, such as those described above.

In another aspect, the variant alterations comprise or consist of substitutions at positions corresponding to positions 295 and 224 and 72 and 60 and 73, such as those described above.

In another aspect, the variant alterations comprise or consist of substitutions at positions corresponding to positions 295 and 224 and 77 and 145 and 318, such as those described above.

In another aspect, the variant alterations comprise or consist of substitutions at positions corresponding to positions 295 and 224 and 77 and 145 and 60, such as those described above.

In another aspect, the variant alterations comprise or consist of substitutions at positions corresponding to positions 295 and 224 and 77 and 145 and 73, such as those described above.

In another aspect, the variant alterations comprise or consist of substitutions at positions corresponding to positions 295 and 224 and 77 and 318 and 60, such as those described above.

In another aspect, the variant alterations comprise or consist of substitutions at positions corresponding to positions 295 and 224 and 77 and 318 and 73, such as those described above.

In another aspect, the variant alterations comprise or consist of substitutions at positions corresponding to positions 295 and 224 and 77 and 60 and 73, such as those described above.

In another aspect, the variant alterations comprise or consist of substitutions at positions corresponding to positions 295 and 224 and 145 and 318 and 60, such as those described above.

In another aspect, the variant alterations comprise or consist of substitutions at positions corresponding to positions 295 and 224 and 145 and 318 and 73, such as those described above.

In another aspect, the variant alterations comprise or consist of substitutions at positions corresponding to positions 295 and 224 and 145 and 60 and 73, such as those described above.

In another aspect, the variant alterations comprise or consist of substitutions at positions corresponding to positions 295 and 224 and 318 and 60 and 73, such as those described above.

In another aspect, the variant alterations comprise or consist of substitutions at positions corresponding to positions 295 and 410 and 271 and 72 and 77, such as those described above.

In another aspect, the variant alterations comprise or consist of substitutions at positions corresponding to positions 295 and 410 and 271 and 72 and 145, such as those described above.

In another aspect, the variant alterations comprise or consist of substitutions at positions corresponding to positions 295 and 410 and 271 and 72 and 318, such as those described above.

In another aspect, the variant alterations comprise or consist of substitutions at positions corresponding to positions 295 and 410 and 271 and 72 and 60, such as those described above.

In another aspect, the variant alterations comprise or consist of substitutions at positions corresponding to positions 295 and 410 and 271 and 72 and 73, such as those described above.

In another aspect, the variant alterations comprise or consist of substitutions at positions corresponding to positions 295 and 410 and 271 and 77 and 145, such as those described above.

In another aspect, the variant alterations comprise or consist of substitutions at positions corresponding to positions 295 and 410 and 271 and 77 and 318, such as those described above.

In another aspect, the variant alterations comprise or consist of substitutions at positions corresponding to positions 295 and 410 and 271 and 77 and 60, such as those described above.

In another aspect, the variant alterations comprise or consist of substitutions at positions corresponding to positions 295 and 410 and 271 and 77 and 73, such as those described above.

In another aspect, the variant alterations comprise or consist of substitutions at positions corresponding to positions 295 and 410 and 271 and 145 and 318, such as those described above.

In another aspect, the variant alterations comprise or consist of substitutions at positions corresponding to positions 295 and 410 and 271 and 145 and 60, such as those described above.

In another aspect, the variant alterations comprise or consist of substitutions at positions corresponding to positions 295 and 410 and 271 and 145 and 73, such as those described above.

In another aspect, the variant alterations comprise or consist of substitutions at positions corresponding to positions 295 and 410 and 271 and 318 and 60, such as those described above.

In another aspect, the variant alterations comprise or consist of substitutions at positions corresponding to positions 295 and 410 and 271 and 318 and 73, such as those described above.

In another aspect, the variant alterations comprise or consist of substitutions at positions corresponding to positions 295 and 410 and 271 and 60 and 73, such as those described above.

In another aspect, the variant alterations comprise or consist of substitutions at positions corresponding to positions 295 and 410 and 72 and 77 and 145, such as those described above.

In another aspect, the variant alterations comprise or consist of substitutions at positions corresponding to positions 295 and 410 and 72 and 77 and 318, such as those described above.

In another aspect, the variant alterations comprise or consist of substitutions at positions corresponding to positions 295 and 410 and 72 and 77 and 60, such as those described above.

In another aspect, the variant alterations comprise or consist of substitutions at positions corresponding to positions 295 and 410 and 72 and 77 and 73, such as those described above.

In another aspect, the variant alterations comprise or consist of substitutions at positions corresponding to positions 295 and 410 and 72 and 145 and 318, such as those described above.

In another aspect, the variant alterations comprise or consist of substitutions at positions corresponding to positions 295 and 410 and 72 and 145 and 60, such as those described above.

In another aspect, the variant alterations comprise or consist of substitutions at positions corresponding to positions 295 and 410 and 72 and 145 and 73, such as those described above.

In another aspect, the variant alterations comprise or consist of substitutions at positions corresponding to positions 295 and 410 and 72 and 318 and 60, such as those described above.

In another aspect, the variant alterations comprise or consist of substitutions at positions corresponding to positions 295 and 410 and 72 and 318 and 73, such as those described above.

In another aspect, the variant alterations comprise or consist of substitutions at positions corresponding to positions 295 and 410 and 72 and 60 and 73, such as those described above.

In another aspect, the variant alterations comprise or consist of substitutions at positions corresponding to positions 295 and 410 and 77 and 145 and 318, such as those described above.

In another aspect, the variant alterations comprise or consist of substitutions at positions corresponding to positions 295 and 410 and 77 and 145 and 60, such as those described above.

In another aspect, the variant alterations comprise or consist of substitutions at positions corresponding to positions 295 and 410 and 77 and 145 and 73, such as those described above.

In another aspect, the variant alterations comprise or consist of substitutions at positions corresponding to positions 295 and 410 and 77 and 318 and 60, such as those described above.

In another aspect, the variant alterations comprise or consist of substitutions at positions corresponding to positions 295 and 410 and 77 and 318 and 73, such as those described above.

In another aspect, the variant alterations comprise or consist of substitutions at positions corresponding to positions 295 and 410 and 77 and 60 and 73, such as those described above.

In another aspect, the variant alterations comprise or consist of substitutions at positions corresponding to positions 295 and 410 and 145 and 318 and 60 In another aspect, the variant alterations comprise or consist of substitutions at positions corresponding to positions 295 and 410 and 145 and 318 and 73, such as those described above.

In another aspect, the variant alterations comprise or consist of substitutions at positions corresponding to positions 295 and 410 and 145 and 60 and 73, such as those described above.

In another aspect, the variant alterations comprise or consist of substitutions at positions corresponding to positions 295 and 410 and 318 and 60 and 73, such as those described above.

In another aspect, the variant alterations comprise or consist of substitutions at positions corresponding to positions 295 and 271 and 72 and 77 and 145, such as those described above.

In another aspect, the variant alterations comprise or consist of substitutions at positions corresponding to positions 295 and 271 and 72 and 77 and 318, such as those described above.

In another aspect, the variant alterations comprise or consist of substitutions at positions corresponding to positions 295 and 271 and 72 and 77 and 60, such as those described above.

In another aspect, the variant alterations comprise or consist of substitutions at positions corresponding to positions 295 and 271 and 72 and 77 and 73, such as those described above.

In another aspect, the variant alterations comprise or consist of substitutions at positions corresponding to positions 295 and 271 and 72 and 145 and 318, such as those described above.

In another aspect, the variant alterations comprise or consist of substitutions at positions corresponding to positions 295 and 271 and 72 and 145 and 60, such as those described above.

In another aspect, the variant alterations comprise or consist of substitutions at positions corresponding to positions 295 and 271 and 72 and 145 and 73, such as those described above.

In another aspect, the variant alterations comprise or consist of substitutions at positions corresponding to positions 295 and 271 and 72 and 318 and 60, such as those described above.

In another aspect, the variant alterations comprise or consist of substitutions at positions corresponding to positions 295 and 271 and 72 and 318 and 73, such as those described above.

In another aspect, the variant alterations comprise or consist of substitutions at positions corresponding to positions 295 and 271 and 72 and 60 and 73, such as those described above.

In another aspect, the variant alterations comprise or consist of substitutions at positions corresponding to positions 295 and 271 and 77 and 145 and 318, such as those described above.

In another aspect, the variant alterations comprise or consist of substitutions at positions corresponding to positions 295 and 271 and 77 and 145 and 60, such as those described above.

In another aspect, the variant alterations comprise or consist of substitutions at positions corresponding to positions 295 and 271 and 77 and 145 and 73, such as those described above.

In another aspect, the variant alterations comprise or consist of substitutions at positions corresponding to positions 295 and 271 and 77 and 318 and 60, such as those described above.

In another aspect, the variant alterations comprise or consist of substitutions at positions corresponding to positions 295 and 271 and 77 and 318 and 73, such as those described above.

In another aspect, the variant alterations comprise or consist of substitutions at positions corresponding to positions 295 and 271 and 77 and 60 and 73, such as those described above.

In another aspect, the variant alterations comprise or consist of substitutions at positions corresponding to positions 295 and 271 and 145 and 318 and 60, such as those described above.

In another aspect, the variant alterations comprise or consist of substitutions at positions corresponding to positions 295 and 271 and 145 and 318 and 73, such as those described above.

In another aspect, the variant alterations comprise or consist of substitutions at positions corresponding to positions 295 and 271 and 145 and 60 and 73, such as those described above.

In another aspect, the variant alterations comprise or consist of substitutions at positions corresponding to positions 295 and 271 and 318 and 60 and 73, such as those described above.

In another aspect, the variant alterations comprise or consist of substitutions at positions corresponding to positions 295 and 72 and 77 and 145 and 318, such as those described above.

In another aspect, the variant alterations comprise or consist of substitutions at positions corresponding to positions 295 and 72 and 77 and 145 and 60, such as those described above.

In another aspect, the variant alterations comprise or consist of substitutions at positions corresponding to positions 295 and 72 and 77 and 145 and 73, such as those described above.

In another aspect, the variant alterations comprise or consist of substitutions at positions corresponding to positions 295 and 72 and 77 and 318 and 60, such as those described above.

In another aspect, the variant alterations comprise or consist of substitutions at positions corresponding to positions 295 and 72 and 77 and 318 and 73, such as those described above.

In another aspect, the variant alterations comprise or consist of substitutions at positions corresponding to positions 295 and 72 and 77 and 60 and 73, such as those described above.

In another aspect, the variant alterations comprise or consist of substitutions at positions corresponding to positions 295 and 72 and 145 and 318 and 60, such as those described above.

In another aspect, the variant alterations comprise or consist of substitutions at positions corresponding to positions 295 and 72 and 145 and 318 and 73, such as those described above.

In another aspect, the variant alterations comprise or consist of substitutions at positions corresponding to positions 295 and 72 and 145 and 60 and 73, such as those described above.

In another aspect, the variant alterations comprise or consist of substitutions at positions corresponding to positions 295 and 72 and 318 and 60 and 73, such as those described above.

In another aspect, the variant alterations comprise or consist of substitutions at positions corresponding to positions 295 and 77 and 145 and 318 and 60, such as those described above.

In another aspect, the variant alterations comprise or consist of substitutions at positions corresponding to positions 295 and 77 and 145 and 318 and 73, such as those described above.

In another aspect, the variant alterations comprise or consist of substitutions at positions corresponding to positions 295 and 77 and 145 and 60 and 73, such as those described above.

In another aspect, the variant alterations comprise or consist of substitutions at positions corresponding to positions 295 and 77 and 318 and 60 and 73, such as those described above.

In another aspect, the variant alterations comprise or consist of substitutions at positions corresponding to positions 295 and 145 and 318 and 60 and 73, such as those described above.

In another aspect, the variant alterations comprise or consist of substitutions at positions corresponding to positions 224 and 410 and 271 and 72 and 77, such as those described above.

In another aspect, the variant alterations comprise or consist of substitutions at positions corresponding to positions 224 and 410 and 271 and 72 and 145, such as those described above.

In another aspect, the variant alterations comprise or consist of substitutions at positions corresponding to positions 224 and 410 and 271 and 72 and 318, such as those described above.

In another aspect, the variant alterations comprise or consist of substitutions at positions corresponding to positions 224 and 410 and 271 and 72 and 60, such as those described above.

In another aspect, the variant alterations comprise or consist of substitutions at positions corresponding to positions 224 and 410 and 271 and 72 and 73, such as those described above.

In another aspect, the variant alterations comprise or consist of substitutions at positions corresponding to positions 224 and 410 and 271 and 77 and 145, such as those described above.

In another aspect, the variant alterations comprise or consist of substitutions at positions corresponding to positions 224 and 410 and 271 and 77 and 318, such as those described above.

In another aspect, the variant alterations comprise or consist of substitutions at positions corresponding to positions 224 and 410 and 271 and 77 and 60, such as those described above.

In another aspect, the variant alterations comprise or consist of substitutions at positions corresponding to positions 224 and 410 and 271 and 77 and 73, such as those described above.

In another aspect, the variant alterations comprise or consist of substitutions at positions corresponding to positions 224 and 410 and 271 and 145 and 318, such as those described above.

In another aspect, the variant alterations comprise or consist of substitutions at positions corresponding to positions 224 and 410 and 271 and 145 and 60, such as those described above.

In another aspect, the variant alterations comprise or consist of substitutions at positions corresponding to positions 224 and 410 and 271 and 145 and 73, such as those described above.

In another aspect, the variant alterations comprise or consist of substitutions at positions corresponding to positions 224 and 410 and 271 and 318 and 60, such as those described above.

In another aspect, the variant alterations comprise or consist of substitutions at positions corresponding to positions 224 and 410 and 271 and 318 and 73, such as those described above.

In another aspect, the variant alterations comprise or consist of substitutions at positions corresponding to positions 224 and 410 and 271 and 60 and 73, such as those described above.

In another aspect, the variant alterations comprise or consist of substitutions at positions corresponding to positions 224 and 410 and 72 and 77 and 145, such as those described above.

In another aspect, the variant alterations comprise or consist of substitutions at positions corresponding to positions 224 and 410 and 72 and 77 and 318, such as those described above.

In another aspect, the variant alterations comprise or consist of substitutions at positions corresponding to positions 224 and 410 and 72 and 77 and 60, such as those described above.

In another aspect, the variant alterations comprise or consist of substitutions at positions corresponding to positions 224 and 410 and 72 and 77 and 73, such as those described above.

In another aspect, the variant alterations comprise or consist of substitutions at positions corresponding to positions 224 and 410 and 72 and 145 and 318, such as those described above.

In another aspect, the variant alterations comprise or consist of substitutions at positions corresponding to positions 224 and 410 and 72 and 145 and 60, such as those described above.

In another aspect, the variant alterations comprise or consist of substitutions at positions corresponding to positions 224 and 410 and 72 and 145 and 73, such as those described above.

In another aspect, the variant alterations comprise or consist of substitutions at positions corresponding to positions 224 and 410 and 72 and 318 and 60, such as those described above.

In another aspect, the variant alterations comprise or consist of substitutions at positions corresponding to positions 224 and 410 and 72 and 318 and 73, such as those described above.

In another aspect, the variant alterations comprise or consist of substitutions at positions corresponding to positions 224 and 410 and 72 and 60 and 73, such as those described above.

In another aspect, the variant alterations comprise or consist of substitutions at positions corresponding to positions 224 and 410 and 77 and 145 and 318, such as those described above.

In another aspect, the variant alterations comprise or consist of substitutions at positions corresponding to positions 224 and 410 and 77 and 145 and 60, such as those described above.

In another aspect, the variant alterations comprise or consist of substitutions at positions corresponding to positions 224 and 410 and 77 and 145 and 73, such as those described above.

In another aspect, the variant alterations comprise or consist of substitutions at positions corresponding to positions 224 and 410 and 77 and 318 and 60, such as those described above.

In another aspect, the variant alterations comprise or consist of substitutions at positions corresponding to positions 224 and 410 and 77 and 318 and 73, such as those described above.

In another aspect, the variant alterations comprise or consist of substitutions at positions corresponding to positions 224 and 410 and 77 and 60 and 73, such as those described above.

In another aspect, the variant alterations comprise or consist of substitutions at positions corresponding to positions 224 and 410 and 145 and 318 and 60, such as those described above.

In another aspect, the variant alterations comprise or consist of substitutions at positions corresponding to positions 224 and 410 and 145 and 318 and 73, such as those described above.

In another aspect, the variant alterations comprise or consist of substitutions at positions corresponding to positions 224 and 410 and 145 and 60 and 73, such as those described above.

In another aspect, the variant alterations comprise or consist of substitutions at positions corresponding to positions 224 and 410 and 318 and 60 and 73, such as those described above.

In another aspect, the variant alterations comprise or consist of substitutions at positions corresponding to positions 224 and 271 and 72 and 77 and 145, such as those described above.

In another aspect, the variant alterations comprise or consist of substitutions at positions corresponding to positions 224 and 271 and 72 and 77 and 318, such as those described above.

In another aspect, the variant alterations comprise or consist of substitutions at positions corresponding to positions 224 and 271 and 72 and 77 and 60, such as those described above.

In another aspect, the variant alterations comprise or consist of substitutions at positions corresponding to positions 224 and 271 and 72 and 77 and 73, such as those described above.

In another aspect, the variant alterations comprise or consist of substitutions at positions corresponding to positions 224 and 271 and 72 and 145 and 318, such as those described above.

In another aspect, the variant alterations comprise or consist of substitutions at positions corresponding to positions 224 and 271 and 72 and 145 and 60, such as those described above.

In another aspect, the variant alterations comprise or consist of substitutions at positions corresponding to positions 224 and 271 and 72 and 145 and 73, such as those described above.

In another aspect, the variant alterations comprise or consist of substitutions at positions corresponding to positions 224 and 271 and 72 and 318 and 60, such as those described above.

In another aspect, the variant alterations comprise or consist of substitutions at positions corresponding to positions 224 and 271 and 72 and 318 and 73, such as those described above.

In another aspect, the variant alterations comprise or consist of substitutions at positions corresponding to positions 224 and 271 and 72 and 60 and 73, such as those described above.

In another aspect, the variant alterations comprise or consist of substitutions at positions corresponding to positions 224 and 271 and 77 and 145 and 318, such as those described above.

In another aspect, the variant alterations comprise or consist of substitutions at positions corresponding to positions 224 and 271 and 77 and 145 and 60, such as those described above.

In another aspect, the variant alterations comprise or consist of substitutions at positions corresponding to positions 224 and 271 and 77 and 145 and 73, such as those described above.

In another aspect, the variant alterations comprise or consist of substitutions at positions corresponding to positions 224 and 271 and 77 and 318 and 60, such as those described above.

In another aspect, the variant alterations comprise or consist of substitutions at positions corresponding to positions 224 and 271 and 77 and 318 and 73, such as those described above.

In another aspect, the variant alterations comprise or consist of substitutions at positions corresponding to positions 224 and 271 and 77 and 60 and 73, such as those described above.

In another aspect, the variant alterations comprise or consist of substitutions at positions corresponding to positions 224 and 271 and 145 and 318 and 60, such as those described above.

In another aspect, the variant alterations comprise or consist of substitutions at positions corresponding to positions 224 and 271 and 145 and 318 and 73, such as those described above.

In another aspect, the variant alterations comprise or consist of substitutions at positions corresponding to positions 224 and 271 and 145 and 60 and 73, such as those described above.

In another aspect, the variant alterations comprise or consist of substitutions at positions corresponding to positions 224 and 271 and 318 and 60 and 73, such as those described above.

In another aspect, the variant alterations comprise or consist of substitutions at positions corresponding to positions 224 and 72 and 77 and 145 and 318, such as those described above.

In another aspect, the variant alterations comprise or consist of substitutions at positions corresponding to positions 224 and 72 and 77 and 145 and 60, such as those described above.

In another aspect, the variant alterations comprise or consist of substitutions at positions corresponding to positions 224 and 72 and 77 and 145 and 73, such as those described above.

In another aspect, the variant alterations comprise or consist of substitutions at positions corresponding to positions 224 and 72 and 77 and 318 and 60, such as those described above.

In another aspect, the variant alterations comprise or consist of substitutions at positions corresponding to positions 224 and 72 and 77 and 318 and 73, such as those described above.

In another aspect, the variant alterations comprise or consist of substitutions at positions corresponding to positions 224 and 72 and 77 and 60 and 73, such as those described above.

In another aspect, the variant alterations comprise or consist of substitutions at positions corresponding to positions 224 and 72 and 145 and 318 and 60, such as those described above.

In another aspect, the variant alterations comprise or consist of substitutions at positions corresponding to positions 224 and 72 and 145 and 318 and 73, such as those described above.

In another aspect, the variant alterations comprise or consist of substitutions at positions corresponding to positions 224 and 72 and 145 and 60 and 73, such as those described above.

In another aspect, the variant alterations comprise or consist of substitutions at positions corresponding to positions 224 and 72 and 318 and 60 and 73, such as those described above.

In another aspect, the variant alterations comprise or consist of substitutions at positions corresponding to positions 224 and 77 and 145 and 318 and 60, such as those described above.

In another aspect, the variant alterations comprise or consist of substitutions at positions corresponding to positions 224 and 77 and 145 and 318 and 73, such as those described above.

In another aspect, the variant alterations comprise or consist of substitutions at positions corresponding to positions 224 and 77 and 145 and 60 and 73, such as those described above.

In another aspect, the variant alterations comprise or consist of substitutions at positions corresponding to positions 224 and 77 and 318 and 60 and 73, such as those described above.

In another aspect, the variant alterations comprise or consist of substitutions at positions corresponding to positions 224 and 145 and 318 and 60 and 73, such as those described above.

In another aspect, the variant alterations comprise or consist of substitutions at positions corresponding to positions 410 and 271 and 72 and 77 and 145, such as those described above.

In another aspect, the variant alterations comprise or consist of substitutions at positions corresponding to positions 410 and 271 and 72 and 77 and 318, such as those described above.

In another aspect, the variant alterations comprise or consist of substitutions at positions corresponding to positions 410 and 271 and 72 and 77 and 60, such as those described above.

In another aspect, the variant alterations comprise or consist of substitutions at positions corresponding to positions 410 and 271 and 72 and 77 and 73, such as those described above.

In another aspect, the variant alterations comprise or consist of substitutions at positions corresponding to positions 410 and 271 and 72 and 145 and 318, such as those described above.

In another aspect, the variant alterations comprise or consist of substitutions at positions corresponding to positions 410 and 271 and 72 and 145 and 60, such as those described above.

In another aspect, the variant alterations comprise or consist of substitutions at positions corresponding to positions 410 and 271 and 72 and 145 and 73, such as those described above.

In another aspect, the variant alterations comprise or consist of substitutions at positions corresponding to positions 410 and 271 and 72 and 318 and 60, such as those described above.

In another aspect, the variant alterations comprise or consist of substitutions at positions corresponding to positions 410 and 271 and 72 and 318 and 73, such as those described above.

In another aspect, the variant alterations comprise or consist of substitutions at positions corresponding to positions 410 and 271 and 72 and 60 and 73, such as those described above.

In another aspect, the variant alterations comprise or consist of substitutions at positions corresponding to positions 410 and 271 and 77 and 145 and 318, such as those described above.

In another aspect, the variant alterations comprise or consist of substitutions at positions corresponding to positions 410 and 271 and 77 and 145 and 60, such as those described above.

In another aspect, the variant alterations comprise or consist of substitutions at positions corresponding to positions 410 and 271 and 77 and 145 and 73, such as those described above.

In another aspect, the variant alterations comprise or consist of substitutions at positions corresponding to positions 410 and 271 and 77 and 318 and 60, such as those described above.

In another aspect, the variant alterations comprise or consist of substitutions at positions corresponding to positions 410 and 271 and 77 and 318 and 73, such as those described above.

In another aspect, the variant alterations comprise or consist of substitutions at positions corresponding to positions 410 and 271 and 77 and 60 and 73, such as those described above.

In another aspect, the variant alterations comprise or consist of substitutions at positions corresponding to positions 410 and 271 and 145 and 318 and 60, such as those described above.

In another aspect, the variant alterations comprise or consist of substitutions at positions corresponding to positions 410 and 271 and 145 and 318 and 73, such as those described above.

In another aspect, the variant alterations comprise or consist of substitutions at positions corresponding to positions 410 and 271 and 145 and 60 and 73, such as those described above.

In another aspect, the variant alterations comprise or consist of substitutions at positions corresponding to positions 410 and 271 and 318 and 60 and 73, such as those described above.

In another aspect, the variant alterations comprise or consist of substitutions at positions corresponding to positions 410 and 72 and 77 and 145 and 318, such as those described above.

In another aspect, the variant alterations comprise or consist of substitutions at positions corresponding to positions 410 and 72 and 77 and 145 and 60, such as those described above.

In another aspect, the variant alterations comprise or consist of substitutions at positions corresponding to positions 410 and 72 and 77 and 145 and 73, such as those described above.

In another aspect, the variant alterations comprise or consist of substitutions at positions corresponding to positions 410 and 72 and 77 and 318 and 60, such as those described above.

In another aspect, the variant alterations comprise or consist of substitutions at positions corresponding to positions 410 and 72 and 77 and 318 and 73, such as those described above.

In another aspect, the variant alterations comprise or consist of substitutions at positions corresponding to positions 410 and 72 and 77 and 60 and 73, such as those described above.

In another aspect, the variant alterations comprise or consist of substitutions at positions corresponding to positions 410 and 72 and 145 and 318 and 60, such as those described above.

In another aspect, the variant alterations comprise or consist of substitutions at positions corresponding to positions 410 and 72 and 145 and 318 and 73, such as those described above.

In another aspect, the variant alterations comprise or consist of substitutions at positions corresponding to positions 410 and 72 and 145 and 60 and 73, such as those described above.

In another aspect, the variant alterations comprise or consist of substitutions at positions corresponding to positions 410 and 72 and 318 and 60 and 73, such as those described above.

In another aspect, the variant alterations comprise or consist of substitutions at positions corresponding to positions 410 and 77 and 145 and 318 and 60, such as those described above.

In another aspect, the variant alterations comprise or consist of substitutions at positions corresponding to positions 410 and 77 and 145 and 318 and 73, such as those described above.

In another aspect, the variant alterations comprise or consist of substitutions at positions corresponding to positions 410 and 77 and 145 and 60 and 73, such as those described above.

In another aspect, the variant alterations comprise or consist of substitutions at positions corresponding to positions 410 and 77 and 318 and 60 and 73, such as those described above.

In another aspect, the variant alterations comprise or consist of substitutions at positions corresponding to positions 410 and 145 and 318 and 60 and 73, such as those described above.

In another aspect, the variant alterations comprise or consist of substitutions at positions corresponding to positions 271 and 72 and 77 and 145 and 318, such as those described above.

In another aspect, the variant alterations comprise or consist of substitutions at positions corresponding to positions 271 and 72 and 77 and 145 and 60, such as those described above.

In another aspect, the variant alterations comprise or consist of substitutions at positions corresponding to positions 271 and 72 and 77 and 145 and 73, such as those described above.

In another aspect, the variant alterations comprise or consist of substitutions at positions corresponding to positions 271 and 72 and 77 and 318 and 60, such as those described above.

In another aspect, the variant alterations comprise or consist of substitutions at positions corresponding to positions 271 and 72 and 77 and 318 and 73, such as those described above.

In another aspect, the variant alterations comprise or consist of substitutions at positions corresponding to positions 271 and 72 and 77 and 60 and 73, such as those described above.

In another aspect, the variant alterations comprise or consist of substitutions at positions corresponding to positions 271 and 72 and 145 and 318 and 60, such as those described above.

In another aspect, the variant alterations comprise or consist of substitutions at positions corresponding to positions 271 and 72 and 145 and 318 and 73, such as those described above.

In another aspect, the variant alterations comprise or consist of substitutions at positions corresponding to positions 271 and 72 and 145 and 60 and 73, such as those described above.

In another aspect, the variant alterations comprise or consist of substitutions at positions corresponding to positions 271 and 72 and 318 and 60 and 73, such as those described above.

In another aspect, the variant alterations comprise or consist of substitutions at positions corresponding to positions 271 and 77 and 145 and 318 and 60, such as those described above.

In another aspect, the variant alterations comprise or consist of substitutions at positions corresponding to positions 271 and 77 and 145 and 318 and 73, such as those described above.

In another aspect, the variant alterations comprise or consist of substitutions at positions corresponding to positions 271 and 77 and 145 and 60 and 73, such as those described above.

In another aspect, the variant alterations comprise or consist of substitutions at positions corresponding to positions 271 and 77 and 318 and 60 and 73, such as those described above.

In another aspect, the variant alterations comprise or consist of substitutions at positions corresponding to positions 271 and 145 and 318 and 60 and 73, such as those described above.

In another aspect, the variant alterations comprise or consist of substitutions at positions corresponding to positions 72 and 77 and 145 and 318 and 60, such as those described above.

In another aspect, the variant alterations comprise or consist of substitutions at positions corresponding to positions 72 and 77 and 145 and 318 and 73, such as those described above.

In another aspect, the variant alterations comprise or consist of substitutions at positions corresponding to positions 72 and 77 and 145 and 60 and 73, such as those described above.

In another aspect, the variant alterations comprise or consist of substitutions at positions corresponding to positions 72 and 77 and 318 and 60 and 73, such as those described above.

In another aspect, the variant alterations comprise or consist of substitutions at positions corresponding to positions 72 and 145 and 318 and 60 and 73, such as those described above.

In another aspect, the variant alterations comprise or consist of substitutions at positions corresponding to positions 77 and 145 and 318 and 60 and 73, such as those described above.

In another aspect, the variant alterations comprise or consist of substitutions at positions corresponding to positions 295 and 224 and 410 and 271 and 72 and 77, such as those described above.

In another aspect, the variant alterations comprise or consist of substitutions at positions corresponding to positions 295 and 224 and 410 and 271 and 72 and 145, such as those described above.

In another aspect, the variant alterations comprise or consist of substitutions at positions corresponding to positions 295 and 224 and 410 and 271 and 72 and 318, such as those described above.

In another aspect, the variant alterations comprise or consist of substitutions at positions corresponding to positions 295 and 224 and 410 and 271 and 72 and 60, such as those described above.

In another aspect, the variant alterations comprise or consist of substitutions at positions corresponding to positions 295 and 224 and 410 and 271 and 72 and 73, such as those described above.

In another aspect, the variant alterations comprise or consist of substitutions at positions corresponding to positions 295 and 224 and 410 and 271 and 77 and 145, such as those described above.

In another aspect, the variant alterations comprise or consist of substitutions at positions corresponding to positions 295 and 224 and 410 and 271 and 77 and 318, such as those described above.

In another aspect, the variant alterations comprise or consist of substitutions at positions corresponding to positions 295 and 224 and 410 and 271 and 77 and 60, such as those described above.

In another aspect, the variant alterations comprise or consist of substitutions at positions corresponding to positions 295 and 224 and 410 and 271 and 77 and 73, such as those described above.

In another aspect, the variant alterations comprise or consist of substitutions at positions corresponding to positions 295 and 224 and 410 and 271 and 145 and 318, such as those described above.

In another aspect, the variant alterations comprise or consist of substitutions at positions corresponding to positions 295 and 224 and 410 and 271 and 145 and 60, such as those described above.

In another aspect, the variant alterations comprise or consist of substitutions at positions corresponding to positions 295 and 224 and 410 and 271 and 145 and 73, such as those described above.

In another aspect, the variant alterations comprise or consist of substitutions at positions corresponding to positions 295 and 224 and 410 and 271 and 318 and 60, such as those described above.

In another aspect, the variant alterations comprise or consist of substitutions at positions corresponding to positions 295 and 224 and 410 and 271 and 318 and 73, such as those described above.

In another aspect, the variant alterations comprise or consist of substitutions at positions corresponding to positions 295 and 224 and 410 and 271 and 60 and 73, such as those described above.

In another aspect, the variant alterations comprise or consist of substitutions at positions corresponding to positions 295 and 224 and 410 and 72 and 77 and 145, such as those described above.

In another aspect, the variant alterations comprise or consist of substitutions at positions corresponding to positions 295 and 224 and 410 and 72 and 77 and 318, such as those described above.

In another aspect, the variant alterations comprise or consist of substitutions at positions corresponding to positions 295 and 224 and 410 and 72 and 77 and 60, such as those described above.

In another aspect, the variant alterations comprise or consist of substitutions at positions corresponding to positions 295 and 224 and 410 and 72 and 77 and 73, such as those described above.

In another aspect, the variant alterations comprise or consist of substitutions at positions corresponding to positions 295 and 224 and 410 and 72 and 145 and 318, such as those described above.

In another aspect, the variant alterations comprise or consist of substitutions at positions corresponding to positions 295 and 224 and 410 and 72 and 145 and 60, such as those described above.

In another aspect, the variant alterations comprise or consist of substitutions at positions corresponding to positions 295 and 224 and 410 and 72 and 145 and 73, such as those described above.

In another aspect, the variant alterations comprise or consist of substitutions at positions corresponding to positions 295 and 224 and 410 and 72 and 318 and 60, such as those described above.

In another aspect, the variant alterations comprise or consist of substitutions at positions corresponding to positions 295 and 224 and 410 and 72 and 318 and 73, such as those described above.

In another aspect, the variant alterations comprise or consist of substitutions at positions corresponding to positions 295 and 224 and 410 and 72 and 60 and 73, such as those described above.

In another aspect, the variant alterations comprise or consist of substitutions at positions corresponding to positions 295 and 224 and 410 and 77 and 145 and 318, such as those described above.

In another aspect, the variant alterations comprise or consist of substitutions at positions corresponding to positions 295 and 224 and 410 and 77 and 145 and 60, such as those described above.

In another aspect, the variant alterations comprise or consist of substitutions at positions corresponding to positions 295 and 224 and 410 and 77 and 145 and 73, such as those described above.

In another aspect, the variant alterations comprise or consist of substitutions at positions corresponding to positions 295 and 224 and 410 and 77 and 318 and 60, such as those described above.

In another aspect, the variant alterations comprise or consist of substitutions at positions corresponding to positions 295 and 224 and 410 and 77 and 318 and 73, such as those described above.

In another aspect, the variant alterations comprise or consist of substitutions at positions corresponding to positions 295 and 224 and 410 and 77 and 60 and 73, such as those described above.

In another aspect, the variant alterations comprise or consist of substitutions at positions corresponding to positions 295 and 224 and 410 and 145 and 318 and 60, such as those described above.

In another aspect, the variant alterations comprise or consist of substitutions at positions corresponding to positions 295 and 224 and 410 and 145 and 318 and 73, such as those described above.

In another aspect, the variant alterations comprise or consist of substitutions at positions corresponding to positions 295 and 224 and 410 and 145 and 60 and 73, such as those described above.

In another aspect, the variant alterations comprise or consist of substitutions at positions corresponding to positions 295 and 224 and 410 and 318 and 60 and 73, such as those described above.

In another aspect, the variant alterations comprise or consist of substitutions at positions corresponding to positions 295 and 224 and 271 and 72 and 77 and 145, such as those described above.

In another aspect, the variant alterations comprise or consist of substitutions at positions corresponding to positions 295 and 224 and 271 and 72 and 77 and 318, such as those described above.

In another aspect, the variant alterations comprise or consist of substitutions at positions corresponding to positions 295 and 224 and 271 and 72 and 77 and 60, such as those described above.

In another aspect, the variant alterations comprise or consist of substitutions at positions corresponding to positions 295 and 224 and 271 and 72 and 77 and 73, such as those described above.

In another aspect, the variant alterations comprise or consist of substitutions at positions corresponding to positions 295 and 224 and 271 and 72 and 145 and 318, such as those described above.

In another aspect, the variant alterations comprise or consist of substitutions at positions corresponding to positions 295 and 224 and 271 and 72 and 145 and 60, such as those described above.

In another aspect, the variant alterations comprise or consist of substitutions at positions corresponding to positions 295 and 224 and 271 and 72 and 145 and 73, such as those described above.

In another aspect, the variant alterations comprise or consist of substitutions at positions corresponding to positions 295 and 224 and 271 and 72 and 318 and 60, such as those described above.

In another aspect, the variant alterations comprise or consist of substitutions at positions corresponding to positions 295 and 224 and 271 and 72 and 318 and 73, such as those described above.

In another aspect, the variant alterations comprise or consist of substitutions at positions corresponding to positions 295 and 224 and 271 and 72 and 60 and 73, such as those described above.

In another aspect, the variant alterations comprise or consist of substitutions at positions corresponding to positions 295 and 224 and 271 and 77 and 145 and 318, such as those described above.

In another aspect, the variant alterations comprise or consist of substitutions at positions corresponding to positions 295 and 224 and 271 and 77 and 145 and 60, such as those described above.

In another aspect, the variant alterations comprise or consist of substitutions at positions corresponding to positions 295 and 224 and 271 and 77 and 145 and 73, such as those described above.

In another aspect, the variant alterations comprise or consist of substitutions at positions corresponding to positions 295 and 224 and 271 and 77 and 318 and 60, such as those described above.

In another aspect, the variant alterations comprise or consist of substitutions at positions corresponding to positions 295 and 224 and 271 and 77 and 318 and 73, such as those described above.

In another aspect, the variant alterations comprise or consist of substitutions at positions corresponding to positions 295 and 224 and 271 and 77 and 60 and 73, such as those described above.

In another aspect, the variant alterations comprise or consist of substitutions at positions corresponding to positions 295 and 224 and 271 and 145 and 318 and 60, such as those described above.

In another aspect, the variant alterations comprise or consist of substitutions at positions corresponding to positions 295 and 224 and 271 and 145 and 318 and 73, such as those described above.

In another aspect, the variant alterations comprise or consist of substitutions at positions corresponding to positions 295 and 224 and 271 and 145 and 60 and 73, such as those described above.

In another aspect, the variant alterations comprise or consist of substitutions at positions corresponding to positions 295 and 224 and 271 and 318 and 60 and 73, such as those described above.

In another aspect, the variant alterations comprise or consist of substitutions at positions corresponding to positions 295 and 224 and 72 and 77 and 145 and 318, such as those described above.

In another aspect, the variant alterations comprise or consist of substitutions at positions corresponding to positions 295 and 224 and 72 and 77 and 145 and 60, such as those described above.

In another aspect, the variant alterations comprise or consist of substitutions at positions corresponding to positions 295 and 224 and 72 and 77 and 145 and 73, such as those described above.

In another aspect, the variant alterations comprise or consist of substitutions at positions corresponding to positions 295 and 224 and 72 and 77 and 318 and 60, such as those described above.

In another aspect, the variant alterations comprise or consist of substitutions at positions corresponding to positions 295 and 224 and 72 and 77 and 318 and 73, such as those described above.

In another aspect, the variant alterations comprise or consist of substitutions at positions corresponding to positions 295 and 224 and 72 and 77 and 60 and 73, such as those described above.

In another aspect, the variant alterations comprise or consist of substitutions at positions corresponding to positions 295 and 224 and 72 and 145 and 318 and 60, such as those described above.

In another aspect, the variant alterations comprise or consist of substitutions at positions corresponding to positions 295 and 224 and 72 and 145 and 318 and 73, such as those described above.

In another aspect, the variant alterations comprise or consist of substitutions at positions corresponding to positions 295 and 224 and 72 and 145 and 60 and 73, such as those described above.

In another aspect, the variant alterations comprise or consist of substitutions at positions corresponding to positions 295 and 224 and 72 and 318 and 60 and 73, such as those described above.

In another aspect, the variant alterations comprise or consist of substitutions at positions corresponding to positions 295 and 224 and 77 and 145 and 318 and 60, such as those described above.

In another aspect, the variant alterations comprise or consist of substitutions at positions corresponding to positions 295 and 224 and 77 and 145 and 318 and 73, such as those described above.

In another aspect, the variant alterations comprise or consist of substitutions at positions corresponding to positions 295 and 224 and 77 and 145 and 60 and 73, such as those described above.

In another aspect, the variant alterations comprise or consist of substitutions at positions corresponding to positions 295 and 224 and 77 and 318 and 60 and 73, such as those described above.

In another aspect, the variant alterations comprise or consist of substitutions at positions corresponding to positions 295 and 224 and 145 and 318 and 60 and 73, such as those described above.

In another aspect, the variant alterations comprise or consist of substitutions at positions corresponding to positions 295 and 410 and 271 and 72 and 77 and 145, such as those described above.

In another aspect, the variant alterations comprise or consist of substitutions at positions corresponding to positions 295 and 410 and 271 and 72 and 77 and 318, such as those described above.

In another aspect, the variant alterations comprise or consist of substitutions at positions corresponding to positions 295 and 410 and 271 and 72 and 77 and 60, such as those described above.

In another aspect, the variant alterations comprise or consist of substitutions at positions corresponding to positions 295 and 410 and 271 and 72 and 77 and 73, such as those described above.

In another aspect, the variant alterations comprise or consist of substitutions at positions corresponding to positions 295 and 410 and 271 and 72 and 145 and 318, such as those described above.

In another aspect, the variant alterations comprise or consist of substitutions at positions corresponding to positions 295 and 410 and 271 and 72 and 145 and 60, such as those described above.

In another aspect, the variant alterations comprise or consist of substitutions at positions corresponding to positions 295 and 410 and 271 and 72 and 145 and 73, such as those described above.

In another aspect, the variant alterations comprise or consist of substitutions at positions corresponding to positions 295 and 410 and 271 and 72 and 318 and 60, such as those described above.

In another aspect, the variant alterations comprise or consist of substitutions at positions corresponding to positions 295 and 410 and 271 and 72 and 318 and 73, such as those described above.

In another aspect, the variant alterations comprise or consist of substitutions at positions corresponding to positions 295 and 410 and 271 and 72 and 60 and 73, such as those described above.

In another aspect, the variant alterations comprise or consist of substitutions at positions corresponding to positions 295 and 410 and 271 and 77 and 145 and 318, such as those described above.

In another aspect, the variant alterations comprise or consist of substitutions at positions corresponding to positions 295 and 410 and 271 and 77 and 145 and 60, such as those described above.

In another aspect, the variant alterations comprise or consist of substitutions at positions corresponding to positions 295 and 410 and 271 and 77 and 145 and 73, such as those described above.

In another aspect, the variant alterations comprise or consist of substitutions at positions corresponding to positions 295 and 410 and 271 and 77 and 318 and 60, such as those described above.

In another aspect, the variant alterations comprise or consist of substitutions at positions corresponding to positions 295 and 410 and 271 and 77 and 318 and 73, such as those described above.

In another aspect, the variant alterations comprise or consist of substitutions at positions corresponding to positions 295 and 410 and 271 and 77 and 60 and 73, such as those described above.

In another aspect, the variant alterations comprise or consist of substitutions at positions corresponding to positions 295 and 410 and 271 and 145 and 318 and 60, such as those described above.

In another aspect, the variant alterations comprise or consist of substitutions at positions corresponding to positions 295 and 410 and 271 and 145 and 318 and 73, such as those described above.

In another aspect, the variant alterations comprise or consist of substitutions at positions corresponding to positions 295 and 410 and 271 and 145 and 60 and 73, such as those described above.

In another aspect, the variant alterations comprise or consist of substitutions at positions corresponding to positions 295 and 410 and 271 and 318 and 60 and 73, such as those described above.

In another aspect, the variant alterations comprise or consist of substitutions at positions corresponding to positions 295 and 410 and 72 and 77 and 145 and 318, such as those described above.

In another aspect, the variant alterations comprise or consist of substitutions at positions corresponding to positions 295 and 410 and 72 and 77 and 145 and 60, such as those described above.

In another aspect, the variant alterations comprise or consist of substitutions at positions corresponding to positions 295 and 410 and 72 and 77 and 145 and 73, such as those described above.

In another aspect, the variant alterations comprise or consist of substitutions at positions corresponding to positions 295 and 410 and 72 and 77 and 318 and 60, such as those described above.

In another aspect, the variant alterations comprise or consist of substitutions at positions corresponding to positions 295 and 410 and 72 and 77 and 318 and 73, such as those described above.

In another aspect, the variant alterations comprise or consist of substitutions at positions corresponding to positions 295 and 410 and 72 and 77 and 60 and 73, such as those described above.

In another aspect, the variant alterations comprise or consist of substitutions at positions corresponding to positions 295 and 410 and 72 and 145 and 318 and 60, such as those described above.

In another aspect, the variant alterations comprise or consist of substitutions at positions corresponding to positions 295 and 410 and 72 and 145 and 318 and 73, such as those described above.

In another aspect, the variant alterations comprise or consist of substitutions at positions corresponding to positions 295 and 410 and 72 and 145 and 60 and 73, such as those described above.

In another aspect, the variant alterations comprise or consist of substitutions at positions corresponding to positions 295 and 410 and 72 and 318 and 60 and 73, such as those described above.

In another aspect, the variant alterations comprise or consist of substitutions at positions corresponding to positions 295 and 410 and 77 and 145 and 318 and 60, such as those described above.

In another aspect, the variant alterations comprise or consist of substitutions at positions corresponding to positions 295 and 410 and 77 and 145 and 318 and 73, such as those described above.

In another aspect, the variant alterations comprise or consist of substitutions at positions corresponding to positions 295 and 410 and 77 and 145 and 60 and 73, such as those described above.

In another aspect, the variant alterations comprise or consist of substitutions at positions corresponding to positions 295 and 410 and 77 and 318 and 60 and 73, such as those described above.

In another aspect, the variant alterations comprise or consist of substitutions at positions corresponding to positions 295 and 410 and 145 and 318 and 60 and 73, such as those described above.

In another aspect, the variant alterations comprise or consist of substitutions at positions corresponding to positions 295 and 271 and 72 and 77 and 145 and 318, such as those described above.

In another aspect, the variant alterations comprise or consist of substitutions at positions corresponding to positions 295 and 271 and 72 and 77 and 145 and 60, such as those described above.

In another aspect, the variant alterations comprise or consist of substitutions at positions corresponding to positions 295 and 271 and 72 and 77 and 145 and 73, such as those described above.

In another aspect, the variant alterations comprise or consist of substitutions at positions corresponding to positions 295 and 271 and 72 and 77 and 318 and 60, such as those described above.

In another aspect, the variant alterations comprise or consist of substitutions at positions corresponding to positions 295 and 271 and 72 and 77 and 318 and 73, such as those described above.

In another aspect, the variant alterations comprise or consist of substitutions at positions corresponding to positions 295 and 271 and 72 and 77 and 60 and 73, such as those described above.

In another aspect, the variant alterations comprise or consist of substitutions at positions corresponding to positions 295 and 271 and 72 and 145 and 318 and 60, such as those described above.

In another aspect, the variant alterations comprise or consist of substitutions at positions corresponding to positions 295 and 271 and 72 and 145 and 318 and 73, such as those described above.

In another aspect, the variant alterations comprise or consist of substitutions at positions corresponding to positions 295 and 271 and 72 and 145 and 60 and 73, such as those described above.

In another aspect, the variant alterations comprise or consist of substitutions at positions corresponding to positions 295 and 271 and 72 and 318 and 60 and 73, such as those described above.

In another aspect, the variant alterations comprise or consist of substitutions at positions corresponding to positions 295 and 271 and 77 and 145 and 318 and 60, such as those described above.

In another aspect, the variant alterations comprise or consist of substitutions at positions corresponding to positions 295 and 271 and 77 and 145 and 318 and 73, such as those described above.

In another aspect, the variant alterations comprise or consist of substitutions at positions corresponding to positions 295 and 271 and 77 and 145 and 60 and 73, such as those described above.

In another aspect, the variant alterations comprise or consist of substitutions at positions corresponding to positions 295 and 271 and 77 and 318 and 60 and 73, such as those described above.

In another aspect, the variant alterations comprise or consist of substitutions at positions corresponding to positions 295 and 271 and 145 and 318 and 60 and 73, such as those described above.

In another aspect, the variant alterations comprise or consist of substitutions at positions corresponding to positions 295 and 72 and 77 and 145 and 318 and 60, such as those described above.

In another aspect, the variant alterations comprise or consist of substitutions at positions corresponding to positions 295 and 72 and 77 and 145 and 318 and 73, such as those described above.

In another aspect, the variant alterations comprise or consist of substitutions at positions corresponding to positions 295 and 72 and 77 and 145 and 60 and 73, such as those described above.

In another aspect, the variant alterations comprise or consist of substitutions at positions corresponding to positions 295 and 72 and 77 and 318 and 60 and 73, such as those described above.

In another aspect, the variant alterations comprise or consist of substitutions at positions corresponding to positions 295 and 72 and 145 and 318 and 60 and 73, such as those described above.

In another aspect, the variant alterations comprise or consist of substitutions at positions corresponding to positions 295 and 77 and 145 and 318 and 60 and 73, such as those described above.

In another aspect, the variant alterations comprise or consist of substitutions at positions corresponding to positions 224 and 410 and 271 and 72 and 77 and 145, such as those described above.

In another aspect, the variant alterations comprise or consist of substitutions at positions corresponding to positions 224 and 410 and 271 and 72 and 77 and 318, such as those described above.

In another aspect, the variant alterations comprise or consist of substitutions at positions corresponding to positions 224 and 410 and 271 and 72 and 77 and 60, such as those described above.

In another aspect, the variant alterations comprise or consist of substitutions at positions corresponding to positions 224 and 410 and 271 and 72 and 77 and 73, such as those described above.

In another aspect, the variant alterations comprise or consist of substitutions at positions corresponding to positions 224 and 410 and 271 and 72 and 145 and 318, such as those described above.

In another aspect, the variant alterations comprise or consist of substitutions at positions corresponding to positions 224 and 410 and 271 and 72 and 145 and 60, such as those described above.

In another aspect, the variant alterations comprise or consist of substitutions at positions corresponding to positions 224 and 410 and 271 and 72 and 145 and 73, such as those described above.

In another aspect, the variant alterations comprise or consist of substitutions at positions corresponding to positions 224 and 410 and 271 and 72 and 318 and 60, such as those described above.

In another aspect, the variant alterations comprise or consist of substitutions at positions corresponding to positions 224 and 410 and 271 and 72 and 318 and 73, such as those described above.

In another aspect, the variant alterations comprise or consist of substitutions at positions corresponding to positions 224 and 410 and 271 and 72 and 60 and 73, such as those described above.

In another aspect, the variant alterations comprise or consist of substitutions at positions corresponding to positions 224 and 410 and 271 and 77 and 145 and 318, such as those described above.

In another aspect, the variant alterations comprise or consist of substitutions at positions corresponding to positions 224 and 410 and 271 and 77 and 145 and 60, such as those described above.

In another aspect, the variant alterations comprise or consist of substitutions at positions corresponding to positions 224 and 410 and 271 and 77 and 145 and 73, such as those described above.

In another aspect, the variant alterations comprise or consist of substitutions at positions corresponding to positions 224 and 410 and 271 and 77 and 318 and 60, such as those described above.

In another aspect, the variant alterations comprise or consist of substitutions at positions corresponding to positions 224 and 410 and 271 and 77 and 318 and 73, such as those described above.

In another aspect, the variant alterations comprise or consist of substitutions at positions corresponding to positions 224 and 410 and 271 and 77 and 60 and 73, such as those described above.

In another aspect, the variant alterations comprise or consist of substitutions at positions corresponding to positions 224 and 410 and 271 and 145 and 318 and 60, such as those described above.

In another aspect, the variant alterations comprise or consist of substitutions at positions corresponding to positions 224 and 410 and 271 and 145 and 318 and 73, such as those described above.

In another aspect, the variant alterations comprise or consist of substitutions at positions corresponding to positions 224 and 410 and 271 and 145 and 60 and 73, such as those described above.

In another aspect, the variant alterations comprise or consist of substitutions at positions corresponding to positions 224 and 410 and 271 and 318 and 60 and 73, such as those described above.

In another aspect, the variant alterations comprise or consist of substitutions at positions corresponding to positions 224 and 410 and 72 and 77 and 145 and 318, such as those described above.

In another aspect, the variant alterations comprise or consist of substitutions at positions corresponding to positions 224 and 410 and 72 and 77 and 145 and 60, such as those described above.

In another aspect, the variant alterations comprise or consist of substitutions at positions corresponding to positions 224 and 410 and 72 and 77 and 145 and 73, such as those described above.

In another aspect, the variant alterations comprise or consist of substitutions at positions corresponding to positions 224 and 410 and 72 and 77 and 318 and 60, such as those described above.

In another aspect, the variant alterations comprise or consist of substitutions at positions corresponding to positions 224 and 410 and 72 and 77 and 318 and 73, such as those described above.

In another aspect, the variant alterations comprise or consist of substitutions at positions corresponding to positions 224 and 410 and 72 and 77 and 60 and 73, such as those described above.

In another aspect, the variant alterations comprise or consist of substitutions at positions corresponding to positions 224 and 410 and 72 and 145 and 318 and 60, such as those described above.

In another aspect, the variant alterations comprise or consist of substitutions at positions corresponding to positions 224 and 410 and 72 and 145 and 318 and 73, such as those described above.

In another aspect, the variant alterations comprise or consist of substitutions at positions corresponding to positions 224 and 410 and 72 and 145 and 60 and 73, such as those described above.

In another aspect, the variant alterations comprise or consist of substitutions at positions corresponding to positions 224 and 410 and 72 and 318 and 60 and 73, such as those described above.

In another aspect, the variant alterations comprise or consist of substitutions at positions corresponding to positions 224 and 410 and 77 and 145 and 318 and 60, such as those described above.

In another aspect, the variant alterations comprise or consist of substitutions at positions corresponding to positions 224 and 410 and 77 and 145 and 318 and 73, such as those described above.

In another aspect, the variant alterations comprise or consist of substitutions at positions corresponding to positions 224 and 410 and 77 and 145 and 60 and 73, such as those described above.

In another aspect, the variant alterations comprise or consist of substitutions at positions corresponding to positions 224 and 410 and 77 and 318 and 60 and 73, such as those described above.

In another aspect, the variant alterations comprise or consist of substitutions at positions corresponding to positions 224 and 410 and 145 and 318 and 60 and 73, such as those described above.

In another aspect, the variant alterations comprise or consist of substitutions at positions corresponding to positions 224 and 271 and 72 and 77 and 145 and 318, such as those described above.

In another aspect, the variant alterations comprise or consist of substitutions at positions corresponding to positions 224 and 271 and 72 and 77 and 145 and 60, such as those described above.

In another aspect, the variant alterations comprise or consist of substitutions at positions corresponding to positions 224 and 271 and 72 and 77 and 145 and 73, such as those described above.

In another aspect, the variant alterations comprise or consist of substitutions at positions corresponding to positions 224 and 271 and 72 and 77 and 318 and 60, such as those described above.

In another aspect, the variant alterations comprise or consist of substitutions at positions corresponding to positions 224 and 271 and 72 and 77 and 318 and 73, such as those described above.

In another aspect, the variant alterations comprise or consist of substitutions at positions corresponding to positions 224 and 271 and 72 and 77 and 60 and 73, such as those described above.

In another aspect, the variant alterations comprise or consist of substitutions at positions corresponding to positions 224 and 271 and 72 and 145 and 318 and 60, such as those described above.

In another aspect, the variant alterations comprise or consist of substitutions at positions corresponding to positions 224 and 271 and 72 and 145 and 318 and 73, such as those described above.

In another aspect, the variant alterations comprise or consist of substitutions at positions corresponding to positions 224 and 271 and 72 and 145 and 60 and 73, such as those described above.

In another aspect, the variant alterations comprise or consist of substitutions at positions corresponding to positions 224 and 271 and 72 and 318 and 60 and 73, such as those described above.

In another aspect, the variant alterations comprise or consist of substitutions at positions corresponding to positions 224 and 271 and 77 and 145 and 318 and 60, such as those described above.

In another aspect, the variant alterations comprise or consist of substitutions at positions corresponding to positions 224 and 271 and 77 and 145 and 318 and 73, such as those described above.

In another aspect, the variant alterations comprise or consist of substitutions at positions corresponding to positions 224 and 271 and 77 and 145 and 60 and 73, such as those described above.

In another aspect, the variant alterations comprise or consist of substitutions at positions corresponding to positions 224 and 271 and 77 and 318 and 60 and 73, such as those described above.

In another aspect, the variant alterations comprise or consist of substitutions at positions corresponding to positions 224 and 271 and 145 and 318 and 60 and 73, such as those described above.

In another aspect, the variant alterations comprise or consist of substitutions at positions corresponding to positions 224 and 72 and 77 and 145 and 318 and 60, such as those described above.

In another aspect, the variant alterations comprise or consist of substitutions at positions corresponding to positions 224 and 72 and 77 and 145 and 318 and 73, such as those described above.

In another aspect, the variant alterations comprise or consist of substitutions at positions corresponding to positions 224 and 72 and 77 and 145 and 60 and 73, such as those described above.

In another aspect, the variant alterations comprise or consist of substitutions at positions corresponding to positions 224 and 72 and 77 and 318 and 60 and 73, such as those described above.

In another aspect, the variant alterations comprise or consist of substitutions at positions corresponding to positions 224 and 72 and 145 and 318 and 60 and 73, such as those described above.

In another aspect, the variant alterations comprise or consist of substitutions at positions corresponding to positions 224 and 77 and 145 and 318 and 60 and 73, such as those described above.

In another aspect, the variant alterations comprise or consist of substitutions at positions corresponding to positions 410 and 271 and 72 and 77 and 145 and 318, such as those described above.

In another aspect, the variant alterations comprise or consist of substitutions at positions corresponding to positions 410 and 271 and 72 and 77 and 145 and 60, such as those described above.

In another aspect, the variant alterations comprise or consist of substitutions at positions corresponding to positions 410 and 271 and 72 and 77 and 145 and 73, such as those described above.

In another aspect, the variant alterations comprise or consist of substitutions at positions corresponding to positions 410 and 271 and 72 and 77 and 318 and 60, such as those described above.

In another aspect, the variant alterations comprise or consist of substitutions at positions corresponding to positions 410 and 271 and 72 and 77 and 318 and 73, such as those described above.

In another aspect, the variant alterations comprise or consist of substitutions at positions corresponding to positions 410 and 271 and 72 and 77 and 60 and 73, such as those described above.

In another aspect, the variant alterations comprise or consist of substitutions at positions corresponding to positions 410 and 271 and 72 and 145 and 318 and 60, such as those described above.

In another aspect, the variant alterations comprise or consist of substitutions at positions corresponding to positions 410 and 271 and 72 and 145 and 318 and 73, such as those described above.

In another aspect, the variant alterations comprise or consist of substitutions at positions corresponding to positions 410 and 271 and 72 and 145 and 60 and 73, such as those described above.

In another aspect, the variant alterations comprise or consist of substitutions at positions corresponding to positions 410 and 271 and 72 and 318 and 60 and 73, such as those described above.

In another aspect, the variant alterations comprise or consist of substitutions at positions corresponding to positions 410 and 271 and 77 and 145 and 318 and 60, such as those described above.

In another aspect, the variant alterations comprise or consist of substitutions at positions corresponding to positions 410 and 271 and 77 and 145 and 318 and 73, such as those described above.

In another aspect, the variant alterations comprise or consist of substitutions at positions corresponding to positions 410 and 271 and 77 and 145 and 60 and 73, such as those described above.

In another aspect, the variant alterations comprise or consist of substitutions at positions corresponding to positions 410 and 271 and 77 and 318 and 60 and 73, such as those described above.

In another aspect, the variant alterations comprise or consist of substitutions at positions corresponding to positions 410 and 271 and 145 and 318 and 60 and 73, such as those described above.

In another aspect, the variant alterations comprise or consist of substitutions at positions corresponding to positions 410 and 72 and 77 and 145 and 318 and 60, such as those described above.

In another aspect, the variant alterations comprise or consist of substitutions at positions corresponding to positions 410 and 72 and 77 and 145 and 318 and 73, such as those described above.

In another aspect, the variant alterations comprise or consist of substitutions at positions corresponding to positions 410 and 72 and 77 and 145 and 60 and 73, such as those described above.

In another aspect, the variant alterations comprise or consist of substitutions at positions corresponding to positions 410 and 72 and 77 and 318 and 60 and 73, such as those described above.

In another aspect, the variant alterations comprise or consist of substitutions at positions corresponding to positions 410 and 72 and 145 and 318 and 60 and 73, such as those described above.

In another aspect, the variant alterations comprise or consist of substitutions at positions corresponding to positions 410 and 77 and 145 and 318 and 60 and 73, such as those described above.

In another aspect, the variant alterations comprise or consist of substitutions at positions corresponding to positions 271 and 72 and 77 and 145 and 318 and 60, such as those described above.

In another aspect, the variant alterations comprise or consist of substitutions at positions corresponding to positions 271 and 72 and 77 and 145 and 318 and 73, such as those described above.

In another aspect, the variant alterations comprise or consist of substitutions at positions corresponding to positions 271 and 72 and 77 and 145 and 60 and 73, such as those described above.

In another aspect, the variant alterations comprise or consist of substitutions at positions corresponding to positions 271 and 72 and 77 and 318 and 60 and 73, such as those described above.

In another aspect, the variant alterations comprise or consist of substitutions at positions corresponding to positions 271 and 72 and 145 and 318 and 60 and 73, such as those described above.

In another aspect, the variant alterations comprise or consist of substitutions at positions corresponding to positions 271 and 77 and 145 and 318 and 60 and 73, such as those described above.

In another aspect, the variant alterations comprise or consist of substitutions at positions corresponding to positions 72 and 77 and 145 and 318 and 60 and 73, such as those described above.

In another aspect, the variant alterations comprise or consist of substitutions at positions corresponding to positions 295 and 224 and 410 and 271 and 72 and 77 and 145, such as those described above.

In another aspect, the variant alterations comprise or consist of substitutions at positions corresponding to positions 295 and 224 and 410 and 271 and 72 and 77 and 318, such as those described above.

In another aspect, the variant alterations comprise or consist of substitutions at positions corresponding to positions 295 and 224 and 410 and 271 and 72 and 77 and 60, such as those described above.

In another aspect, the variant alterations comprise or consist of substitutions at positions corresponding to positions 295 and 224 and 410 and 271 and 72 and 77 and 73, such as those described above.

In another aspect, the variant alterations comprise or consist of substitutions at positions corresponding to positions 295 and 224 and 410 and 271 and 72 and 145 and 318, such as those described above.

In another aspect, the variant alterations comprise or consist of substitutions at positions corresponding to positions 295 and 224 and 410 and 271 and 72 and 145 and 60, such as those described above.

In another aspect, the variant alterations comprise or consist of substitutions at positions corresponding to positions 295 and 224 and 410 and 271 and 72 and 145 and 73, such as those described above.

In another aspect, the variant alterations comprise or consist of substitutions at positions corresponding to positions 295 and 224 and 410 and 271 and 72 and 318 and 60, such as those described above.

In another aspect, the variant alterations comprise or consist of substitutions at positions corresponding to positions 295 and 224 and 410 and 271 and 72 and 318 and 73, such as those described above.

In another aspect, the variant alterations comprise or consist of substitutions at positions corresponding to positions 295 and 224 and 410 and 271 and 72 and 60 and 73, such as those described above.

In another aspect, the variant alterations comprise or consist of substitutions at positions corresponding to positions 295 and 224 and 410 and 271 and 77 and 145 and 318, such as those described above.

In another aspect, the variant alterations comprise or consist of substitutions at positions corresponding to positions 295 and 224 and 410 and 271 and 77 and 145 and 60, such as those described above.

In another aspect, the variant alterations comprise or consist of substitutions at positions corresponding to positions 295 and 224 and 410 and 271 and 77 and 145 and 73, such as those described above.

In another aspect, the variant alterations comprise or consist of substitutions at positions corresponding to positions 295 and 224 and 410 and 271 and 77 and 318 and 60, such as those described above.

In another aspect, the variant alterations comprise or consist of substitutions at positions corresponding to positions 295 and 224 and 410 and 271 and 77 and 318 and 73, such as those described above.

In another aspect, the variant alterations comprise or consist of substitutions at positions corresponding to positions 295 and 224 and 410 and 271 and 77 and 60 and 73, such as those described above.

In another aspect, the variant alterations comprise or consist of substitutions at positions corresponding to positions 295 and 224 and 410 and 271 and 145 and 318 and 60, such as those described above.

In another aspect, the variant alterations comprise or consist of substitutions at positions corresponding to positions 295 and 224 and 410 and 271 and 145 and 318 and 73, such as those described above.

In another aspect, the variant alterations comprise or consist of substitutions at positions corresponding to positions 295 and 224 and 410 and 271 and 145 and 60 and 73, such as those described above.

In another aspect, the variant alterations comprise or consist of substitutions at positions corresponding to positions 295 and 224 and 410 and 271 and 318 and 60 and 73, such as those described above.

In another aspect, the variant alterations comprise or consist of substitutions at positions corresponding to positions 295 and 224 and 410 and 72 and 77 and 145 and 318, such as those described above.

In another aspect, the variant alterations comprise or consist of substitutions at positions corresponding to positions 295 and 224 and 410 and 72 and 77 and 145 and 60, such as those described above.

In another aspect, the variant alterations comprise or consist of substitutions at positions corresponding to positions 295 and 224 and 410 and 72 and 77 and 145 and 73, such as those described above.

In another aspect, the variant alterations comprise or consist of substitutions at positions corresponding to positions 295 and 224 and 410 and 72 and 77 and 318 and 60, such as those described above.

In another aspect, the variant alterations comprise or consist of substitutions at positions corresponding to positions 295 and 224 and 410 and 72 and 77 and 318 and 73, such as those described above.

In another aspect, the variant alterations comprise or consist of substitutions at positions corresponding to positions 295 and 224 and 410 and 72 and 77 and 60 and 73, such as those described above.

In another aspect, the variant alterations comprise or consist of substitutions at positions corresponding to positions 295 and 224 and 410 and 72 and 145 and 318 and 60, such as those described above.

In another aspect, the variant alterations comprise or consist of substitutions at positions corresponding to positions 295 and 224 and 410 and 72 and 145 and 318 and 73, such as those described above.

In another aspect, the variant alterations comprise or consist of substitutions at positions corresponding to positions 295 and 224 and 410 and 72 and 145 and 60 and 73, such as those described above.

In another aspect, the variant alterations comprise or consist of substitutions at positions corresponding to positions 295 and 224 and 410 and 72 and 318 and 60 and 73, such as those described above.

In another aspect, the variant alterations comprise or consist of substitutions at positions corresponding to positions 295 and 224 and 410 and 77 and 145 and 318 and 60, such as those described above.

In another aspect, the variant alterations comprise or consist of substitutions at positions corresponding to positions 295 and 224 and 410 and 77 and 145 and 318 and 73, such as those described above.

In another aspect, the variant alterations comprise or consist of substitutions at positions corresponding to positions 295 and 224 and 410 and 77 and 145 and 60 and 73, such as those described above.

In another aspect, the variant alterations comprise or consist of substitutions at positions corresponding to positions 295 and 224 and 410 and 77 and 318 and 60 and 73, such as those described above.

In another aspect, the variant alterations comprise or consist of substitutions at positions corresponding to positions 295 and 224 and 410 and 145 and 318 and 60 and 73, such as those described above.

In another aspect, the variant alterations comprise or consist of substitutions at positions corresponding to positions 295 and 224 and 271 and 72 and 77 and 145 and 318, such as those described above.

In another aspect, the variant alterations comprise or consist of substitutions at positions corresponding to positions 295 and 224 and 271 and 72 and 77 and 145 and 60, such as those described above.

In another aspect, the variant alterations comprise or consist of substitutions at positions corresponding to positions 295 and 224 and 271 and 72 and 77 and 145 and 73, such as those described above.

In another aspect, the variant alterations comprise or consist of substitutions at positions corresponding to positions 295 and 224 and 271 and 72 and 77 and 318 and 60, such as those described above.

In another aspect, the variant alterations comprise or consist of substitutions at positions corresponding to positions 295 and 224 and 271 and 72 and 77 and 318 and 73, such as those described above.

In another aspect, the variant alterations comprise or consist of substitutions at positions corresponding to positions 295 and 224 and 271 and 72 and 77 and 60 and 73, such as those described above.

In another aspect, the variant alterations comprise or consist of substitutions at positions corresponding to positions 295 and 224 and 271 and 72 and 145 and 318 and 60, such as those described above.

In another aspect, the variant alterations comprise or consist of substitutions at positions corresponding to positions 295 and 224 and 271 and 72 and 145 and 318 and 73, such as those described above.

In another aspect, the variant alterations comprise or consist of substitutions at positions corresponding to positions 295 and 224 and 271 and 72 and 145 and 60 and 73, such as those described above.

In another aspect, the variant alterations comprise or consist of substitutions at positions corresponding to positions 295 and 224 and 271 and 72 and 318 and 60 and 73, such as those described above.

In another aspect, the variant alterations comprise or consist of substitutions at positions corresponding to positions 295 and 224 and 271 and 77 and 145 and 318 and 60, such as those described above.

In another aspect, the variant alterations comprise or consist of substitutions at positions corresponding to positions 295 and 224 and 271 and 77 and 145 and 318 and 73, such as those described above.

In another aspect, the variant alterations comprise or consist of substitutions at positions corresponding to positions 295 and 224 and 271 and 77 and 145 and 60 and 73, such as those described above.

In another aspect, the variant alterations comprise or consist of substitutions at positions corresponding to positions 295 and 224 and 271 and 77 and 318 and 60 and 73, such as those described above.

In another aspect, the variant alterations comprise or consist of substitutions at positions corresponding to positions 295 and 224 and 271 and 145 and 318 and 60 and 73, such as those described above.

In another aspect, the variant alterations comprise or consist of substitutions at positions corresponding to positions 295 and 224 and 72 and 77 and 145 and 318 and 60, such as those described above.

In another aspect, the variant alterations comprise or consist of substitutions at positions corresponding to positions 295 and 224 and 72 and 77 and 145 and 318 and 73, such as those described above.

In another aspect, the variant alterations comprise or consist of substitutions at positions corresponding to positions 295 and 224 and 72 and 77 and 145 and 60 and 73, such as those described above.

In another aspect, the variant alterations comprise or consist of substitutions at positions corresponding to positions 295 and 224 and 72 and 77 and 318 and 60 and 73, such as those described above.

In another aspect, the variant alterations comprise or consist of substitutions at positions corresponding to positions 295 and 224 and 72 and 145 and 318 and 60 and 73, such as those described above.

In another aspect, the variant alterations comprise or consist of substitutions at positions corresponding to positions 295 and 224 and 77 and 145 and 318 and 60 and 73, such as those described above.

In another aspect, the variant alterations comprise or consist of substitutions at positions corresponding to positions 295 and 410 and 271 and 72 and 77 and 145 and 318, such as those described above.

In another aspect, the variant alterations comprise or consist of substitutions at positions corresponding to positions 295 and 410 and 271 and 72 and 77 and 145 and 60, such as those described above.

In another aspect, the variant alterations comprise or consist of substitutions at positions corresponding to positions 295 and 410 and 271 and 72 and 77 and 145 and 73, such as those described above.

In another aspect, the variant alterations comprise or consist of substitutions at positions corresponding to positions 295 and 410 and 271 and 72 and 77 and 318 and 60, such as those described above.

In another aspect, the variant alterations comprise or consist of substitutions at positions corresponding to positions 295 and 410 and 271 and 72 and 77 and 318 and 73, such as those described above.

In another aspect, the variant alterations comprise or consist of substitutions at positions corresponding to positions 295 and 410 and 271 and 72 and 77 and 60 and 73, such as those described above.

In another aspect, the variant alterations comprise or consist of substitutions at positions corresponding to positions 295 and 410 and 271 and 72 and 145 and 318 and 60, such as those described above.

In another aspect, the variant alterations comprise or consist of substitutions at positions corresponding to positions 295 and 410 and 271 and 72 and 145 and 318 and 73, such as those described above.

In another aspect, the variant alterations comprise or consist of substitutions at positions corresponding to positions 295 and 410 and 271 and 72 and 145 and 60 and 73, such as those described above.

In another aspect, the variant alterations comprise or consist of substitutions at positions corresponding to positions 295 and 410 and 271 and 72 and 318 and 60 and 73, such as those described above.

In another aspect, the variant alterations comprise or consist of substitutions at positions corresponding to positions 295 and 410 and 271 and 77 and 145 and 318 and 60, such as those described above.

In another aspect, the variant alterations comprise or consist of substitutions at positions corresponding to positions 295 and 410 and 271 and 77 and 145 and 318 and 73, such as those described above.

In another aspect, the variant alterations comprise or consist of substitutions at positions corresponding to positions 295 and 410 and 271 and 77 and 145 and 60 and 73, such as those described above.

In another aspect, the variant alterations comprise or consist of substitutions at positions corresponding to positions 295 and 410 and 271 and 77 and 318 and 60 and 73, such as those described above.

In another aspect, the variant alterations comprise or consist of substitutions at positions corresponding to positions 295 and 410 and 271 and 145 and 318 and 60 and 73, such as those described above.

In another aspect, the variant alterations comprise or consist of substitutions at positions corresponding to positions 295 and 410 and 72 and 77 and 145 and 318 and 60, such as those described above.

In another aspect, the variant alterations comprise or consist of substitutions at positions corresponding to positions 295 and 410 and 72 and 77 and 145 and 318 and 73, such as those described above.

In another aspect, the variant alterations comprise or consist of substitutions at positions corresponding to positions 295 and 410 and 72 and 77 and 145 and 60 and 73, such as those described above.

In another aspect, the variant alterations comprise or consist of substitutions at positions corresponding to positions 295 and 410 and 72 and 77 and 318 and 60 and 73, such as those described above.

In another aspect, the variant alterations comprise or consist of substitutions at positions corresponding to positions 295 and 410 and 72 and 145 and 318 and 60 and 73, such as those described above.

In another aspect, the variant alterations comprise or consist of substitutions at positions corresponding to positions 295 and 410 and 77 and 145 and 318 and 60 and 73, such as those described above.

In another aspect, the variant alterations comprise or consist of substitutions at positions corresponding to positions 295 and 271 and 72 and 77 and 145 and 318 and 60, such as those described above.

In another aspect, the variant alterations comprise or consist of substitutions at positions corresponding to positions 295 and 271 and 72 and 77 and 145 and 318 and 73, such as those described above.

In another aspect, the variant alterations comprise or consist of substitutions at positions corresponding to positions 295 and 271 and 72 and 77 and 145 and 60 and 73, such as those described above.

In another aspect, the variant alterations comprise or consist of substitutions at positions corresponding to positions 295 and 271 and 72 and 77 and 318 and 60 and 73, such as those described above.

In another aspect, the variant alterations comprise or consist of substitutions at positions corresponding to positions 295 and 271 and 72 and 145 and 318 and 60 and 73, such as those described above.

In another aspect, the variant alterations comprise or consist of substitutions at positions corresponding to positions 295 and 271 and 77 and 145 and 318 and 60 and 73, such as those described above.

In another aspect, the variant alterations comprise or consist of substitutions at positions corresponding to positions 295 and 72 and 77 and 145 and 318 and 60 and 73, such as those described above.

In another aspect, the variant alterations comprise or consist of substitutions at positions corresponding to positions 224 and 410 and 271 and 72 and 77 and 145 and 318, such as those described above.

In another aspect, the variant alterations comprise or consist of substitutions at positions corresponding to positions 224 and 410 and 271 and 72 and 77 and 145 and 60, such as those described above.

In another aspect, the variant alterations comprise or consist of substitutions at positions corresponding to positions 224 and 410 and 271 and 72 and 77 and 145 and 73, such as those described above.

In another aspect, the variant alterations comprise or consist of substitutions at positions corresponding to positions 224 and 410 and 271 and 72 and 77 and 318 and 60, such as those described above.

In another aspect, the variant alterations comprise or consist of substitutions at positions corresponding to positions 224 and 410 and 271 and 72 and 77 and 318 and 73, such as those described above.

In another aspect, the variant alterations comprise or consist of substitutions at positions corresponding to positions 224 and 410 and 271 and 72 and 77 and 60 and 73, such as those described above.

In another aspect, the variant alterations comprise or consist of substitutions at positions corresponding to positions 224 and 410 and 271 and 72 and 145 and 318 and 60, such as those described above.

In another aspect, the variant alterations comprise or consist of substitutions at positions corresponding to positions 224 and 410 and 271 and 72 and 145 and 318 and 73, such as those described above.

In another aspect, the variant alterations comprise or consist of substitutions at positions corresponding to positions 224 and 410 and 271 and 72 and 145 and 60 and 73, such as those described above.

In another aspect, the variant alterations comprise or consist of substitutions at positions corresponding to positions 224 and 410 and 271 and 72 and 318 and 60 and 73, such as those described above.

In another aspect, the variant alterations comprise or consist of substitutions at positions corresponding to positions 224 and 410 and 271 and 77 and 145 and 318 and 60, such as those described above.

In another aspect, the variant alterations comprise or consist of substitutions at positions corresponding to positions 224 and 410 and 271 and 77 and 145 and 318 and 73, such as those described above.

In another aspect, the variant alterations comprise or consist of substitutions at positions corresponding to positions 224 and 410 and 271 and 77 and 145 and 60 and 73, such as those described above.

In another aspect, the variant alterations comprise or consist of substitutions at positions corresponding to positions 224 and 410 and 271 and 77 and 318 and 60 and 73, such as those described above.

In another aspect, the variant alterations comprise or consist of substitutions at positions corresponding to positions 224 and 410 and 271 and 145 and 318 and 60 and 73, such as those described above.

In another aspect, the variant alterations comprise or consist of substitutions at positions corresponding to positions 224 and 410 and 72 and 77 and 145 and 318 and 60, such as those described above.

In another aspect, the variant alterations comprise or consist of substitutions at positions corresponding to positions 224 and 410 and 72 and 77 and 145 and 318 and 73, such as those described above.

In another aspect, the variant alterations comprise or consist of substitutions at positions corresponding to positions 224 and 410 and 72 and 77 and 145 and 60 and 73, such as those described above.

In another aspect, the variant alterations comprise or consist of substitutions at positions corresponding to positions 224 and 410 and 72 and 77 and 318 and 60 and 73, such as those described above.

In another aspect, the variant alterations comprise or consist of substitutions at positions corresponding to positions 224 and 410 and 72 and 145 and 318 and 60 and 73, such as those described above.

In another aspect, the variant alterations comprise or consist of substitutions at positions corresponding to positions 224 and 410 and 77 and 145 and 318 and 60 and 73, such as those described above.

In another aspect, the variant alterations comprise or consist of substitutions at positions corresponding to positions 224 and 271 and 72 and 77 and 145 and 318 and 60, such as those described above.

In another aspect, the variant alterations comprise or consist of substitutions at positions corresponding to positions 224 and 271 and 72 and 77 and 145 and 318 and 73, such as those described above.

In another aspect, the variant alterations comprise or consist of substitutions at positions corresponding to positions 224 and 271 and 72 and 77 and 145 and 60 and 73, such as those described above.

In another aspect, the variant alterations comprise or consist of substitutions at positions corresponding to positions 224 and 271 and 72 and 77 and 318 and 60 and 73, such as those described above.

In another aspect, the variant alterations comprise or consist of substitutions at positions corresponding to positions 224 and 271 and 72 and 145 and 318 and 60 and 73, such as those described above.

In another aspect, the variant alterations comprise or consist of substitutions at positions corresponding to positions 224 and 271 and 77 and 145 and 318 and 60 and 73, such as those described above.

In another aspect, the variant alterations comprise or consist of substitutions at positions corresponding to positions 224 and 72 and 77 and 145 and 318 and 60 and 73, such as those described above.

In another aspect, the variant alterations comprise or consist of substitutions at positions corresponding to positions 410 and 271 and 72 and 77 and 145 and 318 and 60, such as those described above.

In another aspect, the variant alterations comprise or consist of substitutions at positions corresponding to positions 410 and 271 and 72 and 77 and 145 and 318 and 73, such as those described above.

In another aspect, the variant alterations comprise or consist of substitutions at positions corresponding to positions 410 and 271 and 72 and 77 and 145 and 60 and 73, such as those described above.

In another aspect, the variant alterations comprise or consist of substitutions at positions corresponding to positions 410 and 271 and 72 and 77 and 318 and 60 and 73, such as those described above.

In another aspect, the variant alterations comprise or consist of substitutions at positions corresponding to positions 410 and 271 and 72 and 145 and 318 and 60 and 73, such as those described above.

In another aspect, the variant alterations comprise or consist of substitutions at positions corresponding to positions 410 and 271 and 77 and 145 and 318 and 60 and 73, such as those described above.

In another aspect, the variant alterations comprise or consist of substitutions at positions corresponding to positions 410 and 72 and 77 and 145 and 318 and 60 and 73, such as those described above.

In another aspect, the variant alterations comprise or consist of substitutions at positions corresponding to positions 271 and 72 and 77 and 145 and 318 and 60 and 73, such as those described above.

In another aspect, the variant alterations comprise or consist of substitutions at positions corresponding to positions 295 and 224 and 410 and 271 and 72 and 77 and 145 and 318, such as those described above.

In another aspect, the variant alterations comprise or consist of substitutions at positions corresponding to positions 295 and 224 and 410 and 271 and 72 and 77 and 145 and 60, such as those described above.

In another aspect, the variant alterations comprise or consist of substitutions at positions corresponding to positions 295 and 224 and 410 and 271 and 72 and 77 and 145 and 73, such as those described above.

In another aspect, the variant alterations comprise or consist of substitutions at positions corresponding to positions 295 and 224 and 410 and 271 and 72 and 77 and 318 and 60, such as those described above.

In another aspect, the variant alterations comprise or consist of substitutions at positions corresponding to positions 295 and 224 and 410 and 271 and 72 and 77 and 318 and 73, such as those described above.

In another aspect, the variant alterations comprise or consist of substitutions at positions corresponding to positions 295 and 224 and 410 and 271 and 72 and 77 and 60 and 73, such as those described above.

In another aspect, the variant alterations comprise or consist of substitutions at positions corresponding to positions 295 and 224 and 410 and 271 and 72 and 145 and 318 and 60, such as those described above.

In another aspect, the variant alterations comprise or consist of substitutions at positions corresponding to positions 295 and 224 and 410 and 271 and 72 and 145 and 318 and 73, such as those described above.

In another aspect, the variant alterations comprise or consist of substitutions at positions corresponding to positions 295 and 224 and 410 and 271 and 72 and 145 and 60 and 73, such as those described above.

In another aspect, the variant alterations comprise or consist of substitutions at positions corresponding to positions 295 and 224 and 410 and 271 and 72 and 318 and 60 and 73, such as those described above.

In another aspect, the variant alterations comprise or consist of substitutions at positions corresponding to positions 295 and 224 and 410 and 271 and 77 and 145 and 318 and 60, such as those described above.

In another aspect, the variant alterations comprise or consist of substitutions at positions corresponding to positions 295 and 224 and 410 and 271 and 77 and 145 and 318 and 73, such as those described above.

In another aspect, the variant alterations comprise or consist of substitutions at positions corresponding to positions 295 and 224 and 410 and 271 and 77 and 145 and 60 and 73, such as those described above.

In another aspect, the variant alterations comprise or consist of substitutions at positions corresponding to positions 295 and 224 and 410 and 271 and 77 and 318 and 60 and 73, such as those described above.

In another aspect, the variant alterations comprise or consist of substitutions at positions corresponding to positions 295 and 224 and 410 and 271 and 145 and 318 and 60 and 73, such as those described above.

In another aspect, the variant alterations comprise or consist of substitutions at positions corresponding to positions 295 and 224 and 410 and 72 and 77 and 145 and 318 and 60, such as those described above.

In another aspect, the variant alterations comprise or consist of substitutions at positions corresponding to positions 295 and 224 and 410 and 72 and 77 and 145 and 318 and 73, such as those described above.

In another aspect, the variant alterations comprise or consist of substitutions at positions corresponding to positions 295 and 224 and 410 and 72 and 77 and 145 and 60 and 73, such as those described above.

In another aspect, the variant alterations comprise or consist of substitutions at positions corresponding to positions 295 and 224 and 410 and 72 and 77 and 318 and 60 and 73, such as those described above.

In another aspect, the variant alterations comprise or consist of substitutions at positions corresponding to positions 295 and 224 and 410 and 72 and 145 and 318 and 60 and 73, such as those described above.

In another aspect, the variant alterations comprise or consist of substitutions at positions corresponding to positions 295 and 224 and 410 and 77 and 145 and 318 and 60 and 73, such as those described above.

In another aspect, the variant alterations comprise or consist of substitutions at positions corresponding to positions 295 and 224 and 271 and 72 and 77 and 145 and 318 and 60, such as those described above.

In another aspect, the variant alterations comprise or consist of substitutions at positions corresponding to positions 295 and 224 and 271 and 72 and 77 and 145 and 318 and 73, such as those described above.

In another aspect, the variant alterations comprise or consist of substitutions at positions corresponding to positions 295 and 224 and 271 and 72 and 77 and 145 and 60 and 73, such as those described above.

In another aspect, the variant alterations comprise or consist of substitutions at positions corresponding to positions 295 and 224 and 271 and 72 and 77 and 318 and 60 and 73, such as those described above.

In another aspect, the variant alterations comprise or consist of substitutions at positions corresponding to positions 295 and 224 and 271 and 72 and 145 and 318 and 60 and 73, such as those described above.

In another aspect, the variant alterations comprise or consist of substitutions at positions corresponding to positions 295 and 224 and 271 and 77 and 145 and 318 and 60 and 73, such as those described above.

In another aspect, the variant alterations comprise or consist of substitutions at positions corresponding to positions 295 and 224 and 72 and 77 and 145 and 318 and 60 and 73, such as those described above.

In another aspect, the variant alterations comprise or consist of substitutions at positions corresponding to positions 295 and 410 and 271 and 72 and 77 and 145 and 318 and 60, such as those described above.

In another aspect, the variant alterations comprise or consist of substitutions at positions corresponding to positions 295 and 410 and 271 and 72 and 77 and 145 and 318 and 73, such as those described above.

In another aspect, the variant alterations comprise or consist of substitutions at positions corresponding to positions 295 and 410 and 271 and 72 and 77 and 145 and 60 and 73, such as those described above.

In another aspect, the variant alterations comprise or consist of substitutions at positions corresponding to positions 295 and 410 and 271 and 72 and 77 and 318 and 60 and 73, such as those described above.

In another aspect, the variant alterations comprise or consist of substitutions at positions corresponding to positions 295 and 410 and 271 and 72 and 145 and 318 and 60 and 73, such as those described above.

In another aspect, the variant alterations comprise or consist of substitutions at positions corresponding to positions 295 and 410 and 271 and 77 and 145 and 318 and 60 and 73, such as those described above.

In another aspect, the variant alterations comprise or consist of substitutions at positions corresponding to positions 295 and 410 and 72 and 77 and 145 and 318 and 60 and 73, such as those described above.

In another aspect, the variant alterations comprise or consist of substitutions at positions corresponding to positions 295 and 271 and 72 and 77 and 145 and 318 and 60 and 73, such as those described above.

In another aspect, the variant alterations comprise or consist of substitutions at positions corresponding to positions 224 and 410 and 271 and 72 and 77 and 145 and 318 and 60, such as those described above.

In another aspect, the variant alterations comprise or consist of substitutions at positions corresponding to positions 224 and 410 and 271 and 72 and 77 and 145 and 318 and 73, such as those described above.

In another aspect, the variant alterations comprise or consist of substitutions at positions corresponding to positions 224 and 410 and 271 and 72 and 77 and 145 and 60 and 73, such as those described above.

In another aspect, the variant alterations comprise or consist of substitutions at positions corresponding to positions 224 and 410 and 271 and 72 and 77 and 318 and 60 and 73, such as those described above.

In another aspect, the variant alterations comprise or consist of substitutions at positions corresponding to positions 224 and 410 and 271 and 72 and 145 and 318 and 60 and 73, such as those described above.

In another aspect, the variant alterations comprise or consist of substitutions at positions corresponding to positions 224 and 410 and 271 and 77 and 145 and 318 and 60 and 73, such as those described above.

In another aspect, the variant alterations comprise or consist of substitutions at positions corresponding to positions 224 and 410 and 72 and 77 and 145 and 318 and 60 and 73, such as those described above.

In another aspect, the variant alterations comprise or consist of substitutions at positions corresponding to positions 224 and 271 and 72 and 77 and 145 and 318 and 60 and 73, such as those described above.

In another aspect, the variant alterations comprise or consist of substitutions at positions corresponding to positions 410 and 271 and 72 and 77 and 145 and 318 and 60 and 73, such as those described above.

In another aspect, the variant alterations comprise or consist of substitutions at positions corresponding to positions 295 and 224 and 410 and 271 and 72 and 77 and 145 and 318 and 60, such as those described above.

In another aspect, the variant alterations comprise or consist of substitutions at positions corresponding to positions 295 and 224 and 410 and 271 and 72 and 77 and 145 and 318 and 73, such as those described above.

In another aspect, the variant alterations comprise or consist of substitutions at positions corresponding to positions 295 and 224 and 410 and 271 and 72 and 77 and 145 and 60 and 73, such as those described above.

In another aspect, the variant alterations comprise or consist of substitutions at positions corresponding to positions 295 and 224 and 410 and 271 and 72 and 77 and 318 and 60 and 73, such as those described above.

In another aspect, the variant alterations comprise or consist of substitutions at positions corresponding to positions 295 and 224 and 410 and 271 and 72 and 145 and 318 and 60 and 73, such as those described above.

In another aspect, the variant alterations comprise or consist of substitutions at positions corresponding to positions 295 and 224 and 410 and 271 and 77 and 145 and 318 and 60 and 73, such as those described above.

In another aspect, the variant alterations comprise or consist of substitutions at positions corresponding to positions 295 and 224 and 410 and 72 and 77 and 145 and 318 and 60 and 73, such as those described above.

In another aspect, the variant alterations comprise or consist of substitutions at positions corresponding to positions 295 and 224 and 271 and 72 and 77 and 145 and 318 and 60 and 73, such as those described above.

In another aspect, the variant alterations comprise or consist of substitutions at positions corresponding to positions 295 and 410 and 271 and 72 and 77 and 145 and 318 and 60 and 73, such as those described above.

In another aspect, the variant alterations comprise or consist of substitutions at positions corresponding to positions 224 and 410 and 271 and 72 and 77 and 145 and 318 and 60 and 73, such as those described above.

In another aspect, the variant alterations comprise or consist of substitutions at positions corresponding to positions 295 and 224 and 410 and 271 and 72 and 77 and 145 and 318 and 60 and 73, such as those described above.

In one aspect the present invention relates to a glucoamylase variant comprising a substitution at a position corresponding to position 295 of the polypeptide of SEQ ID NO: 2, wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2.

In addition the variant may further comprises a substitution at least at one or more position corresponding to position 32, 83, 163, 169, 219, 224, 303 or 410 of the polypeptide of SEQ ID NO: 2, wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2.

The exemplified variants disclosed herein were all constructed based on the parent glucoamylase of SEQ ID NO: 2. Thus the starting amino acid to be substituted was included, e.g., Y295F, however, since other parent glucoamylases may also be improved according to the invention, in such cases the starting amino acid may be different. Therefore the specific substitutions can also be describe by only specifying the amino acid to be present in a given position after substitution has taken place. In the following, only the amino acid present after substitutions has been specified.

Thus the variants of the invention in one embodiment comprises at least one or more of the substitutions selected from 295F, 295W, 224A, 224I, 224T, 32V, 83D, 163A, 163W, 169I, 219R, 303N or 410K.

In another aspect, the variant comprises at least one of the following substitutions of the polypeptide of SEQ ID NO: 2:
295F;
295W;
224A;
224I;
224T;
271Q;
318V; or
410K; and wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2.

In another embodiment the variant comprises at least one of the following substitutions or combinations of substitutions of the polypeptide of SEQ ID NO: 2:
295W; or
295W+410K; or
224I+295F; or
224T+295W+318V; or
295F; or
224A+295F; or
295W+83D+410K; or
163A+295W+410K; or
163W+295W+410K; or
303N+295W; or
169I+295W; or
32V+219R+295W; and wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2.

In another embodiment the variant comprises at least one of the following substitutions or combinations of substitutions of the polypeptide of SEQ ID NO: 2:
295W; or
295W+410K; or
224I+295F; or
224T+295W+318V; or
295F; or
224A+295F; or
295W+83D+410K; or
163A+295W+410K; or
163W+295W+410K; or
303N+295W; or
169I+295W; or
32V+219R+295W; and wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2; and wherein the variants have reduced glucose inhibition compared to the glucoamylase of SEQ ID NO: 2

In one embodiment the substitutions are selected from Y295F, Y295W, L224A, L224I, L224T, A32V, S83D, N163A, N163W, V169I, T219R, 5303N, R410K, and Q318V.

In another aspect the present invention relates to a glucoamylase variant, comprising a substitution at one or more positions corresponding to positions 271, 410, 72, 77, 145, 219, 303, 224, 318 of the polypeptide of SEQ ID NO: 2, wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2.

In one embodiment the variant comprises at least one or more of the substitutions selected from 72V, 77A, 145A, 219D, 271Q, 271N, 271A, 271S, 271V, 224Q, 303E, 318W, 318F, 410A, 410Q or 410H.

In embodiment, the variant comprises at least one of the following substitutions of the polypeptide of SEQ ID NO: 2:
72V;
77A;
145A;
219D;
271Q;
271N;
271A;
271S;
271V;
224Q;
303E;
318W;
318F;
410A
410Q; or
410H; and wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2.

In another embodiment, the variant comprises at least one of the following substitutions or combinations of substitutions of the polypeptide of SEQ ID NO: 2:
72V+145A; or
271Q; or
224Q+271N+410A; or
77A; or
77A+271A; or
271S+318W+410Q; or
271V+318F+410H; or
77A+219D; or
77A+303E;
and wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2.

In another embodiment, the variant comprises at least one of the following substitutions or combinations of substitutions of the polypeptide of SEQ ID NO: 2:
72V+145A; or
271Q; or
224Q+271N+410A; or
77A; or
77A+271A; or
271S+318W+410Q; or
271V+318F+410H; or
77A+219D; or
77A+303E;
and wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2, and wherein variant glucoamylase has increased specific activity compared to the glucoamylase of SEQ ID NO: 2.

In one embodiment the substitutions are selected from D72V, L77A, L145A, T219D, L224Q, T271Q, T271N, T271A, T271S, T271V, S303E, Q318W, Q318F, R410Q, R410H and R410A.

In particular the variants have improved properties compared to the glucoamylase disclosed as SEQ ID NO: 2.

Particularly, the improved property is reduced glucose inhibition and/or increased specific activity.

In another particular embodiment the improved property is increased ethanol yield in a process of the invention when the variant glucoamylase is present during saccharification and, particularly simultaneous saccharification and fermentation (SSF).

Thus in a further aspect the present invention relates to a glucoamylase variant, comprising a substitution at one or more positions corresponding to positions 271 or 295, or at positions 271 and 295 of the polypeptide of SEQ ID NO: 2, wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2.

In one embodiment the variant comprises at least one or more of the substitutions selected from 271Q, 271A, 271V, 295W, 60L, 73A, 77A, 77V, and 318Y.

In another embodiment, the variant comprises at least one of the following substitutions of the polypeptide of SEQ ID NO: 2:
60L; or
73A; or
271Q; or
271A; or
271V; or
295W; or
77V; or
77A; or
318Y; and wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2.

In another embodiment, the variant comprises at least the following substitutions or combinations of substitutions of the polypeptide of SEQ ID NO: 2:
60L+73A+271Q;
271Q;
77V+271V+410A;
77A+271A;
271V+318Y;
295W;
271Q+295W; and wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2.

In another embodiment, the variant comprises at least the following substitutions or combinations of substitutions of the polypeptide of SEQ ID NO: 2:
60L+73A+271Q;
271Q;
77V+271V+410A;
77A+271A;
271V+318Y;
295W;
271Q+295W; and wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2, and wherein the variant provides increased ethanol yield when used in SSF, compared to the glucoamylase of SEQ ID NO: 2.

In one embodiment the substitutions are selected from F60L, S73A, T271A, T271V, T271Q, L77A, L77V, R410A, Y295W, and Q318Y.

In still another embodiment the present invention relates to glucoamylase variants comprising at least the following substitutions or combinations of substitutions of the polypeptide of SEQ ID NO: 2:
F60L+S73A+T271Q;
T271Q;
L77V+T271V+R410A;
L77A+T271A;
T271V+Q318Y;
Y295W;
T271Q+Y295W; and
wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2.

In still another aspect the present invention relates to glucoamylase variants comprising at least the following substitutions or combinations of substitutions of the polypeptide of SEQ ID NO: 2:
F60L+S73A+T271Q;
T271Q;
L77V+T271V+R410A;
L77A+T271A;
T271V+Q318Y;
Y295W;
T271Q+Y295W; and
wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2; and wherein the variant provides increased ethanol yield when used in SSF, compared to the glucoamylase of SEQ ID NO: 2.

The variants may further comprise one or more additional substitutions at one or more (e.g., several) other positions.

It should be noted that for all of the disclosed specific variants such further variation could be introduced without affecting significantly the properties of the glucoamylase variants. In one aspect, the number of substitutions in the variants of the present invention in addition to the specific substitutions discussed herein is 1-20, e.g., 1-10 and 1-5, such as 1, 2, 3, 4, 5, 6, 7, 8, 9 or 10 substitutions.

Therefore the % identity of the variant polypeptide compared to the parent polypeptide of SEQ ID NO: 2 may be at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 2.

In one particular embodiment the above variants have glucoamylase activity, and the variant has at least 85%, but less than 100%, sequence identity to the polypeptide of SEQ ID NO: 2.

In one particular embodiment the above variants have glucoamylase activity, and the variant has at least 90%, but less than 100%, sequence identity to the polypeptide of SEQ ID NO: 2.

In one particular embodiment the above variants have glucoamylase activity, and the variant has at least 91%, but less than 100%, sequence identity to the polypeptide of SEQ ID NO: 2.

In one particular embodiment the above variants have glucoamylase activity, and the variant has at least 92%, but less than 100%, sequence identity to the polypeptide of SEQ ID NO: 2.

In one particular embodiment the above variants have glucoamylase activity, and the variant has at least 93%, but less than 100%, sequence identity to the polypeptide of SEQ ID NO: 2.

In one particular embodiment the above variants have glucoamylase activity, and the variant has at least 94%, but less than 100%, sequence identity to the polypeptide of SEQ ID NO: 2.

In one particular embodiment the above variants have glucoamylase activity, and the variant has at least 95%, but less than 100%, sequence identity to the polypeptide of SEQ ID NO: 2.

In one particular embodiment the above variants have glucoamylase activity, and the variant has at least 96%, but less than 100%, sequence identity to the polypeptide of SEQ ID NO: 2.

In one particular embodiment the above variants have glucoamylase activity, and the variant has at least 97%, but less than 100%, sequence identity to the polypeptide of SEQ ID NO: 2.

In one particular embodiment the above variants have glucoamylase activity, and the variant has at least 98%, but less than 100%, sequence identity to the polypeptide of SEQ ID NO: 2.

In one particular embodiment the above variants have glucoamylase activity, and the variant has at least 99%, but less than 100%, sequence identity to the polypeptide of SEQ ID NO: 2.

The amino acid changes that may be present in addition to the specific substitutions described herein may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for glucoamylase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

In an embodiment, the variant glucoamylase has improved specific activity compared to the parent enzyme. Specific activity was determined using the AGU assay.

In an embodiment, the variant glucoamylase has reduced glucose inhibition compared to the parent glucoamylase of SEQ ID NO: 2. Glucose inhibition was determined as the ratio of glucoamylase activity with and without 30% glucose relative to the wild type parent enzyme disclosed as SEQ ID NO: 2.

In another embodiment the variant glucoamylase has reduced isomaltose forming activity compared to the parent glucoamylase of SEQ ID NO: 2.

In another embodiment the variant glucoamylase has increased DE11 activity compared to the parent glucoamylase of SEQ ID NO: 2.

In another embodiment the variant glucoamylase has increased thermo-stability compared to the parent glucoamylase of SEQ ID NO: 2.

In another embodiment the variant glucoamylase has increased EtOH yield compared to the parent glucoamylase of SEQ ID NO: 2, when the variant is applied in saccharification followed by fermentation on a liquefied mash.

For details see the Materials and Methods section included herein.

Parent Glucoamylases

The parent glucoamylase may be (a) a polypeptide having at least 85% sequence identity to the polypeptide of SEQ ID NO: 2; (b) a polypeptide encoded by a polynucleotide that hybridizes under medium-high stringency conditions with (i) the mature polypeptide coding sequence of SEQ ID NO: 1, or (ii) the full-length complement of (i); or (c) a polypeptide encoded by a polynucleotide having at least 70% sequence identity to the mature polypeptide coding sequence of SEQ ID NO: 1.

In an aspect, the parent has a sequence identity to the polypeptide of SEQ ID NO: 2 of at least 85%, at least 90%, at least 91%, at least 92%, at least 93%, at least 94%, at least 95%, at least 96%, at least 97%, at least 98%, at least 99%, or 100%, which have glucoamylase activity. In one aspect, the amino acid sequence of the parent differs by up to 10 amino acids, e.g., 1, 2, 3, 4, 5, 6, 7, 8, 9, or 10, from the mature polypeptide of SEQ ID NO: 2.

In another aspect, the parent comprises or consists of the amino acid sequence of SEQ ID NO: 2. In another embodiment, the parent is an allelic variant of the polypeptide of SEQ ID NO: 2.

In another aspect, the parent is encoded by a polynucleotide that hybridizes under high stringency conditions or very high stringency conditions with (i) the mature polypeptide coding sequence of SEQ ID NO: 1, or (ii) the full-length complement of (i) (Sambrook et al., 1989, *Molecular Cloning, A Laboratory Manual*, 2d edition, Cold Spring Harbor, N.Y.).

The polynucleotide of SEQ ID NO: 1 or a subsequence thereof, as well as the polypeptide of SEQ ID NO: 2 or a fragment thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 1; (ii) the mature polypeptide coding sequence of SEQ ID NO: 1; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1. In another aspect, the nucleic acid probe is nucleotides 52 to 1728 of SEQ ID NO: 1. In another aspect, the nucleic acid probe is a polynucleotide that encodes the polypeptide of SEQ ID NO: 2; or a fragment thereof. In another aspect, the nucleic acid probe is SEQ ID NO: 1.

In another embodiment, the parent is encoded by a polynucleotide having a sequence identity to the mature polypeptide coding sequence of SEQ ID NO: 1 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be a fungal glucoamylase. For example, the parent may be a *Gloeophyllum*, or a *Trametes* glucoamylase.

In another aspect, the parent is a *Gloeophyllum trabeum*, *Gloeophyllum sepiarium*, or *Trametes cingulata* glucoamylase.

In another aspect, the parent is a *Gloeophyllum trabeum* glucoamylase, e.g., the glucoamylase of SEQ ID NO: 2.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to isolated polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., *In, Ainsworth and Bisby's Dictionary of The Fungi,* 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series No. 9,* 1980).

The yeast host cell may be a *Candida, Hansenula, Kluyveromyces, Pichia, Saccharomyces, Schizosaccharomyces,* or *Yarrowia* cell such as a *Kluyveromyces lactis, Saccharomyces carlsbergensis, Saccharomyces cerevisiae, Saccharomyces diastaticus, Saccharomyces douglasii,*

*Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenaturn, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a host cell of the present invention under conditions suitable for expression of the variant; and (b) optionally recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant. In a particular embodiment variant glucoamylase of the invention is not recovered and the host cell is a yeast host cell. In particular the yeast is a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell. In preferred embodiment the yeast is *Saccharomyces cerevisiae*.

Compositions

The present invention also relates to compositions comprising a polypeptide of the present invention. Preferably the composition also comprises a carrier and/or an excipient. More preferably, the compositions are enriched in such a polypeptide. The term "enriched" indicates that the glucoamylase activity of the composition has been increased, e.g., with an enrichment factor of at least 1.1. Preferably, the compositions are formulated to provide desirable characteristics such as low color, low odor and acceptable storage stability.

The composition may comprise a polypeptide of the present invention as the major enzymatic component, e.g., a mono-component composition. Alternatively, the composition may comprise multiple enzymatic activities, such as an aminopeptidase, alpha-amylase, isoamylase carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, pullulanase, proteolytic enzyme, ribonuclease, transglutaminase, or xylanase.

In a particular embodiment the composition comprises an alpha-amylase and the variant glucoamylase according to the invention. In another embodiment the composition comprises an isoamylase and the variant glucoamylase according to the invention. In another embodiment the composition comprises an alpha-amylase, an isoamylase and the variant glucoamylase according to the invention.

In another aspect the composition comprises the variant glucoamylase of the invention combined with a pullulanase. In another aspect the composition comprises the variant glucoamylase of the invention combined with a pullulanase, and an isoamylase. In another aspect the composition comprises the variant glucoamylase of the invention combined with a pullulanase, and an alpha-amylase.

In a particular embodiment the composition further comprises a protease.

The polypeptide compositions may be prepared in accordance with methods known in the art and may be in the form of a liquid or a dry composition. For instance, the polypeptide composition may be in the form of a granulate or a micro-granulate. The polypeptide to be included in the composition may be stabilized in accordance with methods known in the art.

In addition to a glucoamylase the composition may further comprise an alpha-amylase. Particularly the alpha-amylase is an acid fungal alpha-amylase. A fungal acid stable alpha-amylase is an alpha-amylase that has activity in the pH range of 3.0 to 7.0 and preferably in the pH range from 3.5 to 6.5, including activity at a pH of about 4.0, 4.5, 5.0, 5.5, and 6.0.

Preferably the acid fungal alpha-amylase is derived from the genus *Aspergillus*, especially a strain of *A. terreus, A. niger, A. oryzae, A. awamori*, or *Aspergillus kawachii*, or from the genus *Rhizomucor*, preferably a strain the *Rhizomucor pusillus*, or the genus *Meripilus*, preferably a strain of *Meripilus giganteus*.

In a preferred embodiment the alpha-amylase is derived from a strain of the genus *Rhizomucor*, preferably a strain the *Rhizomucor pusillus*, such as one shown in SEQ ID NO: 3 in WO 2013/006756, such as a *Rhizomucor pusillus* alpha-amylase hybrid having an *Aspergillus niger* linker and starch-binding domain, such as the one shown in SEQ ID NO: 16 herein, or a variant thereof.

In an embodiment the alpha-amylase is selected from the group consisting of:

(i) an alpha-amylase comprising the polypeptide of SEQ ID NO: 16 herein;

(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 16 herein.

In a preferred embodiment the alpha-amylase is a variant of the alpha-amylase shown in SEQ ID NO: 16 having at least one of the following substitutions or combinations of substitutions: D165M; Y141W; Y141R; K136F; K192R; P224A; P224R; S123H+Y141W; G20S+Y141W; A76G+ Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 16 for numbering).

In an embodiment the alpha-amylase is derived from a *Rhizomucor pusillus* with an *Aspergillus niger* glucoamylase linker and starch-binding domain (SBD), preferably disclosed as SEQ ID NO: 4 herein, preferably having one or more of the following substitutions: G128D, D143N, preferably G128D+D143N (using SEQ ID NO: 4 for numbering), and wherein the alpha-amylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 4 herein.

In a preferred embodiment the ratio between glucoamylase and alpha-amylase present and/or added during saccharification and/or fermentation may preferably be in the range from 500:1 to 1:1, such as from 250:1 to 1:1, such as from 100:1 to 1:1, such as from 100:2 to 100:50, such as from 100:3 to 100:70 gEP/gDS.

The compositions may be prepared in accordance with methods known in the art and may be in the form of a liquid or a dry composition. For instance, the composition may be in the form of granulate or microgranulate. The variant may be stabilized in accordance with methods known in the art.

The compositions may be prepared in accordance with methods known in the art and may be in the form of a liquid or a dry composition. The compositions may be stabilized in accordance with methods known in the art.

The enzyme composition of the present invention may be in any form suitable for use, such as, for example, a crude fermentation broth with or without cells removed, a cell lysate with or without cellular debris, a semi-purified or purified enzyme composition, or a host cell, as a source of the enzymes.

The enzyme composition may be a dry powder or granulate, a non-dusting granulate, a liquid, a stabilized liquid, or a stabilized protected enzyme. Liquid enzyme compositions may, for instance, be stabilized by adding stabilizers such as a sugar, a sugar alcohol or another polyol, and/or lactic acid or another organic acid according to established processes.

Examples are given below of preferred uses of the polypeptide or polypeptide compositions of the invention. The dosage of the polypeptide composition of the invention and other conditions under which the composition is used may be determined on the basis of methods known in the art.

The above compositions are suitable for use in liquefaction, saccharification, and/or fermentation processes, preferably in starch conversion, especially for producing syrup and fermentation products, such as ethanol.

Examples are given below of preferred uses of the polypeptide compositions of the present invention. The dosage of the polypeptide composition of the invention and other conditions under which the composition is used may be determined on the basis of methods known in the art.

Methods of Using the Variant Glucoamylase of the Invention—Industrial Applications The variant glucoamylases of the present invention possess valuable properties allowing for a variety of industrial applications. In particular, the glucoamylases may be used in beer making, ethanol production, and starch conversion processes.

The variant glucoamylases may be used for starch processes, in particular starch conversion, especially liquefaction of starch (see, e.g., U.S. Pat. No. 3,912,590, EP 252730 and EP 063909, WO 99/19467, and WO 96/28567, which are all hereby incorporated by reference). Also contemplated are compositions for starch conversion purposes, which may beside the glucoamylase of the invention also comprise an alpha-amylase, a pullulanase and/or a protease.

Further, the glucoamylases of the invention are particularly useful in the production of sweeteners and ethanol (see, e.g., U.S. Pat. No. 5,231,017, which is hereby incorporated by reference), such as fuel, drinking and industrial ethanol, from starch or whole grains.

In one embodiment the present invention relates to a use of the glucoamylase according to the invention for production of syrup and/or a fermentation product from a starch containing material. The starch material may in one embodiment be gelatinized. In another embodiment the starch material is ungelatinized.

Starch Processing

Native starch consists of microscopic granules, which are insoluble in water at room temperature. When aqueous starch slurry is heated, the granules swell and eventually burst, dispersing the starch molecules into the solution. At temperatures up to about 50° C. to 75° C. the swelling may be reversible. However, with higher temperatures an irreversible swelling called "gelatinization" begins. During this "gelatinization" process there is a dramatic increase in viscosity. Granular starch to be processed may be a highly refined starch quality, preferably at least 90%, at least 95%, at least 97% or at least 99.5% pure or it may be a more crude starch-containing materials comprising (e.g., milled) whole grains including non-starch fractions such as germ residues and fibers. The raw material, such as whole grains, may be reduced in particle size, e.g., by milling, in order to open up the structure and allowing for further processing. In dry milling whole kernels are milled and used. Wet milling gives a good separation of germ and meal (starch granules and protein) and is often applied at locations where the starch hydrolyzate is used in the production of, e.g., syrups. Both dry and wet milling is well known in the art of starch processing and may be used in a process of the invention. Methods for reducing the particle size of the starch containing material are well known to those skilled in the art.

As the solids level is 30-40% in a typical industrial process, the starch has to be thinned or "liquefied" so that it can be suitably processed. This reduction in viscosity is primarily attained by enzymatic degradation in current commercial practice.

Liquefaction is carried out in the presence of an alpha-amylase, preferably a bacterial alpha-amylase and/or acid fungal alpha-amylase. In an embodiment, a phytase is also present during liquefaction. In an embodiment, viscosity reducing enzymes such as a xylanase and/or beta-glucanase is also present during liquefaction.

During liquefaction, the long-chained starch is degraded into branched and linear shorter units (maltodextrins) by an alpha-amylase. Liquefaction may be carried out as a three-step hot slurry process. The slurry is heated to between 60-95° C. (e.g., 70-90° C., such as 77-86° C., 80-85° C., 83-85° C.) and an alpha-amylase is added to initiate liquefaction (thinning).

The slurry may in an embodiment be jet-cooked at between 95-140° C., e.g., 105-125° C., for about 1-15 minutes, e.g., about 3-10 minutes, especially around 5 minutes. The slurry is then cooled to 60-95° C. and more alpha-amylase is added to obtain final hydrolysis (secondary liquefaction). The jet-cooking process is carried out at pH 4.5-6.5, typically at a pH between 5 and 6. The alpha-amylase may be added as a single dose, e.g., before jet cooking.

The liquefaction process is carried out at between 70-95° C., such as 80-90° C., such as around 85° C., for about 10 minutes to 5 hours, typically for 1-2 hours. The pH is between 4 and 7, such as between 5.5 and 6.2. In order to ensure optimal enzyme stability under these conditions, calcium may optionally be added (to provide 1-60 ppm free calcium ions, such as about 40 ppm free calcium ions). After such treatment, the liquefied starch will typically have a "dextrose equivalent" (DE) of 10-15.

Generally liquefaction and liquefaction conditions are well known in the art.

Examples of alpha-amylase are disclosed in the "Alpha-Amylases" section below.

Saccharification may be carried out using conditions well-known in the art with a carbohydrate-source generating enzyme, in particular a glucoamylase, or a beta-amylase and optionally a debranching enzyme, such as an isoamylase or a pullulanase. For instance, a full saccharification step may last from about 24 to about 72 hours. However, it is common to do a pre-saccharification of typically 40-90 minutes at a temperature between 30-65° C., typically about 60° C., followed by complete saccharification during fermentation in a simultaneous saccharification and fermentation (SSF) process. Saccharification is typically carried out at a temperature in the range of 20-75° C., e.g., 25-65° C. and 40-70° C., typically around 60° C., and at a pH between about 4 and 5, normally at about pH 4.5.

The saccharification and fermentation steps may be carried out either sequentially or simultaneously. In an embodiment, saccharification and fermentation are performed simultaneously (referred to as "SSF"). However, it is common to perform a pre-saccharification step for about 30 minutes to 2 hours (e.g., 30 to 90 minutes) at a temperature of 30 to 65° C., typically around 60° C. which is followed by a complete saccharification during fermentation referred to as simultaneous saccharification and fermentation (SSF). The pH is usually between 4.2-4.8, e.g., pH 4.5. In a simultaneous saccharification and fermentation (SSF) process, there is no holding stage for saccharification, rather, the yeast and enzymes are added together.

In a typical saccharification process, maltodextrins produced during liquefaction are converted into dextrose by adding a glucoamylase and a debranching enzyme, such as an isoamylase (U.S. Pat. No. 4,335,208) or a pullulanase. The temperature is lowered to 60° C., prior to the addition of the glucoamylase and debranching enzyme. The saccharification process proceeds for 24-72 hours. Prior to addition of the saccharifying enzymes, the pH is reduced to below 4.5, while maintaining a high temperature (above 95° C.), to inactivate the liquefying alpha-amylase. This process reduces the formation of short oligosaccharide called "panose precursors," which cannot be hydrolyzed properly by the debranching enzyme. Normally, about 0.2-0.5% of the saccharification product is the branched trisaccharide panose (Glc pα1-6Glc pα1-4Glc), which cannot be degraded by a pullulanase. If active amylase from the liquefaction remains present during saccharification (i.e., no denaturing), the amount of panose can be as high as 1-2%, which is highly undesirable since it lowers the saccharification yield significantly.

Other fermentation products may be fermented at conditions and temperatures well known to persons skilled in the art, suitable for the fermenting organism in question.

The fermentation product may be recovered by methods well known in the art, e.g., by distillation. Examples of carbohydrate-source generating enzymes are disclosed in the "Enzymes" section below.

In a particular embodiment, the process of the invention further comprises, prior to the conversion of a starch-containing material to sugars/dextrins the steps of:

(x) reducing the particle size of the starch-containing material; and (y) forming a slurry comprising the starch-containing material and water.

In an embodiment, the starch-containing material is milled to reduce the particle size. In an embodiment the particle size is reduced to between 0.05-3.0 mm, preferably 0.1-0.5 mm, or so that at least 30%, preferably at least 50%, more preferably at least 70%, even more preferably at least 90% of the starch-containing material fits through a sieve with a 0.05-3.0 mm screen, preferably 0.1-0.5 mm screen.

The aqueous slurry may contain from 10-55 wt. % dry solids (DS), preferably 25-45 wt. % dry solids (DS), more preferably 30-40 wt. % dry solids (DS) of starch-containing material.

Conventional starch-conversion processes, such as liquefaction and saccharification processes are described, e.g., in U.S. Pat. No. 3,912,590, EP 252730 and EP 063909, which are incorporated herein by reference.

In an embodiment, the conversion process degrading starch to lower molecular weight carbohydrate components such as sugars or fat replacers includes a debranching step.

In the case of converting starch into a sugar, the starch is depolymerized. Such a depolymerization process consists of, e.g., a pre-treatment step and two or three consecutive process steps, i.e., a liquefaction process, a saccharification process, and depending on the desired end-product, an optional isomerization process.

When the desired final sugar product is, e.g., high fructose syrup the dextrose syrup may be converted into fructose. After the saccharification process, the pH is increased to a value in the range of 6-8, e.g., pH 7.5, and the calcium is removed by ion exchange. The dextrose syrup is then converted into high fructose syrup using, e.g., an immobilized glucose isomerase.

Production of Fermentation Products

Fermentable sugars (e.g., dextrins, monosaccharides, particularly glucose) are produced from enzymatic saccharification. These fermentable sugars may be further purified and/or converted to useful sugar products. In addition, the sugars may be used as a fermentation feedstock in a microbial fermentation process for producing end-products, such as alcohol (e.g., ethanol, and butanol), organic acids (e.g., succinic acid, 3-HP and lactic acid), sugar alcohols (e.g., glycerol), ascorbic acid intermediates (e.g., gluconate, 2-keto-D-gluconate, 2,5-diketo-D-gluconate, and 2-keto-L-gulonic acid), amino acids (e.g., lysine), proteins (e.g., antibodies and fragment thereof).

In an embodiment, the fermentable sugars obtained during the liquefaction process steps are used to produce alcohol and particularly ethanol. In ethanol production, an SSF process is commonly used wherein the saccharifying enzymes and fermenting organisms (e.g., yeast) are added together and then carried out at a temperature of 30-40° C.

The organism used in fermentation will depend on the desired end-product. Typically, if ethanol is the desired end product yeast will be used as the fermenting organism. In some preferred embodiments, the ethanol-producing microorganism is a yeast and specifically *Saccharomyces* such as strains of *S. cerevisiae* (U.S. Pat. No. 4,316,956). A variety of *S. cerevisiae* are commercially available and these include but are not limited to FALI (Fleischmann's Yeast), SUPERSTART (Alltech), FERMIOL (DSM Specialties), RED STAR (Lesaffre) and Angel alcohol yeast (Angel Yeast Company, China). The amount of starter yeast employed in the methods is an amount effective to produce a commercially significant amount of ethanol in a suitable amount of time, (e.g., to produce at least 10% ethanol from a substrate having between 25-40% DS in less than 72 hours). Yeast cells are generally supplied in amounts of about $10^4$ to about $10^{12}$, and preferably from about $10^7$ to about $10^{10}$ viable yeast count per mL of fermentation broth. After yeast is added to the mash, it is typically subjected to fermentation for about 24-96 hours, e.g., 35-60 hours. The temperature is between about 26-34° C., typically at about 32° C., and the pH is from pH 3-6, e.g., around pH 4-5.

The fermentation may include, in addition to a fermenting microorganisms (e.g., yeast), nutrients, and additional enzymes, including phytases. The use of yeast in fermentation is well known in the art.

In further embodiments, use of appropriate fermenting microorganisms, as is known in the art, can result in fermentation end product including, e.g., glycerol, 1,3-propanediol, gluconate, 2-keto-D-gluconate, 2,5-diketo-D-gluconate, 2-keto-L-gulonic acid, succinic acid, lactic acid, amino acids, and derivatives thereof. More specifically when lactic acid is the desired end product, a *Lactobacillus* sp. (*L. casei*) may be used; when glycerol or 1,3-propanediol are the desired end-products *E. coli* may be used; and when 2-keto-D-gluconate, 2,5-diketo-D-gluconate, and 2-keto-L-gulonic acid are the desired end products, *Pantoea citrea* may be used as the fermenting microorganism. The above enumerated list are only examples and one skilled in the art will be aware of a number of fermenting microorganisms that may be used to obtain a desired end product.

Processes for Producing Fermentation Products from Ungelatinized Starch-Containing Material The invention relates to processes for producing fermentation products from starch-containing material without gelatinization (i.e., without cooking) of the starch-containing material (often referred to as a "raw starch hydrolysis" process). The fermentation product, such as ethanol, can be produced without liquefying the aqueous slurry containing the starch-containing material and water. In one embodiment a process of the invention includes saccharifying (e.g., milled) starch-containing material, e.g., granular starch, below the initial gelatinization temperature, preferably in the presence of alpha-amylase and/or carbohydrate-source generating enzyme(s) to produce sugars that can be fermented into the fermentation product by a suitable fermenting organism. In this embodiment the desired fermentation product, e.g., ethanol, is produced from ungelatinized (i.e., uncooked), preferably milled, cereal grains, such as corn.

Accordingly, in one aspect the invention relates to processes for producing fermentation products from starch-containing material comprising simultaneously saccharifying and fermenting starch-containing material using a carbohydrate-source generating enzyme and a fermenting organism at a temperature below the initial gelatinization temperature of said starch-containing material. Saccharification and fermentation may also be separate. Thus in another aspect the invention relates to processes of producing fermentation products, comprising the following steps:

(i) saccharifying a starch-containing material at a temperature below the initial gelatinization temperature; and (ii) fermenting using a fermentation organism;

wherein step (i) is carried out using at least a variant glucoamylase of the invention.

In one embodiment, an alpha amylase is added in step (i). In another embodiment steps (i) and (ii) are performed simultaneously.

In one embodiment, a protease is also present. The protease may be any acid fungal protease or metalloprotease. The fermentation product, e.g., ethanol, may optionally be recovered after fermentation, e.g., by distillation. Typically amylase(s), such as glucoamylase(s) and/or other carbohydrate-source generating enzymes, and/or alpha-amylase(s), is(are) present during fermentation. Examples of glucoamylases and other carbohydrate-source generating enzymes include raw starch hydrolyzing glucoamylases. Examples of alpha-amylase(s) include acid alpha-amylases such as acid fungal alpha-amylases. Examples of fermenting organisms include yeast, e.g., a strain of *Saccharomyces cerevisiae*. The term "initial gelatinization temperature" means the lowest temperature at which starch gelatinization commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material may be determined as the temperature at which birefringence is lost in 5% of the starch granules using the method described by Gorinstein and Lii, 1992, *Starch/Stärke* 44(12): 461-466. Before initiating the process a slurry of starch-containing material, such as granular starch, having 10-55 w/w % dry solids (DS), preferably 25-45 w/w % dry solids, more preferably 30-40 w/w % dry solids of starch-containing material may be prepared. The slurry may include water and/or process waters, such as stillage (backset), scrubber water, evaporator condensate or distillate, side-stripper water from distillation, or process water from other fermentation product plants. Because the process of the invention is carried out below the initial gelatinization temperature, and thus no significant viscosity increase takes place, high levels of stillage may be used if desired. In an embodiment the aqueous slurry contains from about 1 to about 70 vol. %, preferably 15-60 vol. %, especially from about 30 to 50 vol. % water and/or process waters, such as stillage (backset), scrubber water, evaporator condensate or distillate, side-stripper water from distillation, or process water from other fermentation product plants, or combinations thereof, or the like. The starch-containing material may be prepared by reducing the particle size, preferably by dry or wet milling, to 0.05 to 3.0 mm, preferably 0.1-0.5 mm. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids in the starch-containing material are converted into a soluble starch hydrolyzate. A process of the invention is conducted at a temperature below the initial gelatinization temperature, which means that the temperature typically lies in the range between 30-75° C., preferably between 45-60° C. In a preferred embodiment the process carried at a temperature from 25° C. to 40° C., such as from 28° C. to 35° C., such as from 30° C. to 34° C., preferably around 32° C. In an embodiment the process is carried out so that the sugar level, such as glucose level, is kept at a low level, such as below 6 w/w %, such as below about 3 w/w %, such as below about 2 w/w %, such as below about 1 w/w %., such as below about 0.5 w/w %, or below 0.25 w/w %, such as below about 0.1 w/w %. Such low levels of sugar can be accomplished by simply employing adjusted quantities of enzyme and fermenting organism. A skilled person in the art can easily determine which doses/quantities of enzyme and fermenting organism to use. The employed quantities of enzyme and fermenting organism may also be selected to maintain low concentrations of maltose in the fermentation broth. For instance, the maltose level may be kept below about 0.5 w/w %, such as below about 0.2 w/w %. The process of the invention may be carried out at a pH from about 3 and 7, preferably from pH 3.5 to 6, or more preferably from pH 4 to 5. In an embodiment fermentation is ongoing for 6 to 120 hours, in particular 24 to 96 hours.

Processes for Producing Fermentation Products from Gelatinized Starch-Containing Material In this aspect, the invention relates to processes for producing fermentation products, especially ethanol, from starch-containing material, which process includes a liquefaction step and sequentially or simultaneously performed saccharification and fermentation steps. Consequently, the invention relates to processes for producing fermentation products from starch-containing material comprising the steps of:

(a) liquefying starch-containing material in the presence of an alpha-amylase;

(b) saccharifying the liquefied material obtained in step (a) using a glucoamylase;

(c) fermenting using a fermenting organism;

wherein step (a) and/or step (b) is carried out in the presence of a glucoamylase according to the invention.

In an embodiment, a protease, such as an acid fungal protease or a metallo protease is added before, during and/or after liquefaction. In an embodiment the metalloprotease is derived from a strain of *Thermoascus*, e.g., a strain of *Thermoascus aurantiacus*, especially *Thermoascus aurantiacus* CGMCC No. 0670. In another embodiment the protease is a bacterial protease, particularly a protease derived from a strain of *Pyrococcus*, more particularly from *Pyrococcus furiosus* disclosed in U.S. Pat. No. 6,358,726.

A further glucoamylase may be added. In an embodiment the further glucoamylase is derived from a strain of *Aspergillus*, e.g., *Aspergillus niger* or *Aspergillus awamori*, a strain of *Talaromyces*, especially *Talaromyces emersonii*; or a strain of *Athelia*, especially *Athelia rolfsii*; a strain of *Trametes*, e.g., *Trametes cingulata*; a strain of the genus *Gloeophyllum*, e.g., a strain of *Gloeophyllum sepiarum* or *Gloeophyllum trabeum*; or a mixture thereof. Saccharification step (b) and fermentation step (c) may be carried out either sequentially or simultaneously. A pullulanase and/or a metalloprotease may be added during saccharification and/or fermentation when the process is carried out as a sequential saccharification and fermentation process and before or during fermentation when steps (b) and (c) are carried out simultaneously (SSF process). The pullulanase and/or the metalloprotease may also advantageously be added before liquefaction (pre-liquefaction treatment), i.e., before or during step (a), and/or after liquefaction (post liquefaction treatment), i.e., after step (a). The pullulanase is most advantageously added before or during liquefaction, i.e., before or during step (a). The fermentation product, such as especially ethanol, may optionally be recovered after fermentation, e.g., by distillation. The fermenting organism is preferably yeast, preferably a strain of *Saccharomyces cerevisiae*. In a particular embodiment, the process of the invention further comprises, prior to step (a), the steps of:

x) reducing the particle size of the starch-containing material, preferably by milling (e.g., using a hammer mill);

y) forming a slurry comprising the starch-containing material and water.

In an embodiment, the particle size is smaller than a #7 screen, e.g., a #6 screen. A #7 screen is usually used in conventional prior art processes. The aqueous slurry may contain from 10-55, e.g., 25-45 and 30-40, w/w % dry solids (DS) of starch-containing material. The slurry is heated to above the gelatinization temperature and an alpha-amylase variant may be added to initiate liquefaction (thinning). The slurry may in an embodiment be jet-cooked to further gelatinize the slurry before being subjected to alpha-amylase in step (a). Liquefaction may in an embodiment be carried out as a three-step hot slurry process. The slurry is heated to between 60-95° C., preferably between 70-90° C., such as preferably between 80-85° C. at pH 4-6, preferably 4.5-5.5, and alpha-amylase variant, optionally together with a pullulanase and/or protease, preferably metalloprotease, are added to initiate liquefaction (thinning). In an embodiment the slurry may then be jet-cooked at a temperature between 95-140° C., preferably 100-135° C., such as 105-125° C., for about 1-15 minutes, preferably for about 3-10 minutes, especially around about 5 minutes. The slurry is cooled to 60-95° C. and more alpha-amylase and optionally pullulanase and/or protease, preferably metalloprotease, is(are) added to finalize hydrolysis (secondary liquefaction). The liquefaction process is usually carried out at pH 4.0-6, in particular at a pH from 4.5 to 5.5. Saccharification step (b) may be carried out using conditions well known in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at temperatures from 20-75° C., preferably from 40-70° C., typically around 60° C., and at a pH between 4 and 5, normally at about pH 4.5. The most widely used process to produce a fermentation product, especially ethanol, is a simultaneous saccharification and fermentation (SSF) process, in which there is no holding stage for the saccharification, meaning that a fermenting organism, such as yeast, and enzyme(s), may be added together. SSF may typically be carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours.

Starch-Containing Materials

Any suitable starch-containing starting material may be used in a process of the present invention. The starting material is generally selected based on the desired fermentation product. Examples of starch-containing starting materials, suitable for use in the processes of the present invention, include barley, beans, cassava, cereals, corn, milo, peas, potatoes, rice, rye, sago, sorghum, sweet potatoes, tapioca, wheat, and whole grains, or any mixture thereof. The starch-containing material may also be a waxy or non-waxy type of corn and barley. In a preferred embodiment the starch-containing material is corn. In a preferred embodiment the starch-containing material is wheat.

Fermentation Products

The term "fermentation product" means a product produced by a method or process including fermenting using a fermenting organism. Fermentation products include alcohols (e.g., ethanol, methanol, butanol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. In a preferred embodiment the fermentation product is ethanol.

Beer Making

The glucoamylase variants may also be used in a beer-making process and similar fermentations. The process is substantially similar to the milling, liquefaction, saccharification, and fermentation processes described above.

Starch Slurry Processing with Stillage

Milled starch-containing material is combined with water and recycled thin-stillage resulting in an aqueous slurry. The slurry can comprise between 15 to 55% ds w/w (e.g., 20 to 50%, 25 to 50%, 25 to 45%, 25 to 40%, 20 to 35% and 30-36% ds). In some embodiments, the recycled thin-stillage (backset) is in the range of about 10 to 70% v/v (e.g., 10 to 60%, 10 to 50%, 10 to 40%, 10 to 30%, 10 to 20%, 20 to 60%, 20 to 50%, 20 to 40% and also 20 to 30%).

Once the milled starch-containing material is combined with water and backset, the pH is not adjusted in the slurry. Further the pH is not adjusted after the addition of a phytase and optionally an alpha-amylase to the slurry. In an embodiment, the pH of the slurry will be in the range of about pH 4.5 to less than about 6.0 (e.g., pH 4.5 to 5.8, pH 4.5 to 5.6, pH 4.8 to 5.8, pH 5.0 to 5.8, pH 5.0 to 5.4, pH 5.2 to 5.5 and pH 5.2 to 5.9). The pH of the slurry may be between about pH 4.5 and 5.2 depending on the amount of thin stillage added to the slurry and the type of material comprising the thin stillage. For example, the pH of the thin stillage may be between pH 3.8 and pH 4.5.

During ethanol production, acids can be added to lower the pH in the beer well, to reduce the risk of microbial contamination prior to distillation.

In some embodiments, a phytase is added to the slurry. In other embodiments, in addition to phytase, an alpha-amylase is added to the slurry. In some embodiments, a phytase and alpha-amylase are added to the slurry sequentially. In other embodiments, a phytase and alpha-amylase are added simultaneously. In some embodiments, the slurry comprising a phytase and optionally, an alpha-amylase, are incubated (pretreated) for a period of about 5 minutes to about 8 hours (e.g., 5 minutes to 6 hours, 5 minutes to 4 hours, 5 minutes to 2 hours, and 15 minutes to 4 hours). In other embodiments, the slurry is incubated at a temperature in the range of about 40 to 115° C. (e.g., 45 to 80° C., 50 to 70° C., 50 to 75° C., 60 to 110° C., 60 to 95° C., 70 to 110° C., 70 to 85° C. and 77 to 86° C.).

In other embodiments, the slurry is incubated at a temperature of about 0 to about 30° C. (e.g., 0 to 25° C., 0 to 20° C., 0 to 15° C., 0 to 10° C. and 0 to 5° C.) below the starch gelatinization temperature of the starch-containing material. In some embodiments, the temperature is below about 68° C., below about 65° C., below about 62° C., below about 60° C. and below about 55° C. In some embodiments, the temperature is above about 45° C., above about 50° C., above about 55° C. and above about 60° C. In some embodiments, the incubation of the slurry comprising a phytase and an alpha-amylase at a temperature below the starch gelatinization temperature is referred to as a primary (1°) liquefaction.

In one embodiment, the milled starch-containing material is corn or milo. The slurry comprises 25 to 40% DS, the pH is in the range of 4.8 to 5.2, and the slurry is incubated with a phytase and optionally an alpha-amylase for 5 minutes to 2 hours, at a temperature range of 60 to 75° C.

Currently, it is believed that commercially-available microbial alpha-amylases used in the liquefaction process are generally not stable enough to produce liquefied starch substrate from a dry mill process using whole ground grain at a temperature above about 80° C. at a pH level that is less than pH 5.6. The stability of many commercially available alpha-amylases is reduced at a pH of less than about 4.0.

In a further liquefaction step, the incubated or pretreated starch-containing material is exposed to an increase in temperature such as about 0 to about 45° C. above the starch gelatinization temperature of the starch-containing material (e.g., 70° C. to 120° C., 70° C. to 110° C., and 70° C. to 90° C.) for a period of time of about 2 minutes to about 6 hours (e.g., 2 minutes to 4 hours, 90 minutes, 140 minutes and 90 to 140 minutes) at a pH of about 4.0 to 5.5 more preferably between 1 hour to 2 hours. The temperature can be increased by a conventional high temperature jet cooking system for a short period of time, for example, for 1 to 15 minutes. Then the starch maybe further hydrolyzed at a temperature ranging from about 75° C. to 95° C. (e.g., 80° C. to 90° C. and 80° C. to 85° C.) for a period of about 15 to 150 minutes (e.g., 30 to 120 minutes). In a preferred embodiment, the pH is not adjusted during these process steps and the pH of the liquefied mash is in the range of about pH 4.0 to pH 5.8 (e.g., pH 4.5 to 5.8, pH 4.8 to 5.4, and pH 5.0 to 5.2). In some embodiments, a second dose of thermostable alpha-amylase is added to the secondary liquefaction step, but in other embodiments there is no additional dosage of alpha-amylase.

The incubation and liquefaction steps may be followed by saccharification and fermentation steps well known in the art.

Distillation

Optionally, following fermentation, an alcohol (e.g., ethanol) may be extracted by, for example, distillation and optionally followed by one or more process steps.

In some embodiments, the yield of ethanol produced by the methods provided herein is at least 8%, at least 10%, at least 12%, at least 14%, at least 15%, at least 16%, at least 17% and at least 18% (v/v) and at least 23% v/v. The ethanol obtained according to the process provided herein may be used as, for example, fuel ethanol, drinking ethanol, i.e., potable neutral spirits, or industrial ethanol.

By-Products

Left over from the fermentation is the distiller's grain, which is typically used for animal feed either in liquid or dried form. In further embodiments, the end product may include the fermentation co-products such as distiller's dried grains (DDG) and distiller's dried grain plus solubles (DDGS), which may be used, for example, as an animal feed.

Further details on how to carry out liquefaction, saccharification, fermentation, distillation, and recovery of ethanol are well known to the skilled person.

According to the process provided herein, the saccharification and fermentation may be carried out simultaneously or separately.

Fermenting Organisms

The term "fermenting organism" refers to any organism, including bacterial and fungal organisms, such as yeast and filamentous fungi, suitable for producing a desired fermentation product. Suitable fermenting organisms are able to ferment, i.e., convert, fermentable sugars, such as arabinose, fructose, glucose, maltose, mannose, or xylose, directly or indirectly into the desired fermentation product.

Examples of fermenting organisms include fungal organisms such as yeast. Preferred yeast include strains of *Saccharomyces*, in particular *Saccharomyces cerevisiae* or *Saccharomyces uvarum*; strains of *Pichia*, in particular *Pichia stipitis* such as *Pichia stipitis* CBS 5773 or *Pichia pastoris*; strains of *Candida*, in particular *Candida arabinofermentans*, *Candida boidinii*, *Candida diddensii*, *Candida shehatae*, *Candida sonorensis*, *Candida tropicalis*, or *Candida utilis*. Other fermenting organisms include strains of *Hansenula*, in particular *Hansenula anomala* or *Hansenula polymorpha*; strains of *Kluyveromyces*, in particular *Kluyveromyces fragilis* or *Kluyveromyces marxianus*; and strains of *Schizosaccharomyces*, in particular *Schizosaccharomyces pombe*.

Preferred bacterial fermenting organisms include strains of *Escherichia*, in particular *Escherichia coli*, strains of *Zymomonas*, in particular *Zymomonas mobilis*, strains of *Zymobacter*, in particular *Zymobactor palmae*, strains of *Klebsiella* in particular *Klebsiella oxytoca*, strains of *Leuconostoc*, in particular *Leuconostoc mesenteroides*, strains of *Clostridium*, in particular *Clostridium butyricum*, strains of *Enterobacter*, in particular *Enterobacter aerogenes*, and strains of *Thermoanaerobacter*, in particular *Thermoanaerobacter* BG1L1 (*Appl. Microbiol. Biotech.* 77: 61-86), *Thermoanarobacter ethanolicus*, *Thermoanaerobacter mathranii*, or *Thermoanaerobacter thermosaccharolyticum*. Strains of *Lactobacillus* are also envisioned as are strains of *Corynebacterium glutamicum* R, *Bacillus thermoglucosidaisus*, and *Geobacillus thermoglucosidasius*.

In an embodiment, the fermenting organism is a C6 sugar fermenting organism, such as a strain of, e.g., *Saccharomyces cerevisiae*.

In an embodiment, the fermenting organism is a C5 sugar fermenting organism, such as a strain of, e.g., *Saccharomyces cerevisiae*.

In one embodiment, the fermenting organism is added to the fermentation medium so that the viable fermenting organism, such as yeast, count per mL of fermentation medium is in the range from $10^5$ to $10^{12}$, preferably from $10^7$ to $10^{10}$, especially about $5 \times 10^7$.

Yeast is the preferred fermenting organism for ethanol fermentation. Preferred are strains of *Saccharomyces*, especially strains of the species *Saccharomyces cerevisiae*, preferably strains which are resistant towards high levels of ethanol, i.e., up to, e.g., about 10, 12, 15 or 20 vol. % or more ethanol.

In an embodiment, the C5 utilizing yeast is a *Saccharomyces cerevisea* strain disclosed in WO 2004/085627.

In an embodiment, the fermenting organism is a C5 eukaryotic microbial cell concerned in WO 2010/074577 (Nedalco).

In an embodiment, the fermenting organism is a transformed C5 eukaryotic cell capable of directly isomerize xylose to xylose disclosed in US 2008/0014620.

In an embodiment, the fermenting organism is a C5 sugar fermentating cell disclosed in WO 2009/109633.

Commercially available yeast include LNF SA-1, LNF BG-1, LNF PE-2, and LNF CAT-1 (available from LNF Brazil), RED START™ and ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

The fermenting organism capable of producing a desired fermentation product from fermentable sugars is preferably grown under precise conditions at a particular growth rate. When the fermenting organism is introduced into/added to the fermentation medium the inoculated fermenting organism pass through a number of stages. Initially growth does not occur. This period is referred to as the "lag phase" and may be considered a period of adaptation. During the next phase referred to as the "exponential phase" the growth rate gradually increases. After a period of maximum growth the rate ceases and the fermenting organism enters "stationary phase". After a further period of time the fermenting organism enters the "death phase" where the number of viable cells declines.

Fermentation

The fermentation conditions are determined based on, e.g., the kind of plant material, the available fermentable sugars, the fermenting organism(s) and/or the desired fermentation product. One skilled in the art can easily determine suitable fermentation conditions. The fermentation may be carried out at conventionally used conditions. Preferred fermentation processes are anaerobic processes.

For example, fermentations may be carried out at temperatures as high as 75° C., e.g., between 40-70° C., such as between 50-60° C. However, bacteria with a significantly lower temperature optimum down to around room temperature (around 20° C.) are also known. Examples of suitable fermenting organisms can be found in the "Fermenting Organisms" section above.

For ethanol production using yeast, the fermentation may go on for 24 to 96 hours, in particular for 35 to 60 hours. In an embodiment the fermentation is carried out at a temperature between 20 to 40° C., preferably 26 to 34° C., in particular around 32° C. In an embodiment the pH is from pH 3 to 6, preferably around pH 4 to 5.

Other fermentation products may be fermented at temperatures known to the skilled person in the art to be suitable for the fermenting organism in question.

Fermentation is typically carried out at a pH in the range between 3 and 7, preferably from pH 3.5 to 6, such as around pH 5. Fermentations are typically ongoing for 6-96 hours.

The processes of the invention may be performed as a batch or as a continuous process. Fermentations may be conducted in an ultrafiltration system wherein the retentate is held under circulation in the presence of solids, water, and the fermenting organism, and wherein the permeate is the desired fermentation product containing liquid. Equally contemplated are methods/processes conducted in continuous membrane reactors with ultrafiltration membranes and where the retentate is held under circulation in presence of solids, water, and the fermenting organism(s) and where the permeate is the fermentation product containing liquid.

After fermentation the fermenting organism may be separated from the fermented slurry and recycled.

Fermentation Medium

The phrase "fermentation media" or "fermentation medium" refers to the environment in which fermentation is carried out and comprises the fermentation substrate, that is, the carbohydrate source that is metabolized by the fermenting organism(s).

The fermentation medium may comprise other nutrients and growth stimulator(s) for the fermenting organism(s). Nutrient and growth stimulators are widely used in the art of fermentation and include nitrogen sources, such as ammonia; vitamins and minerals, or combinations thereof.

Recovery

Subsequent to fermentation, the fermentation product may be separated from the fermentation medium. The fermentation medium may be distilled to extract the desired fermentation product or the desired fermentation product may be extracted from the fermentation medium by micro or membrane filtration techniques. Alternatively, the fermentation product may be recovered by stripping. Methods for recovery are well known in the art.

Enzymes

The enzyme(s) and polypeptides described below are to be used in an "effective amount" in processes of the present invention.

Alpha-Amylases

Any alpha-amylase may be used, such as of fungal, bacterial or plant origin. In a preferred embodiment the alpha-amylase is an acid alpha-amylase, e.g., acid fungal or acid bacterial alpha-amylase. The term "acid alpha-amylase" means an alpha-amylase (EC 3.2.1.1) which added in an effective amount has activity optimum at a pH in the range of 3 to 7, preferably from 3.5 to 6, or more preferably from 4-5.

Bacterial Alpha-Amylases

An alpha-amylase for use in the present invention may be a bacterial alpha-amylase, e.g., derived from *Bacillus*. In a preferred embodiment the *Bacillus* alpha-amylase is derived from a strain of *Bacillus amyloliquefaciens, Bacillus licheniformis, Bacillus stearothermophilus*, or *Bacillus subtilis*, but may also be derived from other *Bacillus* sp.

Specific examples of alpha-amylases include the *Bacillus amyloliquefaciens* alpha-amylase of SEQ ID NO: 5 in WO 99/19467, the *Bacillus licheniformis* alpha-amylase of SEQ ID NO: 4 in WO 99/19467, and the *Bacillus stearothermophilus* alpha-amylase of SEQ ID NO: 3 in WO 99/19467 (all sequences are hereby incorporated by reference). In an embodiment the alpha-amylase may be an enzyme having a degree of identity of at least 60%, e.g., at least 70%, at least 80%, at least 90%, at least 95%, at least 96%, at least 97%, at least 98% or at least 99% to any of the sequences shown in SEQ ID NOS: 3, 4 or 5, respectively, in WO 99/19467.

The *Bacillus* alpha-amylase may also be a variant and/or hybrid, especially one described in any of WO 96/23873, WO 96/23874, WO 97/41213, WO 99/19467, WO 00/60059, and WO 02/10355 (all documents are hereby incorporated by reference). Specific alpha-amylase variants are disclosed in U.S. Pat. Nos. 6,093,562, 6,187,576, and 6,297,038 (hereby incorporated by reference) and include *Bacillus stearothermophilus* alpha-amylase (BSG alpha-amylase) variants having a deletion of one or two amino acids at positions R179 to G182, preferably a double deletion disclosed in WO 96/23873—see, e.g., page 20, lines 1-10 (hereby incorporated by reference), preferably corresponding to delta(181-182) compared to the amino acid sequence of *Bacillus stearothermophilus* alpha-amylase set forth in SEQ ID NO: 3 disclosed in WO 99/19467 or the deletion of amino acids R179 and G180 using SEQ ID NO: 3 in WO 99/19467 for numbering (which reference is hereby incorporated by reference). In a preferred embodiment the alpha-amylase is derived from *Bacillus stearothermophilus*. The *Bacillus stearothermophilus* alpha-amylase may be a mature wild-type or a mature variant thereof. The mature *Bacillus stearothermophilus* alpha-amylases may naturally be truncated during recombinant production. For instance, the *Bacillus stearothermophilus* alpha-amylase may be truncated so it has around 491 amino acids (compared to SEQ ID NO: 3 in WO 99/19467. Preferred are *Bacillus* alpha-amylases, especially *Bacillus stearothermophilus* alpha-amylases, which have a double deletion corresponding to a deletion of positions 181 and 182 and further comprise a N193F substitution (also denoted I181*+G182*+N193F) compared to the wild-type BSG alpha-amylase amino acid sequence set forth in SEQ ID NO: 3 disclosed in WO 99/19467. The bacterial alpha-amylase may also have a substitution in a position corresponding to S239 in the *Bacillus licheniformis* alpha-amylase shown in SEQ ID NO: 4 in WO 99/19467, or a S242 variant of the *Bacillus stearothermophilus* alpha-amylase of SEQ ID NO: 3 in WO 99/19467. In a preferred embodiment the alpha-amylase is selected from the group of *Bacillus stearomthermphilus* alpha-amylase variants:

I181*+G182*+N193F+E129V+K177L+R179E;

I181*+G182*+N193F+V59A+Q89R+E129V+K177L+ R179E+H208Y+K220P+N224L+Q2 54S;

I181*+G182*+N193F+V59A+Q89R+E129V+K177L+ R179E+Q254S+M284V; and

I181*+G182*+N193F+E129V+K177L+R179E+K220P+ N224L+S242Q+Q254S (using SEQ ID NO: 3 disclosed in WO 99/19467 for numbering).

Bacterial Hybrid Alpha-Amylases

The alpha-amylase may be a hybrid alpha-amylase, e.g., an alpha-amylase comprising 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467), with one or more, especially all, of the following substitutions:

G48A+T49I+G107A+H156Y+A181T+N190F+I201F+ A209V+Q264S (using the *Bacillus licheniformis* numbering in SEQ ID NO: 4 of WO 99/19467). Also preferred are variants having one or more of the following mutations (or corresponding mutations in other *Bacillus* alpha-amylases): H154Y, A181T, N190F, A209V and Q264S and/or the deletion of two residues between positions 176 and 179, preferably the deletion of E178 and G179 (using SEQ ID NO: 5 of WO 99/19467 for position numbering).

Fungal Alpha-Amylases

Fungal alpha-amylases include alpha-amylases derived from a strain of *Aspergillus*, such as, *Aspergillus kawachii*, *Aspergillus niger* and *Aspergillus oryzae* alpha-amylases.

A preferred acidic fungal alpha-amylase is an alpha-amylase which exhibits a high identity, i.e., at least 70%, at least 75%, at least 80%, at least 85%, at least 90%, at least 95%, at least 96%, at least 97%, at least 98%, at least 99% or even 100% identity to the mature part of the amino acid sequence shown in SEQ ID NO: 10 in WO 96/23874.

Another preferred acid alpha-amylase is derived from a strain of *Aspergillus niger*. In a preferred embodiment the acid fungal alpha-amylase is an *Aspergillus niger* alpha-amylase disclosed as "AMYA_ASPNG" in the Swiss-prot/ TeEMBL database under the primary accession no. P56271 and described in WO 89/01969 (Example 3—incorporated by reference).

Other wild-type alpha-amylases include those derived from a strain of *Meripilus* and *Rhizomucor*, preferably a strain of *Meripilus giganteus* or *Rhizomucor pusillus* (WO 2004/055178 which is incorporated herein by reference).

In another preferred embodiment the alpha-amylase is derived from *Aspergillus terreus*.

In a preferred embodiment, the alpha-amylase is derived from *Aspergillus kawachii* (Kaneko et al., 1996, *J. Ferment. Bioeng.* 81: 292-298, "Molecular-cloning and determination of the nucleotide-sequence of a gene encoding an acid-stable alpha-amylase from *Aspergillus kawachii*"; and further as EMBL: #AB008370).

The fungal alpha-amylase may also be a wild-type enzyme comprising a starch-binding domain (SBD) and an alpha-amylase catalytic domain, or a variant thereof.

Fungal Hybrid Alpha-Amylases

In a preferred embodiment, the fungal acid alpha-amylase is a hybrid alpha-amylase. Examples of fungal hybrid alpha-amylases include the ones disclosed in WO 2005/003311, U.S. Patent Application Publication No. 2005/0054071 (Novozymes), and WO 2006/069290 (Novozymes), which are hereby incorporated by reference. A hybrid alpha-amylase may comprise an alpha-amylase catalytic domain (CD) and a carbohydrate-binding domain/module (CBM), such as a starch binding domain (SBD), and optionally a linker.

Examples of hybrid alpha-amylases include those disclosed in Tables 1 to 5 of the examples in WO 2006/069290 including the variant with the catalytic domain JA118 and *Athelia rolfsii* SBD (SEQ ID NO: 100 in WO 2006/069290), *Rhizomucor pusillus* alpha-amylase with *Athelia rolfsii* AMG linker and SBD (SEQ ID NO: 101 in WO 2006/ 069290), *Rhizomucor pusillus* alpha-amylase with *Aspergillus niger* glucoamylase linker and SBD (which is disclosed in Table 5 as a combination of amino acid sequences SEQ ID NO: 20, SEQ ID NO: 72 and SEQ ID NO: 96 in U.S. application Ser. No. 11/316,535) or as V039 in Table 5 in WO 2006/069290, and *Meripilus giganteus* alpha-amylase with *Athelia rolfsii* glucoamylase linker and SBD (SEQ ID NO: 102 in WO 2006/069290). Other hybrid alpha-amylases are listed in Tables 3, 4, 5, and 6 in Example 4 in U.S. application Ser. No. 11/316,535 and WO 2006/069290 (which are hereby incorporated by reference).

In a preferred embodiment the alpha-amylase is an alpha-amylase derived from *Rhizomucor pusillus* with an *Aspergillus niger* glucoamylase linker and starch-binding domain (SBD), preferably the one shown in SEQ ID NO: 7 in WO2013/006756, preferably having one or more of the following substitutions: G128D, D143N, especially G128D+D143N.

Other examples of hybrid alpha-amylases include those disclosed in U.S. Patent Application Publication No. 2005/ 0054071, including those disclosed in Table 3 on page 15, such as *Aspergillus niger* alpha-amylase with *Aspergillus kawachii* linker and starch binding domain.

Other alpha-amylases exhibit a high degree of sequence identity to any of above mentioned alpha-amylases, i.e., at least 70%, at least 75%, at least 80%, at least 85%, at least 90%, at least 95%, at least 96%, at least 97%, at least 98%, at least 99% or even 100% identity to the mature enzyme sequences disclosed above.

Commercial Alpha-Amylase Products

Preferred commercial compositions comprising alpha-amylase include MYCOLASE™ (DSM), BAN™, TER- MAMYL™ SC, FUNGAMYL™, LIQUOZYME™ X, LIQUOZYME™ SC and SAN™ SUPER, SAN™ EXTRA L (Novozymes NS) and CLARASE™ L-40,000, DEXLO™, SPEZYME™ FRED, SPEZYME™ AA, SPEZYME™ ALPHA, SPEZYME™ DELTA AA, GC358, GC980, SPEZYME™ CL and SPEZYME™ RSL (DuPont Industrial Biosciences), and the acid fungal alpha-amylase from *Aspergillus niger* referred to as SP288 (available from Novozymes NS, Denmark).

Carbohydrate-Source Generating Enzymes (Saccharifying Enzymes) The term "carbohydrate-source generating enzyme" includes glucoamylase (a glucose generator), beta-amylase and maltogenic amylase (both maltose generators) and also alpha-glucosidase, isoamylase and pullulanase. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrate may be converted directly or indirectly to the desired fermentation product, preferably ethanol. A mixture of carbohydrate-source generating enzymes may be used. Blends include mixtures comprising at least a glucoamylase and an alpha-amylase, especially an acid amylase, even more preferred an acid fungal alpha-amylase.

In a conventional starch-to-ethanol process (i.e., including a liquefaction step), the ratio may preferably be as defined in EP 140410, especially when saccharification and fermentation are carried out simultaneously.

Glucoamylases

The term "glucoamylase" (1,4-alpha-D-glucan glucohydrolase, EC 3.2.1.3) is an enzyme, which catalyzes the release of D-glucose from the non-reducing ends of starch or related oligo- and polysaccharide molecules. Preferably the glucoamylase is the variant glucoamylase of the invention.

The glucoamylase may added in an amount of 0.001 to 10 AGU/g DS, preferably from 0.01 to 5 AGU/g DS, such as around 0.1, 0.3, 0.5, 1 or 2 AGU/g DS, especially 0.1 to 0.5 AGU/g DS or 0.02-20 AGU/g DS, preferably 0.1-10 AGU/g DS.

However, in one embodiment other glucoamylases may also be added. Such other glucoamylases may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al., 1984, *EMBO J.* 3(5): 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (Hata et al., 1991, *Agric. Biol. Chem.* 55(4): 941-949), or variants or fragments thereof. Other *Aspergillus* glucoamylase variants include variants with enhanced thermal stability: G137A and G139A (Chen et al., 1996, *Prot. Eng.* 9: 499-505); D257E and D293E/Q (Chen et al., 1995, *Prot. Eng.* 8: 575-582); N182 (Chen et al., 1994, *Biochem. J.* 301: 275-281); disulphide bonds, A246C (Fierobe et al., 1996, *Biochemistry* 35: 8698-8704; and introduction of Pro residues in positions A435 and S436 (Li et al., 1997, *Prot. Eng.* 10: 1199-1204.

Other glucoamylases include *Athelia rolfsii* (previously denoted *Corticium rolfsii*) glucoamylase (see U.S. Pat. No. 4,727,026 and Nagasaka et al., 1998, *Appl. Microbiol. Biotechnol.* 50: 323-330), *Talaromyces* glucoamylases, in particular derived from *Talaromyces duponti*, *Talaromyces emersonii* (WO 99/28448), *Talaromyces leycettanus* (U.S. Pat. No. Re. 32,153), and *Talaromyces thermophilus* (U.S. Pat. No. 4,587,215).

In a specific embodiment the glucoamylase is from a strain of the genus *Penicillium*, especially a strain of *Penicillium oxalicum*, in particular the *Penicillium oxalicum* glucoamylasedisclosed as SEQ ID NO: 2 in WO 2011/127802. In a preferred embodiment the glucoamylase is a variant of the *Penicillium oxalicum* glucoamylase disclosed as SEQ ID NO: 2 in WO 2011/127802 having a K79V substitution using the mature polypeptide (amino acids 22-616 of SEQ ID NO: 2) for numbering, and described in WO 2013/036526. In a preferred embodiment the glucoamylase is a variant of the *Penicillium oxalicum* glucoamylase disclosed as amino acids 22-616 of SEQ ID NO: 2 in WO 2011/127802 having a K79V substitution and one or more of the following substitutions P2N, P4S, P11F, T65A, Q327F, especially P2N+P4S+P11F+T65A+Q327F as described in WO2013/053801.

In a specific embodiment the glucoamylase is from a strain of the genus *Pycnoporus*, especially a strain of *Pycnoporus sanguineus*, in particular the *Pycnoporus sanguineus* glucoamylase disclosed as SEQ ID NO: 2, 4, or 6 in WO 2011/066576. In a preferred embodiment the enzyme composition comprises the glucoamylase shown as amino acids 19-573 of SEQ ID NO: 6 in WO 2011/066576.

In a specific embodiment the glucoamylase is from a strain of the genus *Gloeophillum*, especially a strain of *Gloeophyllum trabeum*, in particular the *Gloeophyllum trabeum* glucoamylase disclosed as SEQ ID NO: 18 in WO 2011/068803. In an especially preferred embodiment the enzyme composition comprises the *Gloeophyllum trabeum* glucoamylase shown in amino acids 18-576 of SEQ ID NO: 18 in WO2011/068803, and having one or more of the following substitutions: S95P, A121P, especially S95P+A121P using the mature polypeptide (positions 18-576 of SEQ ID NO: 18) for numbering.

In a specific embodiment the glucoamylase is from a strain of the genus *Gloeophillum*, especially a strain of *Gloeophillum sepiarium*, in particular the mature *Gloeophillum sepiarium* glucoamylase disclosed as amino acids 18-573 of SEQ ID NO: 2 in WO2011/068803.

Bacterial glucoamylases include glucoamylases from *Clostridium*, in particular *C. thermoamylolyticum* (EP 135138) and *C. thermohydrosulfuricum* (WO 86/01831), *Trametes cingulata*, *Pachykytospora papyracea*, and *Leucopaxillus giganteus*, all disclosed in WO 2006/069289; or *Peniophora rufomarginata* disclosed in PCT/US2007/066618; or a mixture thereof. A hybrid glucoamylase may be used in the present invention. Examples of hybrid glucoamylases are disclosed in WO 2005/045018. Specific examples include the hybrid glucoamylase disclosed in Tables 1 and 4 of Example 1 (which hybrids are hereby incorporated by reference).

The glucoamylase may have a high degree of sequence identity to any of above mentioned glucoamylases, i.e., at least 70%, at least 75%, at least 80%, at least 85%, at least 90%, at least 95%, at least 96%, at least 97%, at least 98%, at least 99% or even 100% identity to the mature enzymes sequences mentioned above.

Commercially available glucoamylase compositions include AMG 200L; AMG 300L; SAN™ SUPER, SAN™ EXTRA L, SPIRIZYME™ PLUS, SPIRIZYME™ FUEL, SPIRIZYME™ B4U, SPIRIZYME ULTRA™ and AMG™ E (from Novozymes NS, Denmark); OPTIDEX™ 300, GC480™ and GC147™ (from DuPont Industrial Biosciences, USA); AMIGASE™ and AMIGASE™ PLUS (from DSM); G-ZYME™ G900, G-ZYME™ and G990 ZR (from DuPont Industrial Biosciences).

Glucoamylases may be added in an amount of 0.02-20 AGU/g DS, preferably 0.1-10 AGU/g DS, especially between 1-5 AGU/g DS, such as 0.1-2 AGU/g DS, such as 0.5 AGU/g DS or in an amount of 0.0001-20 AGU/g DS, preferably 0.001-10 AGU/g DS, especially between 0.01-5 AGU/g DS, such as 0.1-2 AGU/g DS.

Beta-Amylases

A beta-amylase (E.C 3.2.1.2) is the name traditionally given to exo-acting maltogenic amylases, which catalyze the hydrolysis of 1,4-alpha-glucosidic linkages in amylose, amylopectin and related glucose polymers. Maltose units are successively removed from the non-reducing chain ends in a step-wise manner until the molecule is degraded or, in the case of amylopectin, until a branch point is reached. The maltose released has the beta anomeric configuration, hence the name beta-amylase.

Beta-amylases have been isolated from various plants and microorganisms (Fogarty and Kelly, 1979, *Progress in Industrial Microbiology* 15: 112-115). These beta-amylases are characterized by having a temperature optimum in the range from 40° C. to 65° C. and a pH optimum in the range from 4.5 to 7. A commercially available beta-amylase from barley is NOVOZYM™ WBA from Novozymes NS, Denmark and SPEZYME™ BBA 1500 from DuPont Industrial Biosciences, USA.

Maltogenic Amylases

The amylase may also be a maltogenic alpha-amylase (glucan 1,4-alpha-maltohydrolase, EC 3.2.1.133), which catalyzes the hydrolysis of amylose and amylopectin to maltose in the alpha-configuration. A maltogenic amylase from *Bacillus stearothermophilus* strain NCIB 11837 is commercially available from Novozymes NS. Maltogenic alpha-amylases are described in U.S. Pat. Nos. 4,598,048, 4,604,355 and 6,162,628, which are hereby incorporated by reference.

The maltogenic amylase may be added in an amount of 0.05-5 mg total protein/gram DS or 0.05-5 MANU/g DS.

Phytases

Any phytase may be used in a process of the present invention. Phytases are enzymes that degrade phytates and/or phytic acid by specifically hydrolyzing the ester link between inositol and phosphorus. Phytase activity is credited with phosphorus and ion availability in many ingredients. In some embodiments, the phytase is capable of liberating at least one inorganic phosphate from an inositol hexaphosphate (e.g., phytic acid). Phytases can be grouped according to their preference for a specific position of the phosphate ester group on the phytate molecule at which hydrolysis is initiated (e.g., 3-phytase (EC 3.1.3.8) or 6-phytase (EC 3.1.3.26)). An example of phytase is myo-inositol-hexakiphosphate-3-phosphohydrolase.

Phytases can be obtained from microorganisms such as fungal and bacterial organisms. For example, the phytase may be obtained from filamentous fungi such as *Aspergillus* (e.g., *A. ficuum, A. fumigatus, A. niger,* and *A. terreus*), *Cladospirum, Mucor* (e.g., *Mucor piriformis*), *Myceliophthora* (e.g., *M. thermophila*), *Penicillium* (e.g., *P. hordei* (ATCC No. 22053)), *P. piceum* (ATCC No. 10519), or *P. brevi-compactum* (ATCC No. 48944), *Talaromyces* (e.g., *T. thermophilus*), *Thermomyces* (WO 99/49740), and *Trichoderma* spp. (e.g., *T. reesei*).

In an embodiment, the phytate-degrading enzyme is obtained from yeast (e.g., *Arxula adeninivorans, Pichia anomala, Schwanniomyces occidentalis*), gram-negative bacteria (e.g., *Escherichia coli, Klebsiella* spp., *Pseudomonas* spp.), and gram-positive bacteria (e.g., *Bacillus* spp. such as *Bacillus subtilis*).

The phytase also may be obtained from *Citrobacter, Enterbacter,* or *Peniophora*.

In an embodiment, the phytase is derived from *Buttiauxiella* spp. such as *B. agrestis, B. brennerae, B. ferragutiase, B. gaviniae, B. izardii, B. noackiae,* and *B. warmboldiae.* In some embodiments, the phytase is a phytase disclosed in WO 2006/043178 or U.S. application Ser. No. 11/714,487.

In one preferred embodiment, the phytase has at least 75%, at least 80%, at least 85%, at least 88%, at least 90%, at least 93%, at least 95%, at least 96%, at least 97%, at least 98% and at least 99% sequence identity to the amino acid sequence set forth in SEQ ID NO: 31 of U.S. application Ser. No. 12/263,886.

Commercially-available phytases are NATUPHOS (BASF), RONOZYME P (Novozymes NS), PHYZYME (Danisco NS, Verenium) and FINASE (AB Enzymes). The method for determining microbial phytase activity and the definition of a phytase unit is disclosed in Engelen et al., 1994, *Journal of AOAC International* 77: 760-764. The phytase may be a wild-type phytase, an active variant or active fragment thereof.

Pullulanases

Pullulanases (E.C. 3.2.1.41, pullulan 6-glucano-hydrolase), are debranching enzymes characterized by their ability to hydrolyze the alpha-1,6-glycosidic bonds in, for example, amylopectin and pullulan.

The pullulanase may be a bacterial pullulanase, preferably derived from a strain of the genus *Bacillus*, especially derived from a strain of *Bacillus deramificans, Bacillus subtilis, Bacillus amyloderamificans,* or *Bacillus acidopullulyticus*.

Specifically contemplated pullulanases useful according to the present invention include the pullulanases the *Bacillus deramificans* disclosed as SEQ ID NO: 4 in WO 01/151620 (hereby incorporated by reference), as well as the pullulanases from *Bacillus deramificans* disclosed as Sequences 2, 4, and 6 of WO 2008/024372 (hereby incorporated by reference).

Specifically contemplated pullulanases useful according to the present invention include the pullulanases from *Bacillus amyloderamificans* disclosed in U.S. Pat. No. 4,560,651 (hereby incorporated by reference), the pullulanase disclosed as SEQ ID NO: 2 in WO 01/151620 (hereby incorporated by reference), and the pullulanase from *Bacillus acidopullulyticus* disclosed as SEQ ID NO: 6 in WO 01/151620 (hereby incorporated by reference) and also described in FEMS Mic. Let. (1994) 115, 97-106.

Other specifically contemplated pullulanases are those disclosed in WO2015/110473, in particular the variant pullulanase disclosed as SEQ ID NO: 21 in WO2015/110473 (included herein as SEQ ID NO: 5), wherein the substitutions 368G+393A+492S,A are maintained. Thus in this embodiment the pullulanase is selected from SEQ ID NO: 5 or a pullulanase having at least 85%, at least 90%, at least 95%, at least 96%, at least 97%, at least 98%, or at least 99%, or 100% sequence identity to the polypeptide of SEQ ID NO: 5, and comprising the substitutions N368G+N393A+A492S,A, using SEQ ID NO: 5 for numbering.

The pullulanase may according to the invention be added in an effective amount which include the preferred range of from between 1-100 micro g per g DS, especially from 10-60 micro g per g DS. Pullulanase activity may be determined as NPUN. An Assay for determination of NPUN is described in the "Materials & Methods"-section below.

In a preferred embodiment, the pullulanase is used in an amount between 1-100 micro g enzyme protein per g DS, preferably between 10-60 micro g enzyme protein per g DS.

Suitable commercially available pullulanase products include PROMOZYME D, PROMOZYME™ D2 (Novozymes A/S, Denmark), OPTIMAX L-1000, OPTIMAX L-300 (DuPont Industrial Biosciences), and AMANO 8 (Amano, Japan).

Proteases

A protease may be added during saccharification, fermentation, simultaneous saccharification and fermentation. The protease may be any protease. In a preferred embodiment the protease is an acid protease of microbial origin, preferably of fungal or bacterial origin. An acid fungal protease is preferred, but also other proteases can be used.

Suitable proteases include microbial proteases, such as fungal and bacterial proteases. Preferred proteases are acidic proteases, i.e., proteases characterized by the ability to hydrolyze proteins under acidic conditions below pH 7.

In a preferred embodiment the protease is derived from a strain of the bacterium *Pyrococcus*, such as a strain of *Pyrococcus furiosus* (pfu protease). Particularly the protease is the one shown as SEQ ID NO: 1 in U.S. Pat. No. 6,358,726-B1. In another embodiment the protease is the one shown as SEQ ID NO: 13 in WO2012/088303.

The acid fungal protease may be derived from *Aspergillus, Candida, Coriolus, Endothia, Enthomophtra, Irpex, Mucor, Penicillium, Rhizopus, Sclerotium,* and *Torulopsis*. In particular, the protease may be derived from *Aspergillus aculeatus* (WO 95/02044), *Aspergillus awamori* (Hayashida et al., 1977, *Agric. Biol. Chem.* 42(5), 927-933), *Aspergillus niger* (see, e.g., Koaze et al., 1964, *Agr. Biol. Chem. Japan* 28: 216), *Aspergillus saitoi* (see, e.g., Yoshida, 1954, *J. Agr. Chem. Soc. Japan* 28: 66), or *Aspergillus oryzae*, such as the pepA protease; and acidic proteases from *Mucor miehei* or *Mucor pusillus*.

The protease may be a neutral or alkaline protease, such as a protease derived from a strain of *Bacillus*. A particular protease is derived from *Bacillus amyloliquefaciens* and has the sequence obtainable at the Swissprot Database, Accession no. P06832. The proteases may have at least 90% sequence identity to the amino acid sequence disclosed in the Swissprot Database, Accession no. P06832 such as at least 92%, at least 95%, at least 96%, at least 97%, at least 98%, or particularly at least 99% identity.

The protease may have at least 90% sequence identity to the amino acid sequence disclosed as SEQ ID NO: 1 in WO 2003/048353 such as at 92%, at least 95%, at least 96%, at least 97%, at least 98%, or particularly at least 99% identity.

The protease may be a papain-like protease selected from the group consisting of proteases within EC 3.4.22.* (cysteine protease), such as EC 3.4.22.2 (papain), EC 3.4.22.6 (chymopapain), EC 3.4.22.7 (asclepain), EC 3.4.22.14 (actinidain), EC 3.4.22.15 (cathepsin L), EC 3.4.22.25 (glycyl endopeptidase) and EC 3.4.22.30 (caricain).

In an embodiment, the protease is a protease preparation derived from a strain of *Aspergillus*, such as *Aspergillus oryzae*. In another embodiment the protease is derived from a strain of *Rhizomucor*, preferably *Rhizomucor miehei*. In another embodiment the protease is a protease preparation, preferably a mixture of a proteolytic preparation derived from a strain of *Aspergillus*, such as *Aspergillus oryzae*, and a protease derived from a strain of *Rhizomucor*, preferably *Rhizomucor miehei*.

Aspartic acid proteases are described in, for example, Handbook of Proteolytic Enzymes, Edited by A. J. Barrett, N. D. Rawlings and J. F. Woessner, Academic Press, San Diego, 1998, Chapter 270. Examples of aspartic acid proteases include, e.g., those disclosed in Berka et al., 1990, *Gene* 96: 313; Berka et al., 1993, *Gene* 125: 195-198; and Gomi et al., 1993, *Biosci. Biotech. Biochem.* 57: 1095-1100, which are hereby incorporated by reference.

The protease also may be a metalloprotease, which is defined as a protease selected from the group consisting of:
(a) proteases belonging to EC 3.4.24 (metalloendopeptidases); preferably EC 3.4.24.39 (acid metallo proteinases);
(b) metalloproteases belonging to the M group of the above Handbook;
(c) metalloproteases not yet assigned to clans (designation: Clan MX), or belonging to either one of clans MA, MB, MC, MD, ME, MF, MG, MH (as defined at pp. 989-991 of the above Handbook);
(d) other families of metalloproteases (as defined at pp. 1448-1452 of the above Handbook);
(e) metalloproteases with a HEXXH motif;
(f) metalloproteases with an HEFTH motif;
(g) metalloproteases belonging to either one of families M3, M26, M27, M32, M34, M35, M36, M41, M43, or M47 (as defined at pp. 1448-1452 of the above Handbook);
(h) metalloproteases belonging to the M28E family; and
(i) metalloproteases belonging to family M35 (as defined at pp. 1492-1495 of the above Handbook).

In other particular embodiments, metalloproteases are hydrolases in which the nucleophilic attack on a peptide bond is mediated by a water molecule, which is activated by a divalent metal cation. Examples of divalent cations are zinc, cobalt or manganese. The metal ion may be held in place by amino acid ligands. The number of ligands may be five, four, three, two, one or zero. In a particular embodiment the number is two or three, preferably three.

There are no limitations on the origin of the metalloprotease used in a process of the invention. In an embodiment the metalloprotease is classified as EC 3.4.24, preferably EC 3.4.24.39. In one embodiment, the metalloprotease is an acid-stable metalloprotease, e.g., a fungal acid-stable metalloprotease, such as a metalloprotease derived from a strain of the genus *Thermoascus*, preferably a strain of *Thermoascus aurantiacus*, especially *Thermoascus aurantiacus* CGMCC No. 0670 (classified as EC 3.4.24.39). In another embodiment, the metalloprotease is derived from a strain of the genus *Aspergillus*, preferably a strain of *Aspergillus oryzae*.

In one embodiment, the metalloprotease has a degree of sequence identity to amino acids −178 to 177, −159 to 177, or preferably amino acids 1 to 177 (the mature polypeptide) of SEQ ID NO: 1 of WO 2010/008841 (a *Thermoascus aurantiacus* metalloprotease) of at least 80%, at least 82%, at least 85%, at least 90%, at least 95%, or at least 97%; and which have metalloprotease activity. In particular embodiments, the metalloprotease consists of an amino acid sequence with a degree of identity to SEQ ID NO: 1 as mentioned above.

The *Thermoascus aurantiacus* metalloprotease is a preferred example of a metalloprotease suitable for use in a process of the invention. In an preferred embodiment the protease is a variant of the *Thermoascus aurantiacus* metallo protease disclosed as SEQ ID NO: 2 in WO 2003/048353 or amino acids 1-177 of SEQ ID NO: 2 in WO 2011/072191 with the following mutations:

D79L+S87P+A112P+D142L;
D79L+S87P+D142L; or
A27K+D79L+Y82F+S87G+D104P+A112P+A126V+D142L.

Another metalloprotease is derived from *Aspergillus oryzae* and comprises the sequence of SEQ ID NO: 11 disclosed in WO 2003/048353, or amino acids −23-353; −23-374; −23-397; 1-353; 1-374; 1-397; 177-353; 177-374; or 177-397 thereof, and SEQ ID NO: 10 disclosed in WO 2003/048353.

Another metalloprotease suitable for use in a process of the invention is the *Aspergillus oryzae* metalloprotease comprising SEQ ID NO: 5 of WO 2010/008841, or a metalloprotease is an isolated polypeptide which has a degree of identity to SEQ ID NO: 5 of at least about 80%, at least 82%, at least 85%, at least 90%, at least 95%, or at least 97%; and which have metalloprotease activity. In particular embodiments, the metalloprotease consists of the amino acid sequence of SEQ ID NO: 5.

In a particular embodiment, a metalloprotease has an amino acid sequence that differs by forty, thirty-five, thirty, twenty-five, twenty, or by fifteen amino acids from amino acids −178 to 177, −159 to 177, or +1 to 177 of the amino acid sequences of the *Thermoascus aurantiacus* or *Aspergillus oryzae* metalloprotease.

In another embodiment, a metalloprotease has an amino acid sequence that differs by ten, or by nine, or by eight, or by seven, or by six, or by five amino acids from amino acids −178 to 177, −159 to 177, or +1 to 177 of the amino acid sequences of these metalloproteases, e.g., by four, by three, by two, or by one amino acid.

In particular embodiments, the metalloprotease a) comprises or b) consists of
  i) the amino acid sequence of amino acids −178 to 177, −159 to 177, or +1 to 177 of SEQ ID NO:1 of WO 2010/008841;
  ii) the amino acid sequence of amino acids −23-353, −23-374, −23-397, 1-353, 1-374, 1-397, 177-353, 177-374, or 177-397 of SEQ ID NO: 3 of WO 2010/008841;
  iii) the amino acid sequence of SEQ ID NO: 5 of WO 2010/008841; or
  allelic variants, or fragments, of the sequences of i), ii), and iii) that have protease activity.

A fragment of amino acids −178 to 177, −159 to 177, or +1 to 177 of SEQ ID NO: 1 of WO 2010/008841 or of amino acids −23-353, −23-374, −23-397, 1-353, 1-374, 1-397, 177-353, 177-374, or 177-397 of SEQ ID NO: 3 of WO 2010/008841; is a polypeptide having one or more amino acids deleted from the amino and/or carboxyl terminus of these amino acid sequences.

In one embodiment a fragment contains at least 75 amino acid residues, or at least 100 amino acid residues, or at least 125 amino acid residues, or at least 150 amino acid residues, or at least 160 amino acid residues, or at least 165 amino acid residues, or at least 170 amino acid residues, or at least 175 amino acid residues.

Commercially available products include ALCALASE®, ESPERASE™ FLAVOURZYME™, NEUTRASE®, NOVOZYM™ FM 2.0 L, and iZyme BA (available from Novozymes NS, Denmark) and GC106™ and SPEZYME™ FAN from DuPont Industrial Biosciences, USA, and RENNILASE® from DSM.

The invention is further defined in the following numbered paragraphs:

Paragraph 1. A glucoamylase variant comprising a substitution at a position corresponding to position 295 of the polypeptide of SEQ ID NO: 2, wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2.

Paragraph 2. The variant of paragraph 1, further comprises a substitution at least at one or more position corresponding to position 32, 83, 163, 169, 219, 224, 303 or 410 of the polypeptide of SEQ ID NO: 2, wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2.

Paragraph 3. The variant of any of paragraphs 1-2, wherein the number of substitutions is 1-20, e.g., 1-10 and 1-5, such as 1, 2, 3, 4, 5, 6, 7, 8, 9 or 10 substitutions.

Paragraph 4. The variant of any of the preceding paragraphs, wherein the variant comprises at least one or more of the substitutions selected from 295F, 295W, 224A, 224I, 224T, 32V, 83D, 163A, 163W, 169I, 219R, 303N or 410K.

Paragraph 5. The variant of any of the preceding paragraphs, wherein the variant comprises at least one of the following substitutions or combinations of substitutions:
295W;
295W+410K;
224I+295F;
224T+295W+318V;
295F;
224A+295F;
295W+83D+410K;
163A+295W+410K;
163W+295W+410K;
303N+295W;
169I+295W; or
32V+219R+295W;
wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2.

Paragraph 6. The variant according to any of paragraphs 1-5, wherein the variant comprises at least one of the following substitutions or combinations of substitutions:
295W+410K; or
163A+295W+410K;
wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2.

Paragraph 7. The variant according to any of the preceding paragraphs, wherein the substitutions are selected from Y295F, Y295W, L224A, L224I, L224T, A32V, S83D, N163A, N163W, V169I, T219R, S303NR410K, and Q318V.

Paragraph 8. The variant of any of paragraphs 1-7, which has an improved property relative to the parent, wherein the improved property is reduced glucose inhibition.

Paragraph 9. A glucoamylase variant, comprising a substitution at one or more positions corresponding to positions 271, 410, 72, 77, 145, 219, 303, 224, 318 of the polypeptide of SEQ ID NO: 2, wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2.

Paragraph 10. The variant of paragraph 8, wherein the number of substitutions is 1-20, e.g., 1-10 and 1-5, such as 1, 2, 3, 4, 5, 6, 7, 8, 9 or 10 substitutions.

Paragraph 11. The variant of paragraph 9, wherein the variant comprises at least one or more of the substitutions selected from 72V, 77A, 145A, 219D, 271Q, 271N, 271A, 271S, 271V, 224Q, 303E, 318W, 318F, 410A, 410Q or 410H.

Paragraph 12. The variant according to paragraphs 9-11, wherein the variant comprises at least one of the following substitutions or combinations of substitutions:
72V+145A;
271Q;
224Q+271N+410A;
77A;
77A+271A;
271S+318W+410Q;
271V+318F+410H;
77A+219D;
77A+303E;
wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2.

Paragraph 13. The variant according to paragraphs 9-12, wherein the substitutions are selected from D72V, L77A, L145A, T219D, L224Q, T271Q, T271N, T271A, T271S, T271V, S303E, Q318W, Q318F, R410Q, R410H and R410A.

Paragraph 14. The variant according to paragraphs 9-13, which has an improved property relative to the parent, wherein the improved property is increased specific activity.

Paragraph 15. A glucoamylase variant, comprising a substitution at one or more positions corresponding to positions 271, or 295 or 271 and 295 of the polypeptide of SEQ ID NO: 2, wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2.

Paragraph 16. The variant of paragraph 15, wherein the number of substitutions is 1-20, e.g., 1-10 and 1-5, such as 1, 2, 3, 4, 5, 6, 7, 8, 9 or 10 substitutions.

Paragraph 17. The variant of paragraph 15-16, wherein the variant comprises at least one or more of the substitutions selected from 271Q, 271A, 271V, 295W, 60L, 73A, 77A, 77V, and 318Y.

Paragraph 18. The variant according to any of the paragraphs 15-17, wherein the variant comprises at least one of the following substitutions or combinations of substitutions:
F60L+S73A+T271Q;
271Q;
77V+271V+410A;
77A+271A;
271V+318Y;
295W;
271Q+295W; and
wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 2.

Paragraph 19. The variant according to any of the paragraphs 15-18, which has an improved property relative to the parent, wherein the improved property is increased ethanol yield when used in SSF.

Paragraph 20. The variants according to paragraphs 18-19, wherein the substitutions are selected from F60L, S73A, T271A, T271V, T271Q, L77A, L77V, R410A, Y295W, and Q318Y.

Paragraph 21. The variant according to any of the preceding paragraphs, wherein the amino acid at position 95 and 121 is a proline.

Paragraph 22. A composition comprising the polypeptide of any of paragraphs 1-21.

Paragraph 23. The composition according to paragraph 22, further comprising a pullulanase.

Paragraph 24. The composition according to paragraph 23, wherein the pullulanase is selected from SEQ ID NO: 5 or a pullulanase having at least 85%, at least 90%, at least 95%, at least 96%, at least 97%, at least 98%, or at least 99%, or 100% sequence identity to the polypeptide of SEQ ID NO: 5, and comprising the substitutions N368G+N393A+A492S, A, using SEQ ID NO: 5 for numbering.

Paragraph 25. The composition according to paragraph 22 or 23, further comprising an alpha-amylase, particularly a fungal alpha-amylase, more particularly an alpha-amylase derived from Rhizomucor pusillus or Aspergillus terreus, even more particularly an alpha-amylase selected from the alpha-amylase disclosed as SEQ ID NO: 4, preferably having one or more of the following substitutions: G128D, D143N, preferably G128D+D143N (using SEQ ID NO: 4 for numbering), and wherein the alpha-amylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 4

Paragraph 26. A use of a polypeptide of any of paragraphs 1-21 for production of syrup and/or a fermentation product.

Paragraph 27. A process of producing a fermentation product, particularly ethanol, from starch-containing material comprising the steps of: (a) liquefying starch-containing material in the presence of an alpha amylase; (b) saccharifying the liquefied material; and (c) fermenting with a fermenting organism; wherein step (b) is carried out using at least a variant glucoamylase of any of paragraphs 1-21.

Paragraph 28. The process according to paragraph 27, wherein step (b) and step (c) are carried out simultaneously.

Paragraph 29. A process of producing a syrup product from starch-containing material, comprising the step of: (a) liquefying starch-containing material in the presence of an alpha amylase; (b) saccharifying the liquefied material in the presence of a variant glucoamylase of any of paragraphs 1-21.

Paragraph 30. An isolated polynucleotide encoding the variant of any of paragraphs 1-21.

Paragraph 31. A nucleic acid construct comprising the polynucleotide of paragraph 30.

Paragraph 32. An expression vector comprising the polynucleotide of paragraph 30.

Paragraph 33. A host cell comprising the polynucleotide of paragraph 30.

Paragraph 34. The host cell according to paragraph 33, wherein the host cell is a yeast cell, particularly a Saccharomyces sp., more particularly a Saccharomyces cerevisiae.

Paragraph 35. A method of producing a glucoamylase variant according to any of paragraphs 1-21, comprising: cultivating the host cell of paragraphs 33-34 under conditions suitable for expression of the variant; and optionally recovering the variant glucoamylase.

Paragraph 36. The process of paragraph 27-28, wherein the glucoamylase variant of any of claims 1-21 is expressed from the fermenting organism, preferably a yeast fermenting organism, more preferably a *Saccharomyces cerevisiae*.

The present invention is further described by the following examples that should not be construed as limiting the scope of the invention.

EXAMPLES

Materials and Methods

Glucoamylase enzymes from *Trametes* cingulate (Tc-AMG) disclosed in WO2006/069289, *Gloeophyllum sepiarum* (Gs-AMG) disclosed in WO2011/068803, *Pycnoporus sanguineus* (Ps-AMG) disclosed in WO2011/066576.

Pullulanase Assays

Pullulanase Activity (NPUN) Assay

Endo-pullulanase activity in NPUN is measured relative to a Novozymes pullulanase standard. One pullulanase unit (NPUN) is defined as the amount of enzyme that releases 1 micro mol glucose per minute under the standard conditions (0.7% red pullulan (Megazyme), pH 5, 40° C., 20 minutes). The activity is measured in NPUN/ml using red pullulan. 1 mL diluted sample or standard is incubated at 40° C. for 2 minutes. 0.5 mL 2% red pullulan, 0.5 M KCl, 50 mM citric acid, pH 5 are added and mixed. The tubes are incubated at 40° C. for 20 minutes and stopped by adding 2.5 ml 80% ethanol. The tubes are left standing at room temperature for 10-60 minutes followed by centrifugation 10 minutes at 4000 rpm. OD of the supernatants is then measured at 510 nm and the activity calculated using a standard curve.

Glucoamylase Activity

Glucoamylase activity may be measured in AGU Units.

Glucoamylase Activity (AGU)

The Glucoamylase Unit (AGU) is defined as the amount of enzyme, which hydrolyses 1 micromole maltose per minute under the standard conditions (37° C., pH 4.3, substrate: maltose 100 mM, buffer: acetate 0.1 M, reaction time 6 minutes as set out in the glucoamylase incubation below), thereby generating glucose.

| glucoamylase incubation: | |
|---|---|
| Substrate: | maltose 100 mM |
| Buffer: | acetate 0.1M |
| pH: | 4.30 ± 0.05 |
| Incubation temperature: | 37° C. ± 1 |
| Reaction time: | 6 minutes |
| Enzyme working range: | 0.5-4.0 AGU/mL |

The analysis principle is described by 3 reaction steps:

Step 1 is an enzyme reaction:

Glucoamylase (AMG), EC 3.2.1.3 (exo-alpha-1,4-glucan-glucohydrolase), hydrolyzes maltose to form alpha-D-glucose. After incubation, the reaction is stopped with NaOH. Steps 2 and 3 result in an endpoint reaction:

Glucose is phosphorylated by ATP, in a reaction catalyzed by hexokinase. The glucose-6-phosphate formed is oxidized to 6-phosphogluconate by glucose-6-phosphate dehydrogenase. In this same reaction, an equimolar amount of NAD+ is reduced to NADH with a resulting increase in absorbance at 340 nm. An autoanalyzer system such as Konelab 30 Analyzer (Thermo Fisher Scientific) may be used.

| Color reaction | |
|---|---|
| Tris | approx. 35 mM |
| ATP | 0.7 mM |
| NAD+ | 0.7 mM |
| Mg$^{2+}$ | 1.8 mM |
| Hexokinase | >850 U/L |
| Glucose-6-P-DH | >850 U/L |
| pH | approx. 7.8 |
| Temperature | 37.0° C. ± 1.0° C. |
| Reaction time | 420 sec |
| Wavelength | 340 nm |

Glucoamylase Activity Assay (Kikkoman)
Product code: 60211
Assay principle:

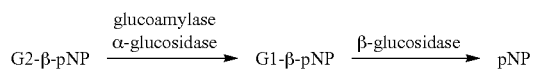

The substrate, 4-nitrophenyl-β-maltoside (G2-β-pNP) is degraded by glucoamylase or α-glucosidase into 4-nitrophenyl-β-glucoside (G1-β-pNP). G1-β-pNP is further degraded into 4-nitrophenol (pNP) by β-glucosidase in this kit. Reaction is performed at room temperature at pH about 4. The reaction is stopped by addition of sodium carbonate, and at the same time the solution becomes alkaline pH to maximize the absorbance of pNP. The glucose-forming activity is measured by quantifying the pNP at 400 nm.

1) The measured response shows the G2-3-pNP degradation activity of glucoamylase and α-glucosidase in the sample. This is thought to be the glucose forming activity in the sample.
2) The test can be used for rice koji extract without dialysis.
3) This assay is not affected by α-amylase in the sample.

Kit Components

| Reagent | Main component | Amount |
|---|---|---|
| substrate solution | G2-β-pNP | 60 ml |
| enzyme solution | β-glucosidase | 60 ml |
| stop solution | sodium carbonate | 120 ml |

1) Mix "substrate solution" and "enzyme solution" of the kit at 1:1.
2) Pipette 10 μl of the purified glucoamylase variant sample having about 0.1 AGU/ml activity (or water as a blank) and transfer to a microtiter plate well. (duplicate)
3) Add 60 μl of the substrate-enzyme mixture to the well.
4) Incubate at 32° C. temperature for 20 min.
5) Add 120 μl of the stop solution to the well.
6) Read OD400 nm. # Net $OD_{400}=OD_{400}$(sample)–$OD_{400}$ (blank)

1. Blank: Usually, the blank absorbance is less than 0.200.
2. Specificity: The response is not affected by glucose (up to 100 g/l) or α-amylase (725U/ml).
3. Reproducibility: The CV of absorbance is less than 1% when the same sample is analyzed 10 times.
4. Linear range: The net $OD_{400}$ up to 1.6 should be proportional to the enzyme concentration.
5. Stability of color: The absorbance does not change for 2 h at 25° C.

Thermostability

Thermostability was determined as the residual activity after heat treatment at 65° C. for 1 hour by using 0.2 AGU/ml sample. Sixty microliter of the diluted samples was incubated at 65° C. for 1 hour in PCR plates. The AMG activity of the heat treated sample was measured by Kikkoman assay kit, and the residual activity was calculated as the following equation;

Thermostability=$Vht/Vdw$

Vht; delta A400 of the variant of heat treated sample from the substrate without glucose
Vdw; delta A400 of the Gt-AMG from substrate without glucose
Glucose inhibition (GI)
Glucose inhibition was determined as the ratio of glucoamylase (AMG) activities with and without glucose (30%). Kikkoman assay kit was used for glucoamylase activity determination. The results were determined as relative value compared to the parent glucoamylase of SEQ ID NO: 2. Higher value corresponds to less inhibition.
Ten micro liter of the 3 times diluted samples was added to 190 micro liter of substrate (substrate solution in the kit: enzyme solution in the kit: 40% glucose or DW=1:1:6), and the reaction mixture was incubated at 37° C. The reaction time depended on the substrates, 30 min for the substrate without glucose and 2 hr with glucose. Then 80 micro liter of reaction mixture was mixed with 160 micro liters of 3% $Na_2CO_3$ to stop the reaction, and A400 was measured. The glucose inhibition value was calculated as the following equation;

Glucose inhibition=$(Vg/Vdw)/(WTg/WTdw)/2*0.5*100$

Vg; delta A400 of the variant from substrate with glucose
Vdw; delta A400 of the variant from substrate without glucose
WTg; delta A400 of the Gt-AMG from substrate with glucose
Vdw; delta A400 of the Gt-AMG from substrate without glucose
Specific Glucoamylase Activity (SA)
The specific activity was determined by AGU assay determined with Konelab instrument as described above. Protein concentration was calculated by A280 and the theoretical extinction coefficient of 1 mg/ml which is theoretically calculated from the protein sequence.
The, specific activity was determined from AGU activity and protein concentration.
Isomaltose formation activity assay (IF)
Isomaltose forming activity per AGU of glucoamylase from 30% w/v glucose at pH 4.3, 37° C. within 24 h was measured as follows:
The glucoamylase samples were diluted to 0.4 AGU/ml with buffer containing 100 mM Na-acetate, 0.02% TritonX-100, pH 4.3. One hundred microliter of the sample was mixed with 100 μL of glucose solution containing 60% w/v glucose, 100 mM NaOAc, pH 4.3 in a 0.2 ml PCR tube. The sample was incubated at 37° C. for 24 h. After incubation, the 100 μL was taken and mixed with the 200 μL deionized water and 300 μL 1 mg/ml xylose solution as an internal standard, and then deionized by adding approximately 50 mg ion exchange matrix (Amberlite, OREGANO, USA). Then 250 μL of the solution was transferred to 1.5 ml microtube and mixed with 500 μL of acetonitrile, and then filtrated through 0.2 μm nylon membrane filter prior to HPLC analysis. The formed isomaltose was separated from other oligosaccharides by HPLC equipping a SZ5532 column (Shodex, Japan) with linear gradient elution (7 minutes; start with 70%:30% acetonitrile:water; end with 60%:40% acetonitrile:water) and quantified by a Corona CAD detector (Thermo, USA) as the relative peak area against the xylose internal standard. As the standard samples, isomaltose solutions (Hayashibara, Japan) of concentrations from 0.125 to 1 mg/ml were treated the same way. The relative isomaltose formation activity per AGU against JGA098 (SEQ ID NO: 2) was shown in tables 1 and 2.
DE11 activity assay (DE11)
Activity of glucoamylase toward maltodextrin DE11 at 30% DS at pH 4.3, 60° C. was measured as follows:
The glucoamylase samples were diluted to 0.3 AGU/ml with 0.02% TritonX-100 solution. Fifty microliter of diluted sample was mixed with 500 μL of 33% maltodextrin solution buffered by 50 mM Na-acetate, and incubated at 60° C. for 20 min. The reaction was stopped by adding 200 μL of 1M Tris-HCl, pH 9.0. After cooling down to the ambient temperature, 50 μL aliquot of the sample was diluted 5-fold by deionized water and the glucose produced within this period was quantified by GOD-POD method (Clinica Chimica Acta, 1972, Vol. 37, pp. 538-540), e.g. by using Glucose C2 test kit solution (Wako, Japan). The relative glucose forming activity per AGU against JGA098 (SEQ ID NO: 2) is shown in tables 1 and 2.
DNA Manipulations
All plasmids were constructed and propagated in *E. coli* DH5α cells. The restriction endonucleases for DNA manipulations are obtainable from New England Biolabs, Inc. and are used according to the instruction. In-fusion (Clontech) is used for the ligation of DNAs. Amplified plasmids are recovered with Qiagen Plasmid Kit. Polymerase Chain Reaction (PCR) is carried out with Prime star Max DNA polymerase (Takara). QIAquick Gel Extraction Kit (Qiagen) is used for purification of DNA fragments excised from agarose gels. All DNA manipulation was basically following by the manufacturer's instruction and Molecular cloning: a laboratory manual ($2^{nd}$ ed.) Cold Spring Harbor Laboratory, Cold Spring Harbor, N.Y. described in Sambrook, Fritsch E F, Maniatis T (1989).

Example 1: Construction of Variants According to the Invention

WO2011/068803 discloses glucoamylases isolated from the fungus *Gloeophyllum*. In particular from *Gloeophyllum sepiarium* (Gs-AMG) and *Gloeophyllum trabeum* (Gt-AMG). A variant glucoamylase, JGA098, having the substitutions S95P+A121P and disclosed herein as SEQ ID NO: 2 was used as the parent glucoamylase. Starting from JGA098 further substitutions were introduced by standard procedures in the art and the resulting variants shown in the below table were constructed.

| AMG | Substitution (from JGA098, S95P, A121P) |
|---|---|
| JGA240 | D72V + L145A |
| JGA245 | T271Q |
| JGA247 | L224Q + T271N + R410A |
| JGA251 | L77V + T271V + R410A |
| JGA252 | L77A |
| JGA255 | L77A + T271A |
| JGA280 | T271S + Q318W + R410Q |
| JGA281 | T271V + Q318F + R410H |
| JGA283 | T271V + Q318Y |
| JGA287 | Y295W |
| JGA288 | Y295W + R410K |
| JGA289 | L224I + Y295F |
| JGA290 | L224T + Y295W + Q318V |

-continued

| AMG | Substitution (from JGA098, S95P, A121P) |
|---|---|
| JGA291 | Y295F |
| JGA292 | L224A + Y295F |
| JGA296 | T271Q + Y295W |
| JGA310 | F60L + S73A + T271Q |
| JGA329 | Y295W + S83D + R410K |
| JGA334 | N163A + Y295W + R410K |
| JGA335 | N163W + Y295W + R410K |
| JGA337 | L77A + S303E |
| JGA339 | S303N + Y295W |
| JGA340 | V169I + Y295W |
| JGA341 | A32V + T219R + Y295W |
| JGA344 | L77A + T219D |

Example 2: Glucoamylase Variants According to the Invention Having Reduced Glucose Inhibition (GI)

The specific variants constructed and shown in Example 1, were expressed as described in WO2011/068803. After expression the purified samples were characterized according to thermostability (T), glucose inhibition (GI), isomaltose formation (IF), specific activity (SA) and activity toward DE11 (DE11) as described in the assay section above. The variants shown in Table 1 all displayed reduced glucose inhibition compared to the parent glucoamylase of SEQ ID NO: 2.

TABLE 1

| AMG | Mutation | T | GI | IF | SA (A280 base) | DE11 |
|---|---|---|---|---|---|---|
| SEQ ID NO: 2 | | 64 | 100 | 100 | 6.6 | 100 |
| JGA287 | Y295W | 47 | 110 | 91 | 6.2 | 112 |
| JGA288 | Y295W + R410K | 47 | 124 | 104 | 6.4 | 106 |
| JGA289 | L224I + Y295F | 53 | 119 | 108 | 6.1 | 107 |
| JGA290 | L224T + Y295W + Q318V | 33 | 102 | 68 | 6.1 | 119 |
| JGA291 | Y295F | n.d. | 109 | 94 | 6.7 | 106 |
| JGA292 | L224A + Y295F | n.d. | 106 | 99 | 6.4 | 128 |
| JGA329 | Y295W + S83D + R410K | n.d. | 120 | 110 | 5.9 | n.d. |
| JGA334 | N163A + Y295W + R410K | n.d. | 132 | 110 | 6.3 | n.d. |
| JGA335 | N163W + Y295W + R410K | n.d. | 131 | 112 | 5.8 | n.d. |
| JGA339 | S303N + Y295W | n.d. | 104 | 94 | 6.7 | n.d. |
| JGA340 | V169I + Y295W | n.d. | 108 | 90 | 6.4 | n.d. |
| JGA341 | A32V + T219R + Y295W | n.d. | 114 | 97 | 6.0 | n.d. |

Example 3: Glucoamylase Variants According to the Invention Having Increased Specific Activity (SA)

The specific variants constructed and shown in example 1, were expressed as described in WO2011/068803. After expression the purified samples were characterized according to thermostability (T), glucose inhibition (GI), isomaltose formation (IF), specific activity (SA) and activity toward DE11 (DE11) as described in the assay section above. The variants shown in Table 2 all displayed increased specific activity compared to the parent glucoamylase of SEQ ID NO: 2.

TABLE 2

| AMG | Mutation | T | GI | IF | SA (A280 base) | DE11 |
|---|---|---|---|---|---|---|
| SEQ ID NO: 2 | | 64 | 100 | 100 | 6.6 | 100 |
| JGA240 | D72V + L145A | 45 | 79 | 93 | 7.3 | 87 |
| JGA245 | T271Q | 60 | 103 | 109 | 7.5 | 101 |
| JGA247 | L224Q + T271N + R410A | 56 | 89 | 90 | 7.4 | 105 |
| JGA252 | L77A | 60 | 102 | 64 | 7.6 | 86 |
| JGA255 | L77A + T271A | 42 | 84 | 69 | 7.3 | 91 |
| JGA280 | T271S + Q318W + R410Q | 64 | 65 | 74 | 7.2 | 104 |
| JGA281 | T271V + Q318F + R410H | 68 | 56 | 67 | 7.2 | 96 |
| JGA344 | L77A + T219D | n.d. | 98 | 76 | 7.2 | n.d. |
| JGA337 | L77A + S303E | n.d. | 98 | 95 | 7.1 | n.d. |

Example 3: Application of Gt-AMG Variants in Conventional SSF Process for Ethanol Production All treatments were evaluated via 5 g small assay. Each treatment ran three replicate. Corn mash liquefied using an experimental enzyme composition comprising an alpha-amylase, a glucoamylase and a protease, was used for the testing, wherein the alpha amylase may be selected from the group of Bacillus stearomthermphilus alpha-amylase variants:
I181*+G182*+N193F+E129V+K177L+R179E; or
I181*+G182*+N193F+V59A+Q89R+E129V+K177L+R179E+H208Y+K220P+N224L+Q254S; or
I181*+G182*+N193F+V59A+Q89R+E129V+K177L+R179E+Q254S+M284V; or
I181*+G182*+N193F+E129V+K177L+R179E+K220P+N224L+S242Q+Q254S (using SEQ ID NO: 3 disclosed in WO 99/19467 for numbering);
the protease may be selected from the protease disclosed in SEQ ID NO: 13 in WO2012/088303, or a protease variant of the Thermoascus aurantiacus metallo protease disclosed in WO 2011/072191 with the following mutations:
D79L+S87P+A112P+D142L;
D79L+S87P+D142L; or
A27K+D79L+Y82F+S87G+D104P+A112P+A126V+D142L;
and the glucoamylase is selected from a variant of the Penicillium oxalicum described in WO 2013/036526.

3 ppm penicillin and 1000 ppm urea were supplemented into the mash. The pH of this slurry was adjusted to 5.0 with 40% $H_2SO_4$, and total solids of the mash were measured as 28.4%. Approximately 5 g of this slurry was added to 15 ml polypropylene tube. The tubes were prepared by drilling a 1/32 inch hole and the empty tubes were then weighed before corn slurry was added. The tubes were weighed again after mash was added to determine the exact weight of mash in each tube. Each tube was dosed with actual enzyme dosage based on the exact weight of corn slurry in each tube. The enzyme dosage for each treatment was listed in Table 3, and Gt-AMG variants of the invention tested in this study were listed in Table 4, and wild type Ps-AMG (a glucoamylase from Pycnoporus sanguineus disclosed in WO2011/066576 as SEQ ID NO: 4), Gs-AMG (a glucoamylase from Gloeophyllum sepiarium disclosed in WO2011/068803 as SEQ ID NO: 2) and Tc-AMG (a glucoamylase from Trametes cingulata disclosed in WO2006/069289 as SEQ ID NO: 2) were used as the controls. Afterwards, the tubes were dosed with 100 μl of yeast propagate to around 5 g corn mash, and then were incubated in 32° C. humidified air shaker for SSF (simultaneous saccharification and fermentation). Samples were taken at 53 hour of fermentation for HPLC analysis. The HPLC preparation consisted of stopping the reaction by addition of 50 micro liters of 40% $H_2SO_4$, centrifuging, and filtering through a 0.45 micrometer filter. Samples were stored at 4° C. until analysis. Agilent™ 1100 HPLC system coupled with RI detector was used to determine ethanol and oligosaccharides concentration. The separation column was aminex HPX-87H ion exclusion column (300 mm×7.8 mm) from BioRad™

TABLE 3

Enzyme dosage for each treatment

| | Treatment | AMG, µg EP/gDS |
|---|---|---|
| 1 | AMG, 40 µg/g | 40 |
| 2 | AMG, 55 µg/g | 55 |
| 3 | AMG, 70 µg/g | 70 |

TABLE 4

List of Gt-AMG variants tested in conventional SSF. JGA098 represents the parent glucoamylase used in this study. It is disclosed herein as SEQ ID NO: 2.

| | Enzyme |
|---|---|
| 1 | JGA098 |
| 2 | JGA245 |
| 3 | JGA251 |
| 4 | JGA255 |
| 5 | JGA283 |
| 6 | JGA287 |
| 7 | JGA296 |
| 8 | JGA310 |

Results:

The results from HPLC analysis were summarized in the FIGURE. The enzyme dose in X-axis was AGU/gDS, (DS=dry solids), which was converted from enzyme protein dosage of µg/gDS in Table 3 and specific activity of each AMG (glucoamylase). Results showed that Gt-AMG variants JGA245, JGA251, JGA255, JGA283, JGA287, JGA296, and JGA310 all outperformed the wild type AMGs in the study.

Example 4: Saccharification Test of JGA287

Maltodextrin powder from corn starch liquefaction was dissolved in water while heating to make slurry starch slurry at 35.6% dry solids. The solid content of the slurry was measured using Refractive index measurement showing 1.39503. The slurry was adjusted to a pH of 4.3 using a 1M Hydrochloric acid solution. 18 gram aliquots of this slurry were added to glass reaction scintillation vials with septum cap closures and were inserted in a heating block to be heated to a temperature of 61° C. Each vial was given an enzyme dosage based on the table below and additional water was added to each vial to reach a target dry solid of 33%. Saccharification was performed using a glucoamylase and a pullulanase. The pullulanase, Promozyme D2 (available from Novozymes NS), is derived from *Bacillus deramificans* and is disclosed herein as SEQ ID NO: 3. 1.5 mL samples were taken via needles through the septum from each vial at different time points and were deactivated at 105° C. for 5 minutes. 1 mL of each deactivated sample was diluted with 4 mL deionized water. The diluted samples were evaluated using a HPLC method DP1-4 for measuring dextrose purity (% DP1 or % DX) and % DP2.

Table 5 show % DX and % DP2 of syrups treated with two different AMGs after 72 hours of saccharification. Average and standard deviation was used from three treatments. The results show that at doses tested both JGA98 and JGA287 show similar % DX values that are not statistically significantly different. However, % DP2 results show statistically significantly 0.09% lower DP2 generated when JGA287 was used.

TABLE 5

| | Enzyme activities | | % DX after 72 hrs | | % DP2 after 72 hrs | |
|---|---|---|---|---|---|---|
| Treatments | AGU/gDS | NPUN/gDS | Average | Standard deviation | Average | Standard deviation |
| JGA98 (0.15 AGU) + Promozyme D2 | 0.15 | 0.96 | 95.88 | 0.21 | 2.10 | 0.04 |
| JGA98 (0.18 AGU) + Promozyme D2 | 0.18 | 0.96 | 96.19 | 0.14 | 2.28 | 0.06 |
| JGA98 (0.22 AGU) + Promozyme D2 | 0.22 | 0.96 | 96.15 | 0.06 | 2.46 | 0.01 |
| JGA98 (0.25 AGU) + Promozyme D2 | 0.25 | 0.96 | 96.09 | 0.05 | 2.66 | 0.01 |
| JGA287 (0.15 AGU) + Promozyme D2 | 0.15 | 0.96 | 95.85 | 0.31 | .03 | 0.02 |
| JGA287 (0.18 AGU) + Promozyme D2 | 0.18 | 0.96 | 96.00 | 0.25 | 2.19 | 0.09 |
| JGA287 (0.22 AGU) + Promozyme D2 | 0.22 | 0.96 | 96.14 | 0.24 | 2.36 | 0.09 |
| JGA287 (0.25 AGU) + Promozyme D2 | 0.25 | 0.96 | 96.08 | 0.17 | 2.54 | 0.05 |

Example 5: Saccharification Test of JGA252

Maltodextrin powder from corn starch liquefaction was dissolved in water while heating to make slurry starch slurry at 36.5% dry solids. The solid content of the slurry was measured using Refractive index measurement showing 1.39690. The slurry was adjusted to a pH of 4.3 using a 1M Hydrochloric acid solution. 18 gram aliquots of this slurry were added to glass reaction scintillation vials with septum cap closures and were inserted in a heating block to be heated to a temperature of 61° C. Each vial was given an enzyme dosage based on the table below and additional water was added to each vial to reach a target dry solid of 33%. 1.5 mL samples were taken via needles through the septum from each vial at different time points and were deactivated at 105° C. for 5 minutes. 1 mL of each deactivated sample was diluted with 4 mL deionized water. The diluted samples were evaluated using a HPLC method DP1-4 for measuring dextrose purity (% DP1 or % DX) and % DP2.

Table 6 shows % DX and % DP2 of syrups treated with two different AMGs after 72 hours of saccharification. Average and standard deviation was used from three treatments. The results show that at doses tested both JGA252 shows statistically significantly higher % DX values than JGA98. % DP2 results show statistically significantly lower DP2 generated when JGA252 was used.

at 39.7% dry solids. The solid content of the slurry was measured using Refractive index measurement showing 1.4035. The slurry was adjusted to a pH of 4.3 using a 1M Hydrochloric acid solution. 18 gram aliquots of this slurry were added to glass reaction scintillation vials with septum cap closures and were inserted in a heating block to be heated to a temperature of 61° C. Each vial was given an enzyme dosage based on the table below and additional water was added to each vial to reach a target dry solid of 33%. 1.5 mL samples were taken via needles through the septum from each vial at different time points and were deactivated at 105° C. for 5 minutes. 1 mL of each deactivated sample was diluted with 4 mL deionized water. The diluted samples were evaluated using a HPLC method DP1-4 for measuring dextrose purity (% DP1 or % DX).

Table 7 show % DX of syrups treated with two different AMGs during saccharification. Average obtained from three treatments. The results show that JGA288 shows faster reaction time than JGA98, therefore reaching the dextrose purity target for saccharification in shorter time.

TABLE 6

| Treatments | Enzyme activities | | % DX after 72 hrs | | % DP2 after 72 hrs | |
|---|---|---|---|---|---|---|
| | AGU/gDS | NPUN/gDS | average | Standard deviation | average | Standard deviation |
| JGA98 (0.15 AGU) + Promozyme D2 | 0.15 | 0.96 | 96.31 | 0.17 | 1.94 | 0.02 |
| JGA98 (0.18 AGU) + Promozyme D2 | 0.18 | 0.96 | 96.47 | 0.04 | 2.12 | 0.05 |
| JGA98 (0.22 AGU) + Promozyme D2 | 0.22 | 0.96 | 96.40 | 0.05 | 2.35 | 0.03 |
| JGA98 (0.25 AGU) + Promozyme D2 | 0.25 | 0.96 | 96.24 | 0.08 | 2.56 | 0.06 |
| JGA252 (0.15 AGU) + Promozyme D2 | 0.15 | 0.96 | 96.50 | 0.08 | 1.85 | 0.02 |
| JGA252 (0.18 AGU) + Promozyme D2 | 0.18 | 0.96 | 96.58 | 0.03 | 1.96 | 0.04 |
| JGA252 (0.22 AGU) + Promozyme D2 | 0.22 | 0.96 | 96.58 | 0.09 | 2.14 | 0.09 |
| JGA252 (0.25 AGU) + Promozyme D2 | 0.25 | 0.96 | 96.50 | 0.07 | 2.26 | 0.06 |

Example 6: Saccharification Test of JGA288

Maltodextrin powder from corn starch liquefaction was dissolved in water while heating to make slurry starch slurry

TABLE 7

| Treatments | Enzyme activities | | % DX (average of three treatments) | | | | |
|---|---|---|---|---|---|---|---|
| | AGU/gDS | NPUN/gDS | 24 hours | 36 hours | 42 hours | 48 hours | 60 hours |
| JGA98 (0.18 AGU) + Promozyme D2 | 0.18 | 0.96 | 87.53 | 92.56 | 93.97 | 94.96 | 95.93 |
| JGA98 (0.2 AGU) + Promozyme D2 | 0.2 | 0.96 | 88.41 | 93.16 | 94.38 | 95.29 | 95.96 |
| JGA98 (0.22 AGU) + Promozyme D2 | 0.22 | 0.96 | 89.72 | 93.99 | 95.03 | 95.67 | 96.12 |
| JGA98 (0.25 AGU) + Promozyme D2 | 0.25 | 0.96 | 90.41 | 94.31 | 95.18 | 95.86 | 96.17 |
| JGA288 (0.18 AGU) + Promozyme D2 | 0.18 | 0.96 | 88.57 | 93.48 | 94.66 | 95.56 | 96.17 |
| JGA288 (0.2 AGU) + Promozyme D2 | 0.2 | 0.96 | 90.01 | 94.14 | 95.21 | 95.99 | 96.29 |
| JGA288 (0.22 AGU) + Promozyme D2 | 0.22 | 0.96 | 90.41 | 94.53 | 95.42 | 96.12 | 96.26 |
| JGA288 (0.25 AGU) + Promozyme D2 | 0.25 | 0.96 | 91.37 | 94.93 | 95.68 | 96.11 | 96.26 |

Example 7: Saccharification Test of JGA334

Maltodextrin powder from corn starch liquefaction was dissolved in water while heating to make slurry starch slurry at 36.5% dry solids. The solid content of the slurry was measured using Refractive index measurement showing 1.39999. The slurry was adjusted to a pH of 4.3 using a 1M Hydrochloric acid solution. 50 gram aliquots of this slurry were added to glass reaction vials with septum cap closures and were inserted in a water bath to be heated to a temperature of 61° C. Each vial was given an enzyme dosage based on the table below and additional water was added to each vial to reach a target dry solid of 33%. 1.5 mL samples were taken via needles through the septum from each vial at different time points and were deactivated at 105° C. for 10 minutes. 1 mL of each deactivated sample was diluted with 4 mL deionized water. The diluted samples were evaluated using a HPLC method DP1-4 for measuring dextrose purity (% DP1 or % DX).

Table 8 show % DX of syrups treated with two different AMGs (glucoamylases) after 60 hours of saccharification. Average and standard deviation was used from two replicates. The results show that JGA334 shows faster reaction time than JGA98 therefore reaching dextrose purity target for saccharification at shorter time. Also at doses tested JGA334 shows higher % DX values that are statistically different than JGA98.

TABLE 8

| | Enzyme activities | | % DX after 60 hrs | |
|---|---|---|---|---|
| Treatments | AGU/gDS | NPUN/gDS | average | Standard deviation |
| JGA98 (0.28 AGU) + Promozyme D2 | 0.28 | 0.96 | 95.9 | 0.14 |
| JGA98 (0.25 AGU) + Promozyme D2 | 0.25 | 0.96 | 95.9 | 0.05 |
| JGA98 (0.18 AGU) + Promozyme D2 | 0.18 | 0.96 | 95.8 | 0.02 |
| JGA334 (0.28 AGU) + Promozyme D2 | 0.28 | 0.96 | 96.3 | 0.02 |
| JGA334 (0.25 AGU) + Promozyme D2 | 0.25 | 0.96 | 96.3 | 0.05 |
| JGA334 (0.18 AGU) + Promozyme D2 | 0.18 | 0.96 | 96.4 | 0.17 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A glucoamylase variant having glucoamylase activity and comprising an amino acid sequence that has at least 90%, but less than 100%, sequence identity to the amino acid sequence of SEQ ID NO: 2 and wherein the amino acid at the position corresponding to amino acid 295 of SEQ ID NO: 2 is substituted with a different amino acid in the amino acid sequence of the glucoamylase variant.

2. The glucoamylase variant of claim 1, wherein the glucoamylase variant further comprises an amino acid substitution at one or more positions corresponding to position 32, 83, 163, 169, 219, 224, 303 or 410 of the amino acid sequence of SEQ ID NO: 2.

3. The glucoamylase variant of claim 1, wherein the glucoamylase variant comprises no more than 20 amino acid substitutions relative to the amino acid sequence of SEQ ID NO: 2.

4. The glucoamylase variant of claim 1, wherein the glucoamylase variant comprises at least one or more of the substitutions selected from 295F, 295W, 224A, 224I, 224T, 32V, 83D, 163A, 163W, 169I, 219R, 303N or 410K, wherein the amino acid numbering corresponds to positions of the amino acid sequence of SEQ ID NO: 2.

5. The glucoamylase variant of claim 1, wherein the glucoamylase variant comprises at least one of the following substitutions or combinations of substitutions:
   295W;
   295W+410K;
   224I+295F;
   224T+295W+318V;

295F;
224A+295F;
295W+83D+410K;
163A+295W+410K;
163W+295W+410K;
303N+295W;
169I+295W; or
32V+219R+295W,
wherein the amino acid numbering corresponds to positions of the amino acid sequence of SEQ ID NO: 2.

6. The glucoamylase variant of claim 1, wherein the glucoamylase variant comprises at least one of the following substitutions or combinations of substitutions:
295W+410K; or
163A+295W+410K,
wherein the amino acid numbering corresponds to positions of the amino acid sequence of SEQ ID NO: 2.

7. The glucoamylase variant of claim 1, wherein the substitution at the position corresponding to amino acid 295 of SEQ ID NO: 2 is Y295F or Y295W.

8. The glucoamylase variant of claim 1, wherein the glucoamylase variant has reduced glucose inhibition as compared to a glucoamylase comprising the amino acid sequence of SEQ ID NO: 2.

9. A glucoamylase variant having glucoamylase activity and comprising an amino acid sequence that has at least 90%, but less than 100%, sequence identity to the amino acid sequence of SEQ ID NO: 2 and wherein the amino acid at the position corresponding to amino acid 271 of SEQ ID NO: 2 and the amino acid at the position corresponding to amino acid 295 of SEQ ID NO: 2 are substituted with different amino acids in the amino acid sequence of the glucoamylase variant.

10. The glucoamylase variant of claim 9, wherein the glucoamylase variant comprises no more than 20 amino acid substitutions relative to the amino acid sequence of SEQ ID NO: 2.

11. The glucoamylase variant of claim 9, wherein the glucoamylase variant comprises at least one or more of the substitutions selected from 271Q, 271A, 271V, 295W, 60L, 73A, 77A, 77V, and 318Y, wherein the amino acid numbering corresponds to positions of the amino acid sequence of SEQ ID NO: 2.

12. The glucoamylase variant of claim 9, wherein the glucoamylase variant comprises at least one of the following substitutions or combinations of substitutions:
F60L+S73A+T271Q;
271Q;
77V+271V+410A;
77A+271A;
271V+318Y;
295W; or
271Q+295W,
wherein the amino acid numbering corresponds to positions of the amino acid sequence of SEQ ID NO: 2.

13. The glucoamylase variant of claim 9, wherein the glucoamylase variant has increased ethanol yield when used with an ethanol fermenting microorganism in a simultaneous saccharification and fermentation (SSF) as compared to a glucoamylase comprising the amino acid sequence of SEQ ID NO: 2.

14. The glucoamylase variant of claim 1, wherein the amino acid at each of positions 95 and 121 is a proline, wherein the amino acid numbering corresponds to positions of the amino acid sequence of SEQ ID NO: 2.

15. A composition comprising the glucoamylase variant of claim 1.

16. The composition of claim 15, further comprising a pullulanase.

17. The composition of claim 15, further comprising an alpha-amylase variant, wherein the alpha-amylase variant has alpha-amylase activity and comprises an amino acid sequence that has at least 90%, but less than 100%, sequence identity to the amino acid sequence of SEQ ID NO: 4 and wherein the alpha-amylase variant has one or more of the following substitutions: G128D, D143N, or G128D+D143N, wherein the amino acid numbering corresponds to positions of the amino acid sequence of SEQ ID NO: 4.

18. A process of producing a fermentation product, from starch-containing material comprising the steps of:
(a) liquefying starch-containing material in the presence of an alpha amylase;
(b) contacting the liquefied starch-containing material from step (a) with the glucoamylase variant of claim 1 to saacharify the liquefied starch-containing material; and
(c) fermenting the saccharified material from step (b) with a fermenting microorganism, thereby producing a fermentation product.

19. The process of claim 18, wherein step (b) and step (c) are carried out simultaneously.

20. A process of producing a syrup product from starch-containing material, comprising the steps of:
(a) liquefying starch-containing material in the presence of an alpha amylase; and
(b) contacting the liquefied starch-containing material from step (a) with the glucoamylase variant of claim 1 to saacharify the liquefied starch-containing material, thereby producing a syrup product.

21. An isolated polynucleotide encoding the glucoamylase variant of claim 1.

22. A nucleic acid construct comprising the polynucleotide of claim 21.

23. An expression vector comprising the polynucleotide of claim 21.

24. An isolated host cell comprising the polynucleotide of claim 21.

25. The host cell of claim 24, wherein the host cell is a yeast cell.

26. A method of producing a glucoamylase variant, comprising: cultivating the isolated host cell of claim 24 under conditions suitable for expression of the glucoamylase variant; and optionally recovering the glucoamylase variant.

27. The process of claim 18, wherein the glucoamylase variant is expressed from the fermenting microorganism.

* * * * *

SEQUENCE LISTING

<160> NUMBER OF SEQ ID NOS: 5

<210> SEQ ID NO 1
<211> LENGTH: 1731
<212> TYPE: DNA
<213> ORGANISM: Artificial
<220> FEATURE:
<223> OTHER INFORMATION: Variant glucoamylase

<400> SEQUENCE: 1

```
atgtaccgct tccttgtctg tgctctcggg cttctgggga cagtcctcgc tcagtcagtc    60
gacagttatg tcggcagcga aggccccata gcaaaggccg gcgtccttgc caacattggg   120
ccgaacggct caaaggcctc tggtgcagcc gccggcgtgg tggtggctag ccccagcaag   180
tcggatcccg actattggta cacttggacg cgtgactcgt cactcgtttt caagtctctc   240
attgatcagt acaccactgg tatcgacagc acgagttcgt tgaggtctct gatagacagt   300
ttcgttattg ccgaggccaa cattcagcag gtccccaatc ccagcggcac tcttactacc   360
ggcggcttgg gagagccaaa attcaatgtc gatgaaactg cattcaccgg tccgtggggt   420
cgaccccagc gcgacggacc tgcgctccgt gcgactgctt tgatcaccta cggtaactgg   480
ctcttgtcaa acgggaacac gacctgggtt accagtacgc tgtggccgat catccagaac   540
gatctcaact acgtcgttca gtactggaac cagaccacct tcgacctctg ggaagaagtg   600
aactcttcct cgttcttcac cactgcagtg cagcaccgtg ccttgcgcga aggcgcagca   660
ttcgctacca agatcggtca gacctcctcg gtcagcagct acacaaccca agcggcgaat   720
ctactttgct ttttgcagtc ttactggaac cccacttccg gatatatcac cgctaacact   780
ggcggtggtc ggtccggcaa ggacgccaac accctcttgg catccatcca cacttacgac   840
cccagcgcgg gctgcgatgc cacgaccttc cagccctgct ccgacaaagc cctctcgaat   900
```

```
ctgaaggttt acgtcgactc cttccgttct gtctactcca tcaacagcgg tattgcctct    960
aacgccgctg tcgccactgg tcgctacccg gaagacagct accagggcgg gaacccatgg   1020
tacctcacta cgttcgccgt cgccgagcag ctctatgacg ccctcaatgt ctgggctgct   1080
cagggctccc tcaatgtcac ctccatctcc ctcccttct tccagcagtt ctcctctagt    1140
gtcactgccg gcacttacgc ttcgagctcc accacttaca cgactctgac ctccgccatt   1200
aagagcttcg cggatggatt cgtcgctatc aacgcccagt acacgccgtc caacggtggc   1260
ctcgctgagc agttcagcag gagcaacggc gctcccgtca gcgctgttga tttgacatgg   1320
agctatgcat ctgcattgac cgcgtttgaa gcgaggaata atactcagtt cgccggctgg   1380
ggcgcggtag gtttgactgt gccgaccctc gtgctccagca acagtggtgg aggcggagga   1440
tcgactgtcg ccgtgacgtt caacgtgaac gcccaaacgg tttggggcga aaacatctac   1500
atcactggct cggttgacgc tctgagtaac tggtctcccg caacgccct cttgctctcg    1560 tctgccaact acccgacctg gagcattacc gtgaattac ccgcgagcac tgccattcag    1620
tataagtata tccgcaagaa caacggagct gtcacctggg aatccgatcc caacaacagc   1680
ataactactc cagccagcgg ctccgtgacc gagaatgaca cttggcgtta a             1731
```

<210> SEQ ID NO 2
<211> LENGTH: 559
<212> TYPE: PRT
<213> ORGANISM: Artificial
<220> FEATURE:
<223> OTHER INFORMATION: Variant glucoamylase

<400> SEQUENCE: 2

```
Gln Ser Val Asp Ser Tyr Val Gly Ser Glu Gly Pro Ile Ala Lys Ala
1               5                   10                  15

Gly Val Leu Ala Asn Ile Gly Pro Asn Gly Ser Lys Ala Ser Gly Ala
            20                  25                  30

Ala Ala Gly Val Val Val Ala Ser Pro Ser Lys Ser Asp Pro Asp Tyr
        35                  40                  45

Trp Tyr Thr Trp Thr Arg Asp Ser Ser Leu Val Phe Lys Ser Leu Ile
    50                  55                  60

Asp Gln Tyr Thr Thr Gly Ile Asp Ser Thr Ser Ser Leu Arg Ser Leu
65                  70                  75                  80

Ile Asp Ser Phe Val Ile Ala Glu Ala Asn Ile Gln Gln Val Pro Asn
                85                  90                  95

Pro Ser Gly Thr Leu Thr Thr Gly Gly Leu Gly Glu Pro Lys Phe Asn
            100                 105                 110

Val Asp Glu Thr Ala Phe Thr Gly Pro Trp Gly Arg Pro Gln Arg Asp
        115                 120                 125

Gly Pro Ala Leu Arg Ala Thr Ala Leu Ile Thr Tyr Gly Asn Trp Leu
    130                 135                 140

Leu Ser Asn Gly Asn Thr Thr Trp Val Thr Ser Thr Leu Trp Pro Ile
145                 150                 155                 160

Ile Gln Asn Asp Leu Asn Tyr Val Val Gln Tyr Trp Asn Gln Thr Thr
                165                 170                 175

Phe Asp Leu Trp Glu Glu Val Asn Ser Ser Phe Phe Thr Thr Ala
            180                 185                 190

Val Gln His Arg Ala Leu Arg Glu Gly Ala Ala Phe Ala Thr Lys Ile
        195                 200                 205

Gly Gln Thr Ser Ser Val Ser Ser Tyr Thr Thr Gln Ala Ala Asn Leu
    210                 215                 220
```

```
Leu Cys Phe Leu Gln Ser Tyr Trp Asn Pro Thr Ser Gly Tyr Ile Thr
225                 230                 235                 240

Ala Asn Thr Gly Gly Gly Arg Ser Gly Lys Asp Ala Asn Thr Leu Leu
                245                 250                 255

Ala Ser Ile His Thr Tyr Asp Pro Ser Ala Gly Cys Asp Ala Thr Thr
                260                 265                 270

Phe Gln Pro Cys Ser Asp Lys Ala Leu Ser Asn Leu Lys Val Tyr Val
                275                 280                 285

Asp Ser Phe Arg Ser Val Tyr Ser Ile Asn Ser Gly Ile Ala Ser Asn
            290                 295                 300

Ala Ala Val Ala Thr Gly Arg Tyr Pro Glu Asp Ser Tyr Gln Gly Gly
305                 310                 315                 320

Asn Pro Trp Tyr Leu Thr Thr Phe Ala Val Ala Glu Gln Leu Tyr Asp
                325                 330                 335

Ala Leu Asn Val Trp Ala Ala Gln Gly Ser Leu Asn Val Thr Ser Ile
                340                 345                 350

Ser Leu Pro Phe Phe Gln Gln Phe Ser Ser Val Thr Ala Gly Thr
                355                 360                 365

Tyr Ala Ser Ser Ser Thr Thr Tyr Thr Thr Leu Thr Ser Ala Ile Lys
370                 375                 380

Ser Phe Ala Asp Gly Phe Val Ala Ile Asn Ala Gln Tyr Thr Pro Ser
385                 390                 395                 400

Asn Gly Gly Leu Ala Glu Gln Phe Ser Arg Ser Asn Gly Ala Pro Val
                405                 410                 415

Ser Ala Val Asp Leu Thr Trp Ser Tyr Ala Ser Ala Leu Thr Ala Phe
                420                 425                 430

Glu Ala Arg Asn Asn Thr Gln Phe Ala Gly Trp Gly Ala Val Gly Leu
                435                 440                 445

Thr Val Pro Thr Ser Cys Ser Ser Asn Ser Gly Gly Gly Gly Ser
                450                 455                 460

Thr Val Ala Val Thr Phe Asn Val Asn Ala Gln Thr Val Trp Gly Glu
465                 470                 475                 480

Asn Ile Tyr Ile Thr Gly Ser Val Asp Ala Leu Ser Asn Trp Ser Pro
                485                 490                 495

Asp Asn Ala Leu Leu Leu Ser Ser Ala Asn Tyr Pro Thr Trp Ser Ile
                500                 505                 510

Thr Val Asn Leu Pro Ala Ser Thr Ala Ile Gln Tyr Lys Tyr Ile Arg
                515                 520                 525

Lys Asn Asn Gly Ala Val Thr Trp Glu Ser Asp Pro Asn Asn Ser Ile
                530                 535                 540

Thr Thr Pro Ala Ser Gly Ser Val Thr Glu Asn Asp Thr Trp Arg
545                 550                 555

<210> SEQ ID NO 3
<211> LENGTH: 928
<212> TYPE: PRT
<213> ORGANISM: Bacillus deramificans

<400> SEQUENCE: 3

Asp Gly Asn Thr Thr Ile Ile Val His Tyr Phe Arg Pro Ala Gly
1               5                   10                  15

Asp Tyr Gln Pro Trp Ser Leu Trp Met Trp Pro Lys Asp Gly Gly
                20                  25                  30

Ala Glu Tyr Asp Phe Asn Gln Pro Ala Asp Ser Phe Gly Ala Val Ala
```

```
                35                  40                  45
Ser Ala Asp Ile Pro Gly Asn Pro Ser Gln Val Gly Ile Val Arg
 50                  55                  60
Thr Gln Asp Trp Thr Lys Asp Val Ser Ala Asp Arg Tyr Ile Asp Leu
 65                  70                  75                  80
Ser Lys Gly Asn Glu Val Trp Leu Val Glu Gly Asn Ser Gln Ile Phe
                 85                  90                  95
Tyr Asn Glu Lys Asp Ala Glu Asp Ala Ala Lys Pro Ala Val Ser Asn
                100                 105                 110
Ala Tyr Leu Asp Ala Ser Asn Gln Val Leu Val Lys Leu Ser Gln Pro
            115                 120                 125
Leu Thr Leu Gly Glu Gly Ala Ser Gly Phe Thr Val His Asp Asp Thr
    130                 135                 140
Ala Asn Lys Asp Ile Pro Val Thr Ser Val Lys Asp Ala Ser Leu Gly
145                 150                 155                 160
Gln Asp Val Thr Ala Val Leu Ala Gly Thr Phe Gln His Ile Phe Gly
                165                 170                 175
Gly Ser Asp Trp Ala Pro Asp Asn His Ser Thr Leu Leu Lys Lys Val
            180                 185                 190
Thr Asn Asn Leu Tyr Gln Phe Ser Gly Asp Leu Pro Glu Gly Asn Tyr
    195                 200                 205
Gln Tyr Lys Val Ala Leu Asn Asp Ser Trp Asn Asn Pro Ser Tyr Pro
210                 215                 220
Ser Asp Asn Ile Asn Leu Thr Val Pro Ala Gly Gly Ala His Val Thr
225                 230                 235                 240
Phe Ser Tyr Ile Pro Ser Thr His Ala Val Tyr Asp Thr Ile Asn Asn
                245                 250                 255
Pro Asn Ala Asp Leu Gln Val Glu Ser Gly Val Lys Thr Asp Leu Val
                260                 265                 270
Thr Val Thr Leu Gly Glu Asp Pro Asp Val Ser His Thr Leu Ser Ile
            275                 280                 285
Gln Thr Asp Gly Tyr Gln Ala Lys Gln Val Ile Pro Arg Asn Val Leu
    290                 295                 300
Asn Ser Ser Gln Tyr Tyr Tyr Ser Gly Asp Asp Leu Gly Asn Thr Tyr
305                 310                 315                 320
Thr Gln Lys Ala Thr Thr Phe Lys Val Trp Ala Pro Thr Ser Thr Gln
                325                 330                 335
Val Asn Val Leu Leu Tyr Asp Ser Ala Thr Gly Ser Val Thr Lys Ile
                340                 345                 350
Val Pro Met Thr Ala Ser Gly His Gly Val Trp Glu Ala Thr Val Asn
            355                 360                 365
Gln Asn Leu Glu Asn Trp Tyr Tyr Met Tyr Glu Val Thr Gly Gln Gly
    370                 375                 380
Ser Thr Arg Thr Ala Val Asp Pro Tyr Ala Thr Ala Ile Ala Pro Asn
385                 390                 395                 400
Gly Thr Arg Gly Met Ile Val Asp Leu Ala Lys Thr Asp Pro Ala Gly
                405                 410                 415
Trp Asn Ser Asp Lys His Ile Thr Pro Lys Asn Ile Glu Asp Glu Val
                420                 425                 430
Ile Tyr Glu Met Asp Val Arg Asp Phe Ser Ile Asp Pro Asn Ser Gly
            435                 440                 445
Met Lys Asn Lys Gly Lys Tyr Leu Ala Leu Thr Glu Lys Gly Thr Lys
    450                 455                 460
```

```
Gly Pro Asp Asn Val Lys Thr Gly Ile Asp Ser Leu Lys Gln Leu Gly
465                 470                 475                 480

Ile Thr His Val Gln Leu Met Pro Val Phe Ala Ser Asn Ser Val Asp
                485                 490                 495

Glu Thr Asp Pro Thr Gln Asp Asn Trp Gly Tyr Asp Pro Arg Asn Tyr
            500                 505                 510

Asp Val Pro Glu Gly Gln Tyr Ala Thr Asn Ala Asn Gly Asn Ala Arg
        515                 520                 525

Ile Lys Glu Phe Lys Glu Met Val Leu Ser Leu His Arg Glu His Ile
    530                 535                 540

Gly Val Asn Met Asp Val Val Tyr Asn His Thr Phe Ala Thr Gln Ile
545                 550                 555                 560

Ser Asp Phe Asp Lys Ile Val Pro Glu Tyr Tyr Tyr Arg Thr Asp Asp
                565                 570                 575

Ala Gly Asn Tyr Thr Asn Gly Ser Gly Thr Gly Asn Glu Ile Ala Ala
            580                 585                 590

Glu Arg Pro Met Val Gln Lys Phe Ile Ile Asp Ser Leu Lys Tyr Trp
        595                 600                 605

Val Asn Glu Tyr His Ile Asp Gly Phe Arg Phe Asp Leu Met Ala Leu
    610                 615                 620

Leu Gly Lys Asp Thr Met Ser Lys Ala Ala Ser Glu Leu His Ala Ile
625                 630                 635                 640

Asn Pro Gly Ile Ala Leu Tyr Gly Glu Pro Trp Thr Gly Gly Thr Ser
                645                 650                 655

Ala Leu Pro Asp Asp Gln Leu Leu Thr Lys Gly Ala Gln Lys Gly Met
            660                 665                 670

Gly Val Ala Val Phe Asn Asp Asn Leu Arg Asn Ala Leu Asp Gly Asn
        675                 680                 685

Val Phe Asp Ser Ser Ala Gln Gly Phe Ala Thr Gly Ala Thr Gly Leu
    690                 695                 700

Thr Asp Ala Ile Lys Asn Gly Val Glu Gly Ser Ile Asn Asp Phe Thr
705                 710                 715                 720

Ser Ser Pro Gly Glu Thr Ile Asn Tyr Val Thr Ser His Asp Asn Tyr
                725                 730                 735

Thr Leu Trp Asp Lys Ile Ala Leu Ser Asn Pro Asn Asp Ser Glu Ala
            740                 745                 750

Asp Arg Ile Lys Met Asp Glu Leu Ala Gln Ala Val Val Met Thr Ser
        755                 760                 765

Gln Gly Val Pro Phe Met Gln Gly Gly Glu Glu Met Leu Arg Thr Lys
    770                 775                 780

Gly Gly Asn Asp Asn Ser Tyr Asn Ala Gly Asp Ala Val Asn Glu Phe
785                 790                 795                 800

Asp Trp Ser Arg Lys Ala Gln Tyr Pro Asp Val Phe Asn Tyr Tyr Ser
                805                 810                 815

Gly Leu Ile His Leu Arg Leu Asp His Pro Ala Phe Arg Met Thr Thr
            820                 825                 830

Ala Asn Glu Ile Asn Ser His Leu Gln Phe Leu Asn Ser Pro Glu Asn
        835                 840                 845

Thr Val Ala Tyr Glu Leu Thr Asp His Val Asn Lys Asp Lys Trp Gly
    850                 855                 860

Asn Ile Ile Val Val Tyr Asn Pro Asn Lys Thr Val Ala Thr Ile Asn
865                 870                 875                 880
```

```
Leu Pro Ser Gly Lys Trp Ala Ile Asn Ala Thr Ser Gly Lys Val Gly
                885                 890                 895

Glu Ser Thr Leu Gly Gln Ala Glu Gly Ser Val Gln Val Pro Gly Ile
            900                 905                 910

Ser Met Met Ile Leu His Gln Glu Val Ser Pro Asp His Gly Lys Lys
        915                 920                 925

<210> SEQ ID NO 4
<211> LENGTH: 583
<212> TYPE: PRT
<213> ORGANISM: Artificial
<220> FEATURE:
<223> OTHER INFORMATION: Rhizomucor pusillus core with linker and SBD
      from A. niger glucoamylase

<400> SEQUENCE: 4

Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

Ser Asn Tyr Cys Gly Gly Thr Tyr Glu Gly Ile Thr Lys His Leu Asp
        35                  40                  45

Tyr Ile Ser Gly Met Gly Phe Asp Ala Ile Trp Ile Ser Pro Ile Pro
    50                  55                  60

Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Gly
        115                 120                 125

Asp Ala Ser Leu Tyr His Pro Lys Cys Thr Ile Asp Tyr Asn Asp Gln
    130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
            180                 185                 190

His Ile Arg Lys Asp Phe Trp Thr Gly Tyr Ala Glu Ala Ala Gly Val
        195                 200                 205

Phe Ala Thr Gly Glu Val Phe Asn Gly Asp Pro Ala Tyr Val Gly Pro
    210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
            260                 265                 270

Thr Thr Phe Val Asp Asn His Asp Asn Pro Arg Phe Leu Asn Ser Gln
        275                 280                 285

Ser Asp Lys Ala Leu Phe Lys Asn Ala Leu Thr Tyr Val Leu Leu Gly
    290                 295                 300

Glu Gly Ile Pro Ile Val Tyr Tyr Gly Ser Glu Gln Gly Phe Ser Gly
305                 310                 315                 320
```

Gly Ala Asp Pro Ala Asn Arg Glu Val Leu Trp Thr Thr Asn Tyr Asp
            325                 330                 335

Thr Ser Ser Asp Leu Tyr Gln Phe Ile Lys Thr Val Asn Ser Val Arg
            340                 345                 350

Met Lys Ser Asn Lys Ala Val Tyr Met Asp Ile Tyr Val Gly Asp Asn
            355                 360                 365

Ala Tyr Ala Phe Lys His Gly Asp Ala Leu Val Val Leu Asn Asn Tyr
        370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
            405                 410                 415

Val Ser Ser Asp Gly Thr Val Thr Phe Asn Leu Lys Asp Gly Leu Pro
            420                 425                 430

Ala Ile Phe Thr Ser Ala Thr Gly Gly Thr Thr Thr Ala Thr Pro
            435                 440                 445

Thr Gly Ser Gly Ser Val Thr Ser Thr Ser Lys Thr Thr Ala Thr Ala
            450                 455                 460

Ser Lys Thr Ser Thr Ser Thr Ser Thr Ser Cys Thr Thr Pro Thr
465                 470                 475                 480

Ala Val Ala Val Thr Phe Asp Leu Thr Ala Thr Thr Thr Tyr Gly Glu
            485                 490                 495

Asn Ile Tyr Leu Val Gly Ser Ile Ser Gln Leu Gly Asp Trp Glu Thr
            500                 505                 510

Ser Asp Gly Ile Ala Leu Ser Ala Asp Lys Tyr Thr Ser Ser Asp Pro
            515                 520                 525

Leu Trp Tyr Val Thr Val Thr Leu Pro Ala Gly Glu Ser Phe Glu Tyr
            530                 535                 540

Lys Phe Ile Arg Ile Glu Ser Asp Asp Ser Val Glu Trp Glu Ser Asp
545                 550                 555                 560

Pro Asn Arg Glu Tyr Thr Val Pro Gln Ala Cys Gly Thr Ser Thr Ala
            565                 570                 575

Thr Val Thr Asp Thr Trp Arg
            580

<210> SEQ ID NO 5
<211> LENGTH: 828
<212> TYPE: PRT
<213> ORGANISM: Artificial
<220> FEATURE:
<223> OTHER INFORMATION: Hybrid variant pullulanase

<400> SEQUENCE: 5

Asp Ser Thr Ser Thr Glu Val Ile Val His Tyr His Arg Phe Asp Ser
1               5                   10                  15

Asn Tyr Ala Asn Trp Asp Leu Trp Met Trp Pro Tyr Gln Pro Val Asn
            20                  25                  30

Gly Asn Gly Ala Ala Tyr Glu Phe Ser Gly Lys Asp Asp Phe Gly Val
        35                  40                  45

Lys Ala Asp Val Gln Val Pro Gly Asp Thr Gln Val Gly Leu Ile
    50                  55                  60

Val Arg Thr Asn Asp Trp Ser Gln Lys Asn Ser Asp Asp Leu His
65                  70                  75                  80

Ile Asp Leu Thr Lys Gly His Glu Ile Trp Ile Val Gln Gly Asp Pro
                85                  90                  95

```
Asn Ile Tyr Tyr Asn Leu Ser Asp Ala Gln Ala Ala Thr Pro Lys
            100                 105                 110

Val Ser Asn Ala Tyr Leu Asp Asn Glu Lys Thr Val Leu Ala Lys Leu
                115                 120                 125

Thr Asn Pro Met Thr Leu Ser Asp Gly Ser Ser Gly Phe Thr Val Thr
130                 135                 140

Asp Lys Thr Thr Gly Glu Gln Ile Pro Val Thr Ala Ala Thr Asn Ala
145                 150                 155                 160

Asn Ser Ala Ser Ser Ser Glu Gln Thr Asp Leu Val Gln Leu Thr Leu
                165                 170                 175

Ala Ser Ala Pro Asp Val Ser His Thr Ile Gln Val Gly Ala Ala Gly
                180                 185                 190

Tyr Glu Ala Val Asn Leu Ile Pro Arg Asn Val Leu Asp Ser Ser Gln
            195                 200                 205

Tyr Tyr Tyr Ser Gly Asp Asp Leu Gly Asn Thr Tyr Thr His Lys Ala
        210                 215                 220

Thr Thr Phe Lys Val Trp Ala Pro Thr Ser Thr Gln Val Asn Val Leu
225                 230                 235                 240

Leu Tyr Asn Ser Ala Thr Gly Ser Val Thr Lys Thr Val Pro Met Thr
                245                 250                 255

Ala Ser Gly His Gly Val Trp Glu Ala Thr Val Asn Gln Asn Leu Glu
                260                 265                 270

Asn Trp Tyr Tyr Met Tyr Glu Val Thr Gly Gln Gly Ser Thr Arg Thr
            275                 280                 285

Ala Val Asp Pro Tyr Ala Thr Ala Ile Ala Pro Asn Gly Thr Arg Gly
            290                 295                 300

Met Ile Val Asp Leu Ala Lys Thr Asp Pro Ala Gly Trp Asn Ser Asp
305                 310                 315                 320

Lys His Ile Thr Pro Lys Asn Ile Glu Asp Glu Val Ile Tyr Glu Met
                325                 330                 335

Asp Val Arg Asp Phe Ser Ile Asp Pro Asn Ser Gly Met Lys Asn Lys
            340                 345                 350

Gly Lys Tyr Leu Ala Leu Thr Glu Lys Gly Thr Lys Gly Pro Asp Gly
            355                 360                 365

Val Lys Thr Gly Ile Asp Ser Leu Lys Gln Leu Gly Ile Thr His Val
            370                 375                 380

Gln Leu Met Pro Val Phe Ala Phe Ala Ser Val Asp Glu Thr Asp Pro
385                 390                 395                 400

Thr Gln Asp Asn Trp Gly Tyr Asp Pro Arg Asn Tyr Asp Val Pro Glu
                405                 410                 415

Gly Gln Tyr Ala Thr Asn Ala Asn Gly Thr Ala Arg Ile Lys Glu Phe
            420                 425                 430

Lys Glu Met Val Leu Ser Leu His Arg Glu His Ile Gly Val Asn Met
            435                 440                 445

Asp Val Val Tyr Asn His Thr Phe Ala Thr Gln Ile Ser Asp Phe Asp
            450                 455                 460

Lys Ile Val Pro Glu Tyr Tyr Arg Thr Asp Asp Ala Gly Asn Tyr
465                 470                 475                 480

Thr Asn Gly Ser Gly Thr Gly Asn Glu Ile Ala Ser Glu Arg Pro Met
                485                 490                 495

Val Gln Lys Phe Ile Ile Asp Ser Leu Lys Tyr Trp Val Asn Glu Tyr
            500                 505                 510
```

```
His Ile Asp Gly Phe Arg Phe Asp Leu Met Ala Leu Leu Gly Lys Asp
        515                 520                 525

Thr Met Ser Lys Ala Ala Ser Glu Leu His Ala Ile Asn Pro Gly Ile
    530                 535                 540

Ala Leu Tyr Gly Glu Pro Trp Thr Gly Gly Thr Ser Ala Leu Pro Glu
545                 550                 555                 560

Asp Gln Leu Leu Thr Lys Gly Ala Gln Lys Gly Met Gly Val Ala Val
                565                 570                 575

Phe Asn Asp Asn Leu Arg Asn Ala Leu Asp Gly Asn Val Phe Asp Ser
            580                 585                 590

Ser Ala Gln Gly Phe Ala Thr Gly Ala Thr Gly Leu Thr Asp Ala Ile
            595                 600                 605

Lys Asn Gly Val Glu Gly Ser Ile Asn Asp Phe Thr Ser Ser Pro Gly
        610                 615                 620

Glu Thr Ile Asn Tyr Val Thr Ser His Asp Asn Tyr Thr Leu Trp Asp
625                 630                 635                 640

Lys Ile Ala Leu Ser Asn Pro Asn Asp Ser Glu Ala Asp Arg Ile Lys
                645                 650                 655

Met Asp Glu Leu Ala Gln Ala Val Val Met Thr Ser Gln Gly Val Pro
            660                 665                 670

Phe Met Gln Gly Gly Glu Glu Met Leu Arg Thr Lys Gly Gly Asn Asp
        675                 680                 685

Asn Ser Tyr Asn Ala Gly Asp Thr Val Asn Glu Phe Asp Trp Ser Arg
        690                 695                 700

Lys Ala Gln Tyr Pro Asp Val Phe Asn Tyr Tyr Ser Gly Leu Ile His
705                 710                 715                 720

Leu Arg Leu Asp His Pro Ala Phe Arg Met Thr Thr Ala Asn Glu Ile
                725                 730                 735

Asn Ser His Leu Gln Phe Leu Asn Ser Pro Glu Asn Thr Val Ala Tyr
            740                 745                 750

Glu Leu Thr Asp His Val Asn Lys Asp Lys Trp Gly Asn Ile Ile Val
            755                 760                 765

Val Tyr Asn Pro Asn Lys Thr Ala Ala Thr Ile Asn Leu Pro Ser Gly
770                 775                 780

Lys Trp Ala Ile Asn Ala Thr Ser Gly Lys Val Gly Glu Ser Thr Leu
785                 790                 795                 800

Gly Gln Ala Glu Gly Ser Val Gln Val Pro Gly Ile Ser Met Met Ile
            805                 810                 815

Leu His Gln Glu Val Ser Pro Asp His Gly Lys Lys
            820                 825
```